US012285474B2

(12) United States Patent
Papavasiliou et al.

(10) Patent No.: US 12,285,474 B2
(45) Date of Patent: Apr. 29, 2025

(54) VSG-BASED VACCINATION AND ANTIBODY GENERATION PLATFORM FOR THE TREATMENT OF DISEASES

(71) Applicant: Deutsches Krebsforschungszentrum Stiftung des öffentlichen Rechts, Heidelberg (DE)

(72) Inventors: Fotini Nina Papavasiliou, Heidelberg (DE); Hamidreza Hashemi, Heidelberg (DE); Gianna Triller, Heidelberg (DE); Erec Stebbins, Heidelberg (DE); Aubry Miller, Heidelberg (DE); Andreas Baumann, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 957 days.

(21) Appl. No.: 17/288,208

(22) PCT Filed: Oct. 24, 2019

(86) PCT No.: PCT/EP2019/079063
§ 371 (c)(1),
(2) Date: Apr. 23, 2021

(87) PCT Pub. No.: WO2020/084072
PCT Pub. Date: Apr. 30, 2020

(65) Prior Publication Data

US 2021/0401956 A1 Dec. 30, 2021

(30) Foreign Application Priority Data

Oct. 24, 2018 (EP) .................................... 18202305

(51) Int. Cl.
*A61K 39/00* (2006.01)
*A61K 39/385* (2006.01)

(52) U.S. Cl.
CPC ........ *A61K 39/0013* (2013.01); *A61K 39/385* (2013.01); *A61K 2039/521* (2013.01);
(Continued)

(58) Field of Classification Search
None
See application file for complete search history.

(56) References Cited

U.S. PATENT DOCUMENTS

2013/0251740 A1* 9/2013 Papavasiliou ........ A61K 39/005
536/23.7
2021/0401956 A1* 12/2021 Papavasiliou ........... A61P 43/00

FOREIGN PATENT DOCUMENTS

WO 2010087994 A2 8/2010
WO 2011133704 A2 10/2011
WO 2012057934 A1 5/2012

OTHER PUBLICATIONS

Wu et al. (Journal of Carbohydrate Chemistry. 2012; 31 (1): 48-66).*

(Continued)

*Primary Examiner* — Shanon A. Foley
(74) *Attorney, Agent, or Firm* — Taft Stettinius & Hollister LLP

(57) ABSTRACT

The invention is based on a platform for vaccination and/or antibody generation. The invention is based on the display of small molecular immunogenic compounds on the coat of variant surface glycoproteins (VSG) on trypanosomes which results in a highly effective immune response when used as a vaccine or in immunization for antibody production. The herein disclosed antigenic particles are applicable for producing antibodies or can be directly used as vaccines for the treatment of various medical conditions. Most preferably the invention relates to the VSG based vaccines specific for dependency causing substances for the treatment of addiction or avoidance of adverse events during drug abuse. Other (Continued)

Figure 1A:
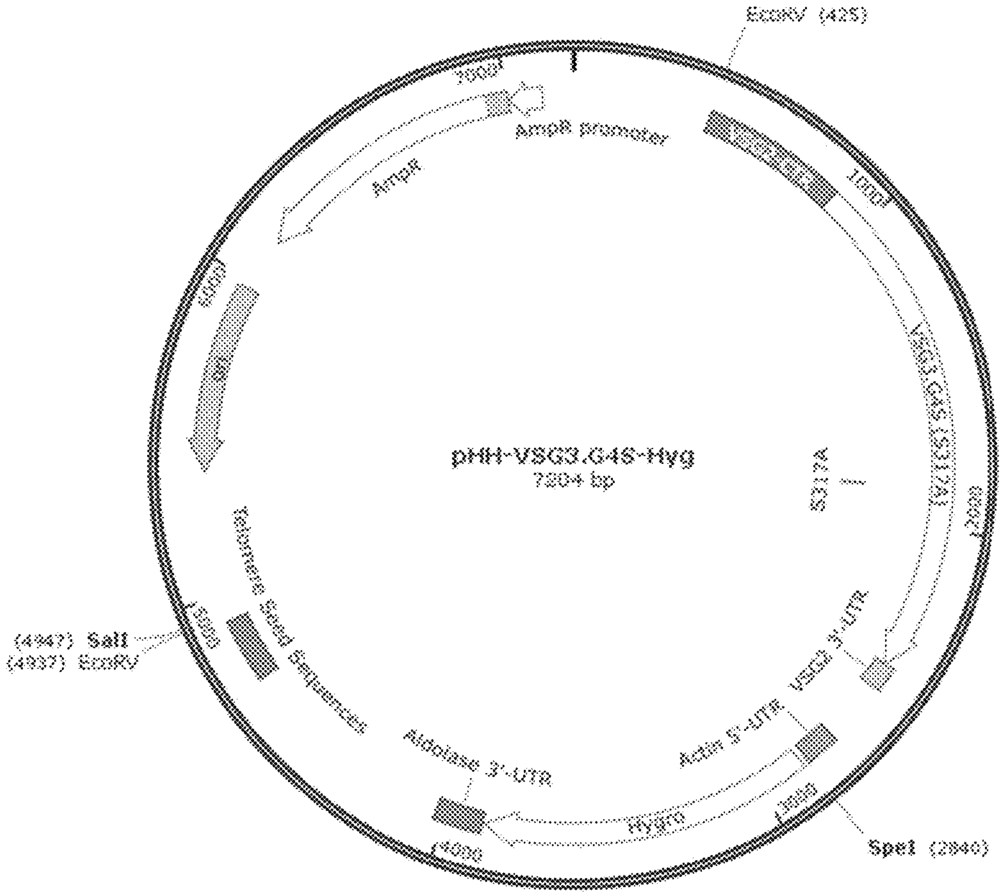

applications include methods and uses involving the disclosed compounds and compositions for a treatment or prevention of cancer, infectious disease, contagious neurodegenerative diseases, non-communicable disorders (e.g. certain neurodegenerative diseases, allergies) and any condition or industrial use for which an immune response from vaccination or antibody use would be desirable.

11 Claims, 18 Drawing Sheets

Specification includes a Sequence Listing.

(52) U.S. Cl.
CPC .. *A61K 2039/523* (2013.01); *A61K 2039/545* (2013.01); *A61K 2039/6031* (2013.01); *A61K 2039/6075* (2013.01)

(56) References Cited

OTHER PUBLICATIONS

Action; Chinese Patent Office; Chinese Application No. 201980070476.3; Aug. 17, 2023; 22 pages.
International Search Report; European Patent Office; International Application No. PCT/EP2019/079063; Feb. 7, 2020; 5 pages.
Written Opinion of the International Searching Authority; European Patent Office; International Application No. PCT/EP2019/079063; Feb. 7, 2020; 8 pages.
Japanese Office Action, Japan Patent Office, Japanese Patent Application No. 2021-522091, Jul. 5, 2022, 7 pages.
Stavropoulos et al., "Using T.brucei as a biological epitope-display platform to elicit specific antibody responses", National Institute of Health, J Immunol Methods, Oct. 2010, 8 pages.
Aceto, M. D. et al.; Effects of opiates and opiate antagonists on the Straub tail reaction in mice; Br. J. Pharmac.; Jun. 1969; pp. 225-239; vol. 36; No. 2.
Bilbey, D. L. J. et al.; The Anatomical Basis of the Straub Phenomenon; Brit. J. Pharmacol.; Dec. 1960; pp. 540-543; vol. 15; No. 4.
Cross, George A.M. et al.; Capturing the variant surface glycoprotein repertoire (the VSGnome) of Trypanosoma brucel Lister 427; Molecular & Biochemical Parasitology; Jun. 30, 2014; pp. 59-73; vol. 195; Elsevier B.V.
Dole, Vincent P. et al.; Study of methadone as an adjunct in rehabilitation of heroin addicts; Illinois Medical Journal; Oct. 1966; pp. 487-489; vol. 130; No. 4.
Kantak, Kathleen M; Anti-cocaine vaccines: antibody protection against relapse; Expert Opinion on Pharmacotherapy; Feb. 2003; pp. 213-218; vol. 4; No. 2; Ashley Publications Ltd.
Kantak, Kathleen M.; Vaccines Against Drugs of Abuse: A Viable Treatment Option ?; Drugs; 2003; pp. 341-352; vol. 63; No. 4; Adis International Limited.
Kolb, Hartmuth C. et al.; Click Chemistry: Diverse Chemical Function from a Few Good Reactions; Angew. Chem. Int. Ed.; Jun. 1, 2001; pp. 2004-2021; vol. 40; No. 11; WILEY-VCH Verlag GmbH.
Kreek, Mary Jeanne; Methadone-Related Opioid Agonist Pharmacotherapy for Heroin Addiction: History, Recent Molecular and Neurochemical Research and Future In Mainstream Medicine; Annals New York Academy of Sciences; 2000; pp. 186-216; vol. 909.
Martell, Bridget A. et al.; Cocaine Vaccine for the Treatment of Cocaine Dependence in Methadone Maintained Patients: A Randomized Double-Blind Placebo-Controlled Efficacy Trial; Arch Gen Psychiatry; Oct. 2009; pp. 1116-1123; vol. 66; No. 10.
Nath, Chandishwar et al.; Morphine-induced straub tail response: mediated by central u2-opioid receptor; European Journal of Pharmacology; 1994; pp. 203-205; vol. 263; Elsevier Science B.V.
Tiller, Thomas et al.; Efficient generation of monoclonal antibodies from single human B cells by single cell RT-PCR and expression vector cloning; J Immunol Methods; Jan. 1, 2008; pp. 112-124; vol. 329; Nos. 1-2.
Zarrindast, Mohammad-Reza et al.; On the mechanism of tolerance to morphine-induced Straub tail reaction in mice; Pharmacology, Biochemistry and Behavior; 2001; pp. 419-424; vol. 69; Elsevier Science Inc.
Pinger, Jason et al.; Variant surface glycoprotein density defines an immune evasion threshold for African trypanosomes undergoing antigenic variation; Nature Communications; 2017; 9 pages; vol. 8; No. 828.
Pallen, Mark J. et al.; An embarrassment of sortases—a richness of substrates ?; TRENDS in Microbiology; Mar. 2001; pp. 97-101; vol. 9; No. 3; Elsevier Science Ltd.
Dramsi, Shaynoor et al.; Sorting sortases: a nomenclature proposal for the various sortases of Gram-positive bacteria; Research in Microbiology: 2005; pp. 289-297; vol. 156; Elsevier SAS.
Comfort, David et al.; A Comparative Genome Analysis Identifies Distinct Sorting Pathways in Gram-Positive Bacteria; Infection and Immunity; May 2004; pp. 2710-2722; vol. 72; No. 5; American Society for Microbiology.
Chen, Irwin et al.; A general strategy for the evolution of bond-forming enzymes using yeast display; PNAS; Jul. 12, 2011; pp. 11399-11404; vol. 108; No. 28.
Stavropoulos, Pete et al.; Using T. brucel as a biological epitope-display platform to elicit specific antibody responses; Journal of Immunological Methods; Aug. 26, 2010; pp. 190-194; vol. 362; Elsevier B.V.
Raleigh, Michael D. et al.; A Fentanyl Vaccine Alters Fentanyl Distribution and Protects against Fentanyl-Induced Effects in Mice and Rats; The Journal of Pharmacology and Experimental Therapeutics; Feb. 2019; pp. 282-291; vol. 368; The American Society for Pharmacology and Experimental Therapeutics.
International Preliminary Report on Patentability; The International Bureau of WIPO; International Application No. PCT/EP2019/079063; May 6, 2021: 10 pages.
Fox, Barbara S. et al.; Efficacy of a therapeutic cocaine vaccine in rodent models; Nature Medicine; Oct. 1996; pp. 1129-1132; vol. 2, No. 10; Nature Publishing Group.
Shen, Xiaoyun et al.; Immunotherapy for Drug Abuse; CNS Neurol Disord Drug Targets; Dec. 2011; pp. 876-879; vol. 10, No. 8; Bentham Science Publishers.
Raleigh, Michael et al.; Selective effects of a morphine conjugate vaccine on heroin and metabolite distribution and heroin-induced behaviors in rats; 2012; 44 pages; American Society for Pharmacology and Experimental Therapeutics.
Raleigh, Michael et al.; Safety and efficacy of an oxycodone vaccine: Addressing some of the unique considerations posed by opioid abuse; PLOS One; Dec. 1, 2017; 18 pages; vol. 12, No. 12.
Raleigh, Michael et al.; Opioid Dose-and Route-Dependent Efficacy of Oxycodone and Heroin Vaccines in Rats; The Journal of Pharmacology and Experimental Therapeutics; May 2018; pp. 346-353; vol. 365; American Society for Pharmacology and Experimental Therapeutics.
Tang, Shubing et al.; A Modular Vaccine Development Platform Based on SortaseMediated Site-Specific Tagging of Antigens onto Virus-Like Particles; Scientific reports; May 12, 2016; 9 pages; vol. 6.
Pinger, Jason et al.; African trypanosomes evade immune clearance by O-glycosylation of the VSG surface coat; Nat Microbiol.; Aug. 2018; pp. 932-938; vol. 3, No. 8.
Straub, W.; A sensitive biological response to morphine; German Medical Weekly; 1911; p. 1462; vol. 37, No. 31.
Pinger, Jason M.; Surface Coat Replacement Dynamics and Antigen Glycosylation in T. Brucei Influence Evasion of the Host Antibody Response; Student Theses and Dissertations; Jun. 2018; 129 pages.

* cited by examiner

Knock-In of Sortaggable VSG2 (VSG2-1DK) into Active Expression Site of VSG2

Knock-In of Sortaggable VSG3 (VSG3-G4S) into Active Expression Site of VSG2

Knock-In of Sortaggable ILTat1.24 (ILTat1.24-G4S) into Active Expression Site of VSG2

FIGURE 4A

1 MQAAALLLLV LRAITSIEAA AGGGGSGGGG SGGGGSDDVN PDDNKEDFAV

51 LCALAALANL QTTVPSIDTS GLAAYDNLQQ LNLSLSSKEW KSLFNKAADS

101 NGSPKQPPEG FQSDPTWKKQ WPIWVTAAAA LKAENKEAAV LARAGLTNAP

151 EELRNRARLA LIPLLAQAEQ IRDRLSEIQK QNEDTTPTAI AKALNKAVYG

201 QDKETGAVYN SADCFSGNVA DSTQNSCKAG NQASKATTVA ATIVCVCHKK

251 NGGNDAANAC GRLINHQSDA GANLATASSD FGDIIATCAA RPPKPLTAAY

301 LDSALAAVSA RIRFKNGNGY LGKFKATGCT GAASEGLCVE YTALTAATMQ

351 NFYKIPWVKE ISNVAEALKR TEKDAAESTL LSTWLKASEN QGNSVAQKLI

401 KVGDSKAVPP AQRQTQNKPG SNCNKNLKKS ECKDSDGCKW NRTEETEGDF

451 CKPKETGTEN PAAGTGEGAA GANTETKKCS DKKTEGDCKD GCKWDGKECK

501 DSSILATKKF ALTVVSAAFV ALLF (SEQ ID NO: 9)

FIGURE 4B

1 MPSNQEARLF LAVLVLAQVL PILVDSAAGG GENLYFQGGG GGGFKQAFWQ

51 PLCQVSEELD DQPKGALFTL QAAASKIQKM RDAALRASIY AEINHGTNRA

101 KAAVIVANHY AMKADSGLEA LKQTLSSQEV TATATASYLK GRIDEYLNLL

151 LQTKESGTSG CMMDTSGTNT VTKAGGTIGG VPCKLQLSPI QPKRPAATYL

201 GKAGYVGLTR QADAANNFHD NDAECRLASG HNTNGLGKSG QLSAAVTMAA

251 GYVTVANSQT AVTVQALDAL QEASGAAHQP WIDAWKAKKA LTGAETAEFR

301 NETAGIAGKT GVTKLVEEAL LKKKDSEASE IQTELKKYFS GHENEQWTAI

351 EKLISEQPVA QNLVGDNQPT KLGELEGNAK LTTILAYYKM ETAGKFEVLT

401 QKHKPAESQQ QAAETEGSCN KKDQNECKSP CKWHNDAENK KCTLDKEEAK

451 KVADETAKDG KTGNTNTTGS SNSFVISKTP LWLAVLLF (SEQ ID NO: 10)

FIGURE 4C

1 MVYRNILQLS VLKVLLIVLI VEAGGGGSGG GGSGGGGSTH FGVKYELWQP

51 ECELTAELRK TAGVAKMKVN SDLNSFKTLE LTKMKLLTFA AKFPESKEAL

101 TLRALEAALN TDLRALRDNI ANGIDRAVRA TAYASEAAGA LFSGIQTLHD

151 ATDGTTYCLS ASGQGSNGNA AMASQGCKPL ALPELLTEDS YNTDVISDKG

201 FPKISPLTNA QGQGKSGECG LFQAASGAQA TNTGVQFSGG SRINLGLGAI

251 VASAAQQPTR FDLSDFSGTA RNQADTLYGK AHASITELLQ LAQGPKPGQT

301 EVETMKLLAQ KTAALDSIKF QLAASTGKKT SDYKEDENLK TEYFGKTESN

351 IEALWNKVKE EKVKGADPED PSKESKISDL NTEEQLQRVL DYYAVATMLK

401 LAKQAEDIAK LETEIADQRG KSPEAECNKI TEEPKCSEEK ICSWHKEVKA

451 GEKNCQFNST KASKSGVPVT QTQTAGADTT AEKCKGKGEK DCKSPDCKWE

501 GGTCKDSSIL ANKQFALSVA SAAFVALLF (SEQ ID NO: 11)

| Sample | Mode | Median |
|---|---|---|
| VSG2-Fen | 149 | 154 |
| VSG3-Fen | 178 | 182 |
| ILTat1.24-Fen | 505 | 526 |
| VSG2 | 1.00 | 4.10 |
| VSG3 | 1.00 | 5.74 |
| ILTat1.24 | 1.00 | 6.85 |
| VSG2-FAM | 898 | 965 |
| VSG3-FAM | 1197 | 1208 |
| ILTat1.24-FAM | 1778 | 1981 |

VSG3 IgG (Serum Dilution 1:800)

| Prime | VSG3 (Intact Coat) | VSG3-NP (Intact Coat) | NP-CGG (in Alum) |
|---|---|---|---|
| Boost | NP-CGG (Soluble) | VSG3-NP (Soluble) | NP-CGG (Soluble) |

FIGURE 10A

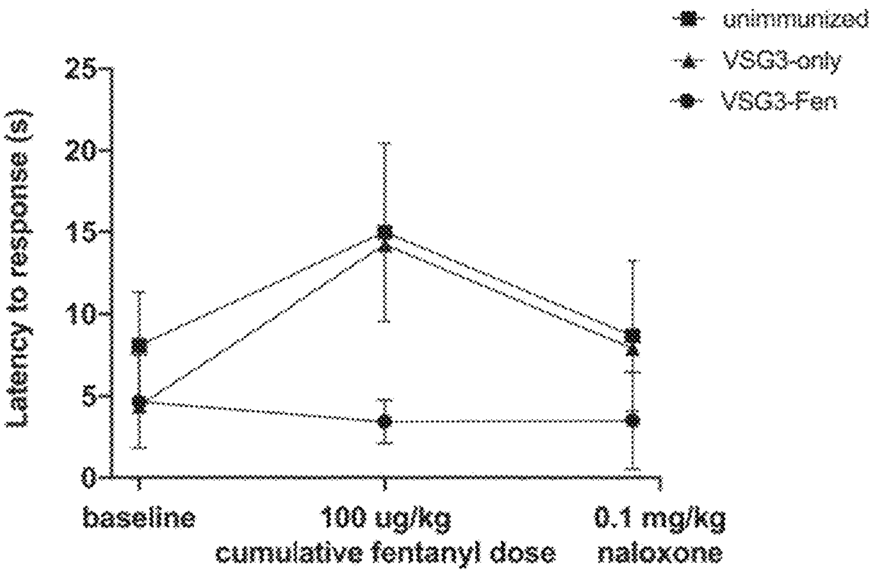

FIGURE 10B

Table. Fentanyl induced Straub tail reaction or STR (at 15min post injection).

| | No drug | 0.1mg/kg Fent | +Naloxone |
|---|---|---|---|
| Control (PBS) | nr* (4/4) | 100% (4/4) | nr (4/4) |
| Vehicle (VSG3) | nr (6/6) | 100% (6/6) | nr (6/6) |
| Exp. (VSG3-Fent) | nr (6/6) | nr (6/6) | nr (6/6) |
| | | | |

% denotes number of mice that demonstrated the straub tail reaction (STR). This is a dorsiflexion of the tail that is often almost vertical to the orientation of the body and stereotyped walking behavior and is thought to be mediated by activation of the opioid receptor system because opioid receptor antagonists such as naloxone block the phenomenon.

nr= no response (normal mouse gait, exploratory behavior etc)

SEQUENCE LISTING

```
<160> NUMBER OF SEQ ID NOS: 17

<210> SEQ ID NO 1
<211> LENGTH: 492
<212> TYPE: PRT
<213> ORGANISM: Trypanosoma brucei

<400> SEQUENCE: 1

Met Ala Thr Gly Arg Ala Lys Asn Thr Lys Trp Ala Arg Trp Leu Ser
1               5                   10                  15

Thr Ala Gly Leu Ile Ile Val Val Thr Leu Pro Ala Thr Thr Met Ala
            20                  25                  30

Ala Glu Arg Thr Gly Leu Lys Ala Thr Ala Trp Lys Pro Leu Cys Lys
        35                  40                  45

Leu Thr Thr Glu Leu Ser Lys Val Ser Gly Glu Met Leu Asn Glu Gly
    50                  55                  60

Gln Glu Val Ile Ser Asn Ile Gln Lys Ile Lys Ala Ala Glu Tyr Lys
65                  70                  75                  80

Val Ser Ile Tyr Leu Ala Lys Asn Pro Glu Thr Gln Ala Leu Gln Gln
                85                  90                  95

Leu Thr Leu Leu Arg Gly Tyr Phe Ala Arg Lys Thr Asn Gly Gly Leu
            100                 105                 110

Glu Ser Tyr Lys Thr Met Gly Leu Ala Thr Gln Ile Arg Ser Ala Arg
        115                 120                 125

Ala Ala Ala Tyr Leu Lys Gly Ser Ile Asp Glu Phe Leu Asn Leu Leu
    130                 135                 140

Glu Ser Leu Lys Gly Gly Ser Glu Asn Lys Cys Leu Val Thr Thr Asn
145                 150                 155                 160

Ala Asp Thr Ala Ala Thr Arg Arg Glu Thr Lys Leu Asp Asp Gln Glu
                165                 170                 175

Cys Ala Leu Ser Met Pro Glu Thr Lys Pro Glu Ala Ala Thr Arg Thr
            180                 185                 190

Glu Leu Thr Gln Thr Gly Tyr Pro Asn Leu Gln His Gly Gly Gly Gly
        195                 200                 205
```

-continued

Thr Ala Asn Thr Phe Gln Pro Thr Thr Ser Thr Gly Thr Cys Lys Leu
    210                 215                 220

Leu Ser Gly His Ser Thr Asn Gly Tyr Pro Thr Thr Ser Ala Leu Asp
225                 230                 235                 240

Thr Thr Ala Lys Val Leu Ala Gly Tyr Met Thr Ile Pro Asn Thr Gln
                245                 250                 255

Val Glu Ala Thr Leu Ala Asn Met Gln Ala Met Gly Asn Gly His Lys
            260                 265                 270

Ala Thr Ala Pro Ala Trp His Glu Ala Trp Glu Ala Arg Asn Arg Glu
        275                 280                 285

Ala Lys Ala Lys Asp Leu Ala Tyr Thr Asn Glu Thr Gly Asn Leu Asp
    290                 295                 300

Thr Gln Pro Thr Leu Lys Ala Leu Val Lys Thr Leu Leu Leu Pro Lys
305                 310                 315                 320

Asp Asn Thr Glu His Asn Ala Glu Ala Thr Lys Leu Glu Ala Leu Phe
                325                 330                 335

Gly Gly Leu Ala Ala Asp Lys Thr Lys Thr Tyr Leu Asp Met Val Asp
            340                 345                 350

Ala Glu Ile Ile Pro Ala Gly Ile Ala Gly Arg Thr Thr Glu Ala Pro
        355                 360                 365

Leu Gly Lys Ile His Asp Thr Val Glu Leu Gly Asp Ile Leu Ser Asn
    370                 375                 380

Tyr Glu Met Ile Ala Ala Gln Asn Val Val Thr Leu Lys Lys Asn Leu
385                 390                 395                 400

Asp Ala Val Ser Lys Lys Gln Gln Thr Glu Ser Ala Glu Asn Lys Glu
                405                 410                 415

Lys Ile Cys Asn Ala Ala Lys Asp Asn Gln Lys Ala Cys Glu Asn Leu
            420                 425                 430

Lys Glu Lys Gly Cys Val Phe Asn Thr Glu Ser Asn Lys Cys Glu Leu
        435                 440                 445

Lys Lys Asp Val Lys Glu Lys Leu Glu Lys Glu Ser Lys Glu Thr Glu
    450                 455                 460

Gly Lys Asp Glu Lys Ala Asn Thr Thr Gly Ser Asn Ser Phe Leu Ile
465                 470                 475                 480

His Lys Ala Pro Leu Leu Leu Ala Phe Leu Leu Phe
                485                 490

<210> SEQ ID NO 2
<211> LENGTH: 476
<212> TYPE: PRT
<213> ORGANISM: Trypanosoma brucei

<400> SEQUENCE: 2

Met Pro Ser Asn Gln Glu Ala Arg Leu Phe Leu Ala Val Leu Val Leu
1               5                   10                  15

Ala Gln Val Leu Pro Ile Leu Val Asp Ser Ala Ala Glu Lys Gly Phe
            20                  25                  30

Lys Gln Ala Phe Trp Gln Pro Leu Cys Gln Val Ser Glu Glu Leu Asp
        35                  40                  45

Asp Gln Pro Lys Gly Ala Leu Phe Thr Leu Gln Ala Ala Ala Ser Lys
    50                  55                  60

Ile Gln Lys Met Arg Asp Ala Ala Leu Arg Ala Ser Ile Tyr Ala Glu
65                  70                  75                  80

Ile Asn His Gly Thr Asn Arg Ala Lys Ala Ala Val Ile Val Ala Asn

```
                85                  90                  95

His Tyr Ala Met Lys Ala Asp Ser Gly Leu Glu Ala Leu Lys Gln Thr
            100                 105                 110

Leu Ser Ser Gln Glu Val Thr Ala Thr Ala Thr Ala Ser Tyr Leu Lys
        115                 120                 125

Gly Arg Ile Asp Glu Tyr Leu Asn Leu Leu Leu Gln Thr Lys Glu Ser
    130                 135                 140

Gly Thr Ser Gly Cys Met Met Asp Thr Ser Gly Thr Asn Thr Val Thr
145                 150                 155                 160

Lys Ala Gly Gly Thr Ile Gly Gly Val Pro Cys Lys Leu Gln Leu Ser
                165                 170                 175

Pro Ile Gln Pro Lys Arg Pro Ala Ala Thr Tyr Leu Gly Lys Ala Gly
            180                 185                 190

Tyr Val Gly Leu Thr Arg Gln Ala Asp Ala Ala Asn Asn Phe His Asp
        195                 200                 205

Asn Asp Ala Glu Cys Arg Leu Ala Ser Gly His Asn Thr Asn Gly Leu
    210                 215                 220

Gly Lys Ser Gly Gln Leu Ser Ala Ala Val Thr Met Ala Ala Gly Tyr
225                 230                 235                 240

Val Thr Val Ala Asn Ser Gln Thr Ala Val Thr Val Gln Ala Leu Asp
                245                 250                 255

Ala Leu Gln Glu Ala Ser Gly Ala Ala His Gln Pro Trp Ile Asp Ala
            260                 265                 270

Trp Lys Ala Lys Lys Ala Leu Thr Gly Ala Glu Thr Ala Glu Phe Arg
        275                 280                 285

Asn Glu Thr Ala Gly Ile Ala Gly Lys Thr Gly Val Thr Lys Leu Val
    290                 295                 300

Glu Glu Ala Leu Leu Lys Lys Lys Asp Ser Glu Ala Ser Glu Ile Gln
305                 310                 315                 320

Thr Glu Leu Lys Lys Tyr Phe Ser Gly His Glu Asn Glu Gln Trp Thr
                325                 330                 335

Ala Ile Glu Lys Leu Ile Ser Glu Gln Pro Val Ala Gln Asn Leu Val
            340                 345                 350

Gly Asp Asn Gln Pro Thr Lys Leu Gly Glu Leu Glu Gly Asn Ala Lys
        355                 360                 365

Leu Thr Thr Ile Leu Ala Tyr Tyr Arg Met Glu Thr Ala Gly Lys Phe
    370                 375                 380

Glu Val Leu Thr Gln Lys His Lys Pro Ala Glu Ser Gln Gln Gln Ala
385                 390                 395                 400

Ala Glu Thr Glu Gly Ser Cys Asn Lys Lys Asp Gln Asn Glu Cys Lys
                405                 410                 415

Ser Pro Cys Lys Trp His Asn Asp Ala Glu Asn Lys Lys Cys Thr Leu
            420                 425                 430

Asp Lys Glu Glu Ala Lys Lys Val Ala Asp Glu Thr Ala Lys Asp Gly
        435                 440                 445

Lys Thr Gly Asn Thr Asn Thr Thr Gly Ser Ser Asn Ser Phe Val Ile
    450                 455                 460

Ser Lys Thr Pro Leu Trp Leu Ala Val Leu Leu Phe
465                 470                 475
```

<210> SEQ ID NO 3
<211> LENGTH: 509
<212> TYPE: PRT
<213> ORGANISM: Trypanosoma brucei -continued

<400> SEQUENCE: 3

```
Met Gln Ala Ala Ala Leu Leu Leu Leu Val Leu Arg Ala Ile Thr Ser
1               5                   10                  15

Ile Glu Ala Ala Ala Asp Asp Val Asn Pro Asp Asp Asn Lys Glu Asp
            20                  25                  30

Phe Ala Val Leu Cys Ala Leu Ala Ala Leu Ala Asn Leu Gln Thr Thr
        35                  40                  45

Val Pro Ser Ile Asp Thr Ser Gly Leu Ala Ala Tyr Asp Asn Leu Gln
    50                  55                  60

Gln Leu Asn Leu Ser Leu Ser Ser Lys Glu Trp Lys Ser Leu Phe Asn
65                  70                  75                  80

Lys Ala Ala Asp Ser Asn Gly Ser Pro Lys Gln Pro Pro Glu Gly Phe
                85                  90                  95

Gln Ser Asp Pro Thr Trp Arg Lys Gln Trp Pro Ile Trp Val Thr Ala
            100                 105                 110

Ala Ala Ala Leu Lys Ala Glu Asn Lys Glu Ala Ala Val Leu Ala Arg
        115                 120                 125

Ala Gly Leu Thr Asn Ala Pro Glu Glu Leu Arg Asn Arg Ala Arg Leu
    130                 135                 140

Ala Leu Ile Pro Leu Leu Ala Gln Ala Glu Gln Ile Arg Asp Arg Leu
145                 150                 155                 160

Ser Glu Ile Gln Lys Gln Asn Glu Asp Thr Thr Pro Thr Ala Ile Ala
                165                 170                 175

Lys Ala Leu Asn Lys Ala Val Tyr Gly Gln Asp Lys Glu Thr Gly Ala
            180                 185                 190

Val Tyr Asn Ser Ala Asp Cys Phe Ser Gly Asn Val Ala Asp Ser Thr
        195                 200                 205

Gln Asn Ser Cys Lys Ala Gly Asn Gln Ala Ser Lys Ala Thr Thr Val
    210                 215                 220

Ala Ala Thr Ile Val Cys Val Cys His Lys Lys Asn Gly Gly Asn Asp
225                 230                 235                 240

Ala Ala Asn Ala Cys Gly Arg Leu Ile Asn His Gln Ser Asp Ala Gly
                245                 250                 255

Ala Asn Leu Ala Thr Ala Ser Ser Asp Phe Gly Asp Ile Ile Ala Thr
            260                 265                 270

Cys Ala Ala Arg Pro Pro Lys Pro Leu Thr Ala Ala Tyr Leu Asp Ser
        275                 280                 285

Ala Leu Ala Ala Val Ser Ala Arg Ile Arg Phe Lys Asn Gly Asn Gly
    290                 295                 300

Tyr Leu Gly Lys Phe Lys Ala Thr Gly Cys Thr Gly Ser Ala Ser Glu
305                 310                 315                 320

Gly Leu Cys Val Glu Tyr Thr Ala Leu Thr Ala Ala Thr Met Gln Asn
                325                 330                 335

Phe Tyr Lys Ile Pro Trp Val Lys Glu Ile Ser Asn Val Ala Glu Ala
            340                 345                 350

Leu Lys Arg Thr Glu Lys Asp Ala Ala Glu Ser Thr Leu Leu Ser Thr
        355                 360                 365

Trp Leu Lys Ala Ser Glu Asn Gln Gly Asn Ser Val Ala Gln Lys Leu
    370                 375                 380

Ile Lys Val Gly Asp Ser Lys Ala Val Pro Pro Ala Gln Arg Gln Thr
385                 390                 395                 400

Gln Asn Lys Pro Gly Ser Asn Cys Asn Lys Asn Leu Lys Lys Ser Glu
```

```
            405                 410                 415

Cys Lys Asp Ser Asp Gly Cys Lys Trp Asn Arg Thr Glu Glu Thr Glu
            420                 425                 430

Gly Asp Phe Cys Lys Pro Lys Glu Thr Gly Thr Glu Asn Pro Ala Ala
        435                 440                 445

Gly Thr Gly Glu Gly Ala Ala Gly Ala Asn Thr Glu Thr Lys Lys Cys
    450                 455                 460

Ser Asp Lys Lys Thr Glu Gly Asp Cys Lys Asp Gly Cys Lys Trp Asp
465                 470                 475                 480

Gly Lys Glu Cys Lys Asp Ser Ser Ile Leu Ala Thr Lys Lys Phe Ala
                485                 490                 495

Leu Thr Val Val Ser Ala Ala Phe Val Ala Leu Leu Phe
            500                 505


<210> SEQ ID NO 4
<211> LENGTH: 499
<212> TYPE: PRT
<213> ORGANISM: Trypanosoma brucei

<400> SEQUENCE: 4

Met Gln Arg Leu Gly Thr Ala Val Phe Phe Leu Leu Ala Phe Arg Tyr
1               5                   10                  15

Ser Thr Glu Gln Ala Val Gly Leu Lys Glu Pro Asn Ala Pro Cys Thr
            20                  25                  30

Thr Ala Cys Gly Cys Lys Ser Arg Leu Leu Lys Arg Leu Asp Leu Tyr
        35                  40                  45

Thr Ser Lys Tyr Ala Asp Gly Ile Asn Asn Glu Arg Glu Asn Ser Glu
    50                  55                  60

Ala Tyr Ser Lys Leu Val Thr Ala Ala Leu Ala Ala Val Pro Thr Met
65                  70                  75                  80

Gln Arg Lys Ile Leu Pro Leu Leu Gly Ala Ala Ala Asp Ile Leu Asp
                85                  90                  95

Ile Cys Arg Arg Glu Leu Ala Thr Ala Arg Pro Leu Val Gln Ala Ala
            100                 105                 110

Ile Ser Lys Ile Glu Glu Ala Ala Gly Val Tyr Asn Thr Leu His Lys
        115                 120                 125

Leu Glu Arg Gly Leu Gly Glu Ala Lys Ile Glu Phe Gly Gly Thr Asp
    130                 135                 140

Leu Arg Leu Thr Lys Thr Lys Phe Arg Ala Thr Ser Leu Gly Thr Ile
145                 150                 155                 160

His Thr Ala Asp Cys Pro Asn Ala Asp Pro Gly Glu Thr Asn Val Lys
                165                 170                 175

Ile Gly Leu Glu His Glu Glu Asn Glu Pro Glu Pro Ala Lys Leu Ile
            180                 185                 190

Thr His Gly His Leu Asp Ala Thr Cys Ala Ser Gly Val Gly Gln Ser
        195                 200                 205

Ser Ser Cys His Thr Thr Ala Val Glu Ala Asn Thr His Leu Thr Leu
    210                 215                 220

Gly Leu Thr Phe Ser Gly Ser Ser Lys Asp Glu Ser Ala Thr Trp Asn
225                 230                 235                 240

Ala Ala Thr Asn Asn Lys Arg Ala Ile His Ser Asn Asp Ala Asp Phe
                245                 250                 255

Leu Gly Ser Asn Ala Thr Val Ala His Glu Ala Leu Lys Ala Ile Arg
            260                 265                 270
```

-continued

```
Ser Ala Gly Ala Ser Thr Pro Cys Ser Ser Leu Ile Thr Asp Phe Asn
        275                 280                 285

Ala Val Arg Ala Asn Pro Lys Phe Lys Leu Met Val Ile Lys Ala Leu
    290                 295                 300

Leu Asn Lys Pro Thr Ala Glu Lys Glu Ser Asp Ala Pro Ala Asp Glu
305                 310                 315                 320

Val Asn Asn Ala Ile Asn Ser Ala Tyr Gly Arg Glu Gly Ser Glu Tyr
                325                 330                 335

Asn Thr Lys Thr Trp Lys Asp Ile Gly Ser Thr Arg Ile Pro Lys Ala
            340                 345                 350

Asp Pro Pro Gly Glu Lys Thr Asp Thr Ile Asp Lys Leu Ser Ser Leu
        355                 360                 365

Pro Gln Trp Gly Asp Ala Ile Ala Arg Leu Leu Leu Gln Glu Ile Thr
    370                 375                 380

Lys Gln Glu Glu Gln Ser Ile Lys Thr Ser Ser Asp Glu Ala Thr Asn
385                 390                 395                 400

Lys Glu Cys Asp Lys His Thr Ala Lys Thr Glu Gly Glu Cys Thr Lys
                405                 410                 415

Leu Gly Cys Asp Tyr Asp Ala Glu Asn Lys Lys Cys Lys Pro Lys Ser
            420                 425                 430

Glu Lys Glu Thr Thr Ala Ala Gly Lys Lys Asp Arg Ala Ala Gly Glu
        435                 440                 445

Thr Gly Cys Ala Lys His Gly Thr Asp Lys Asp Lys Cys Glu Asn Asp
    450                 455                 460

Lys Ser Cys Lys Trp Glu Asn Asn Ala Cys Lys Asp Ser Ser Ile Leu
465                 470                 475                 480

Ala Thr Lys Lys Phe Ala Leu Ser Met Val Ser Ala Ala Phe Val Thr
                485                 490                 495

Leu Leu Phe


<210> SEQ ID NO 5
<211> LENGTH: 514
<212> TYPE: PRT
<213> ORGANISM: Trypanosoma brucei

<400> SEQUENCE: 5

Met Val Tyr Arg Asn Ile Leu Gln Leu Ser Val Leu Lys Val Leu Leu
1               5                   10                  15

Ile Val Leu Ile Val Glu Ala Thr His Phe Gly Val Lys Tyr Glu Leu
            20                  25                  30

Trp Gln Pro Glu Cys Glu Leu Thr Ala Glu Leu Arg Lys Thr Ala Gly
        35                  40                  45

Val Ala Lys Met Lys Val Asn Ser Asp Leu Asn Ser Phe Lys Thr Leu
    50                  55                  60

Glu Leu Thr Lys Met Lys Leu Leu Thr Phe Ala Ala Lys Phe Pro Glu
65                  70                  75                  80

Ser Lys Glu Ala Leu Thr Leu Arg Ala Leu Glu Ala Ala Leu Asn Thr
                85                  90                  95

Asp Leu Arg Ala Leu Arg Asp Asn Ile Ala Asn Gly Ile Asp Arg Ala
            100                 105                 110

Val Arg Ala Thr Ala Tyr Ala Ser Glu Ala Ala Gly Ala Leu Phe Ser
        115                 120                 125

Gly Ile Gln Thr Leu His Asp Ala Thr Asp Gly Thr Thr Tyr Cys Leu
    130                 135                 140
```

-continued

```
Ser Ala Ser Gly Gln Gly Ser Asn Gly Asn Ala Ala Met Ala Ser Gln
145                 150                 155                 160

Gly Cys Lys Pro Leu Ala Leu Pro Glu Leu Leu Thr Glu Asp Ser Tyr
                165                 170                 175

Asn Thr Asp Val Ile Ser Asp Lys Gly Phe Pro Lys Ile Ser Pro Leu
            180                 185                 190

Thr Asn Ala Gln Gly Gln Gly Lys Ser Gly Glu Cys Gly Leu Phe Gln
        195                 200                 205

Ala Ala Ser Gly Ala Gln Ala Thr Asn Thr Gly Val Gln Phe Ser Gly
    210                 215                 220

Gly Ser Arg Ile Asn Leu Gly Leu Gly Ala Ile Val Ala Ser Ala Ala
225                 230                 235                 240

Gln Gln Pro Thr Arg Pro Asp Leu Ser Asp Phe Ser Gly Thr Ala Arg
                245                 250                 255

Asn Gln Ala Asp Thr Leu Tyr Gly Lys Ala His Ala Ser Ile Thr Glu
            260                 265                 270

Leu Leu Gln Leu Ala Gln Gly Pro Lys Pro Gly Gln Thr Glu Val Glu
        275                 280                 285

Thr Met Lys Leu Leu Ala Gln Lys Thr Ala Ala Leu Asp Ser Ile Lys
    290                 295                 300

Phe Gln Leu Ala Ala Ser Thr Gly Lys Lys Thr Ser Asp Tyr Lys Glu
305                 310                 315                 320

Asp Glu Asn Leu Lys Thr Glu Tyr Phe Gly Lys Thr Glu Ser Asn Ile
                325                 330                 335

Glu Ala Leu Trp Asn Lys Val Lys Glu Glu Lys Val Lys Gly Ala Asp
            340                 345                 350

Pro Glu Asp Pro Ser Lys Glu Ser Lys Ile Ser Asp Leu Asn Thr Glu
        355                 360                 365

Glu Gln Leu Gln Arg Val Leu Asp Tyr Tyr Ala Val Ala Thr Met Leu
    370                 375                 380

Lys Leu Ala Lys Gln Ala Glu Asp Ile Ala Lys Leu Glu Thr Glu Ile
385                 390                 395                 400

Ala Asp Gln Arg Gly Lys Ser Pro Glu Ala Glu Cys Asn Lys Ile Thr
                405                 410                 415

Glu Glu Pro Lys Cys Ser Glu Glu Lys Ile Cys Ser Trp His Lys Glu
            420                 425                 430

Val Lys Ala Gly Glu Lys Asn Cys Gln Phe Asn Ser Thr Lys Ala Ser
        435                 440                 445

Lys Ser Gly Val Pro Val Thr Gln Thr Gln Thr Ala Gly Ala Asp Thr
    450                 455                 460

Thr Ala Glu Lys Cys Lys Gly Lys Gly Glu Lys Asp Cys Lys Ser Pro
465                 470                 475                 480

Asp Cys Lys Trp Glu Gly Gly Thr Cys Lys Asp Ser Ser Ile Leu Ala
                485                 490                 495

Asn Lys Gln Phe Ala Leu Ser Val Ala Ser Ala Ala Phe Val Ala Leu
            500                 505                 510

Leu Phe
```

<210> SEQ ID NO 6
<211> LENGTH: 7204
<212> TYPE: DNA
<213> ORGANISM: artificial
<220> FEATURE:
<223> OTHER INFORMATION: pHH-VSG3-G4S-Hyg plasmid DNA sequence -continued

<400> SEQUENCE: 6

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
ccgatatcga aggcagcgga aagtgtgcca atgcatttta aatgacagat ttattttatt    480
aaaaatgaga acacttagaa tatttcatgt cgattcaagc tagcagtaat atgccagtaa    540
atagtttcca tttacaagca caatttcatc ctccttacgt gattctgtag catttagttc    600
aagaaaaagc aataaaagaa ttcggagacg aagagccggt tagattgcat ttggacaccg    660
ctatacatat gttaagacac acaagcattc tatacgtaaa agatctagta tataggagca    720
acgctctgcc aaaacataat ggcaagacaa acggccgtgt ttgccgctga tgctacagaa    780
ccagcttaat ttccagaaga cgaaaatttg catgttttcc cacaatattt taattactct    840
tgaagattgt agttattcct acgcgacacg tacgcggcat gcaagcggca gcactgcttt    900
tattagtttt gcgcgcaata accagcatcg aagctgcagc cggtggcggt ggctcaggtg    960
gtggcggttc aggcggtggt ggctcagatg acgtcaatcc agatgacaac aaggaagact   1020
ttgcagtctt gtgcgcacta gctgcgctgg ccaacctcca gaccacggtg ccctcaatag   1080
acacgtcagg acttgcagcc tacgacaact tgcaacagct caacctaagc ctaagcagca   1140
aagaatggaa aagcctgttc aacaaagcgg ctgactcaaa cggatctccc aagcagccgc   1200
cggaaggatt tcaatcggac cctacttggc ggaagcagtg gcctatatgg gtaacagcag   1260
cagcagcatt aaaggccgaa aacaaagagg cagctgtcct agcgagggcg ggactaacaa   1320
acgcgccaga ggaactcaga aacagggccc ggctggcgct aataccctta ttagcccaag   1380
ccgagcaaat ccgggaccgg ctcagtgaaa tacaaaaaca aaacgaagac acgacaccaa   1440
cggcaatagc gaaggcactt aataaagccg tctacggcca ggacaaagaa acgggcgcgg   1500
tgtacaattc agcggattgc ttcagcggta acgttgcaga ctcaacccaa aactcctgca   1560
aagccgggaa ccaagcctcc aaagcgacga cagtagccgc aacgatagtt tgtgtttgcc   1620
acaaaaaaaa cggcggcaac gacgccgcaa acgcctgcgg tagactgatt aatcaccaat   1680
ccgacgctgg tgccaaccta gccaccgcca gctcagactt cggcgacata attgctacat   1740
gcgcagctcg cccgccaaaa ccattgaccg ctgcctatct agacagcgca ctagccgcgg   1800
tgagcgcgag gataaggttc aaaaacggca acggttacct gggcaaattc aaagcgacag   1860
gctgcacagg cgccgcaagt gaaggcttat gtgtcgaata cactgcccta acagcggcaa   1920
cgatgcaaaa tttttacaaa atcccgtggg taaaggagat ctcaaacgta gcggaagccc   1980
taaagaggac agaaaaagac gcagcagaat caacactgtt aagcacttgg cttaaagcca   2040
gcgaaaacca aggaaatagc gtcgctcaga agcttataaa ggtaggagac agcaaagcgg   2100
taccaccggc acagcgacag acacaaaata agccaggatc aaactgcaat aagaacctta   2160
aaaaaagcga atgcaaagac agtgatggtt gcaaatggaa caggactgag gagaccgaag   2220
gtgatttctg caaacctaaa gagacaggaa cagaaaaccc agcagcagga acaggagagg   2280
gagctgcagg agcaaatacg gaaaccaaaa agtgctcaga taagaaaact gaaggcgact   2340
```

```
gcaaagatgg atgcaaatgg gatggaaaag aatgcaaaga ttcctctatt ctagcaacca   2400
agaaattcgc cctcaccgtg gtttctgctg catttgtggc cttgcttttt taatttcccc   2460
cctcaaattt cccccctcct tttaaaattt tccttgctac ttgaaaactt tttgatatat   2520
tttaacacca aaaccagccg agattttgtg ttctgtgttt tgtaagttga ctgtctgatt   2580
gtctagaaat attttctggc aactaaaatt tttttctttt ttcctgtttt ttttgtaggt   2640
aggtaggaat gggggggggg gggtagttag gtaggttagt taggttagtt agggggttag   2700
ttaggggggt taggcttagg attaggcaca gcaaggtctt ctgaaattca tgtttttttt   2760
tttttactc tgcattgcag tctccgctct tatttagttt tgctttacgt aaggtctcgt   2820
tgctgccata aaataagcta ctagtagctt accatgaaaa agcctgaact caccgcgacg   2880
tctgtcgaga agtttctgat cgaaaagttc gacagcgtct ccgacctgat gcagctctcg   2940
gagggcgaag aatctcgtgc tttcagcttc gatgtaggag ggcgtggata tgtcctgcgg   3000
gtaaatagct gcgccgatgg tttctacaaa gatcgttatg tttatcggca ctttgcatcg   3060
gccgcgctcc cgattccgga agtgcttgac attggggaat tcagcgagag cctgacctat   3120
tgcatctccc gccgtgcaca gggtgtcacg ttgcaagacc tgcctgaaac cgaactgccc   3180
gctgttctgc agccggtcgc ggaggccatg gatgcgatcg ctgcggccga tcttagccag   3240
acgagcgggt tcggcccatt cggaccgcaa ggaatcggtc aatacactac atggcgtgat   3300
ttcatatgcg cgattgctga tccccatgtg tatcactggc aaactgtgat ggacgacacc   3360
gtcagtgcgt ccgtcgcgca ggctctcgat gagctgatgc tttgggccga ggactgcccc   3420
gaagtccggc acctcgtgca cgcggatttc ggctccaaca atgtcctgac ggacaatggc   3480
cgcataacag cggtcattga ctggagcgag gcgatgttcg gggattccca atacgaggtc   3540
gccaacatct tcttctggag gccgtggttg gcttgtatgg agcagcagac gcgctacttc   3600
gagcggaggc atccggagct tgcaggatcg ccgcggctcc gggcgtatat gctccgcatt   3660
ggtcttgacc aactctatca gagcttggtt gacggcaatt tcgatgatgc agcttgggcg   3720
cagggtcgat gcgacgcaat cgtccgatcc ggagccggga ctgtcgggcg tacacaaatc   3780
gcccgcagaa gcgcggccgt ctggaccgat ggctgtgtag aagtactcgc cgatagtgga   3840
aaccgacgcc ccagcactcg tccgagggca aaggaatagg gatcgatcct gcccatttag   3900
ttagttggct tttcccttgt ctcgtgtctt ttccgtggaa aggttcccgg agtaatctga   3960
tggcacagca gggaggtgcg cctgcaggtt ggttaggaag gggggatgat gtaaaagaag   4020
aaaatggggg gatattagac ttaggcttag gattaggatt aggattagga ttagggttaa   4080
ttttttcctc ttttttttta actcacacct ctatcctgga tttttaattt ttttttttag   4140
ccattcgcgg ctcctttttt tttttttgcg ccaatgttta atttttttatt gtgttttcaa   4200
tttttttgtc aaccatgcag cggctgtttt gttatgcgga ccctaaccct cctccccccc   4260
ccccgcccgc gcacctccat ttttaaaaat ttttttaccg cgtccttcaa ccagaatttt   4320
tttaaatttt ttaatttttt ttattttccg tggttttgaa tcttaatttt tcgacggcat   4380
gcccgctact ctttttttggc tttttgtttt ttcgtttttt tttgacgacg ccttttttta   4440
aatttctttt cctcgatttt tttcgttcat tttttttggt ttagtattca ttttttgaac   4500
tttagttttg catttaaatt tttaacgggt ttttgcttac attttttttt tacatcctct   4560
ttttcttttt gctttttagt tttcgacatt tttcagattt ttttcttttt tgaatttttt   4620
ttttgttaca accaggcatc gtttttttttg gcggcgcccc tttttggtaa caccggcggc   4680
```

-continued

```
cacggtgttt cggattaagg ccgcgggaat tcgattaggg ttagggttag ggttagggtt   4740
agggttaggg ttagggttag ggttagggtt agggttaggg ttagggttag ggttagggtt   4800
agggttaggg ttagggttag ggttagggtt agggttaggg ttagggttag ggttagggtt   4860
agggttaggg ttagggttag ggttagggtt agggttaggg ttagggttag ggttaatcac   4920
tagctagtgg atccgatatc tctagagtcg acctgcaggc atgcaagctt ggcgtaatca   4980
tggtcatagc tgtttcctgt gtgaaattgt tatccgctca caattccaca caacatacga   5040
gccggaagca taaagtgtaa agcctggggt gcctaatgag tgagctaact cacattaatt   5100
gcgttgcgct cactgcccgc tttccagtcg ggaaacctgt cgtgccagct gcattaatga   5160
atcggccaac gcgcggggag aggcggtttg cgtattgggc gctcttccgc ttcctcgctc   5220
actgactcgc tgcgctcggt cgttcggctg cggcgagcgg tatcagctca ctcaaaggcg   5280
gtaatacggt tatccacaga atcaggggat aacgcaggaa agaacatgtg agcaaaaggc   5340
cagcaaaagg ccaggaaccg taaaaaggcc gcgttgctgg cgtttttcca taggctccgc   5400
cccccctgacg agcatcacaa aaatcgacgc tcaagtcaga ggtggcgaaa cccgacagga   5460
ctataaagat accaggcgtt tccccctgga agctccctcg tgcgctctcc tgttccgacc   5520
ctgccgctta ccggatacct gtccgccttt ctcccttcgg gaagcgtggc gctttctcat   5580
agctcacgct gtaggtatct cagttcggtg taggtcgttc gctccaagct gggctgtgtg   5640
cacgaacccc ccgttcagcc cgaccgctgc gccttatccg gtaactatcg tcttgagtcc   5700
aacccggtaa gacacgactt atcgccactg gcagcagcca ctggtaacag gattagcaga   5760
gcgaggtatg taggcggtgc tacagagttc ttgaagtggt ggcctaacta cggctacact   5820
agaagaacag tatttggtat ctgcgctctg ctgaagccag ttaccttcgg aaaaagagtt   5880
ggtagctctt gatccggcaa acaaaccacc gctggtagcg gtggtttttt tgtttgcaag   5940
cagcagatta cgcgcagaaa aaaaggatct caagaagatc ctttgatctt ttctacgggg   6000
tctgacgctc agtggaacga aaactcacgt taagggattt tggtcatgag attatcaaaa   6060
aggatcttca cctagatcct tttaaattaa aaatgaagtt ttaaatcaat ctaaagtata   6120
tatgagtaaa cttggtctga cagttaccaa tgcttaatca gtgaggcacc tatctcagcg   6180
atctgtctat ttcgttcatc catagttgcc tgactccccg tcgtgtagat aactacgata   6240
cgggagggct taccatctgg ccccagtgct gcaatgatac cgcgagaccc acgctcaccg   6300
gctccagatt tatcagcaat aaaccagcca gccggaaggg ccgagcgcag aagtggtcct   6360
gcaactttat ccgcctccat ccagtctatt aattgttgcc gggaagctag agtaagtagt   6420
tcgccagtta atagtttgcg caacgttgtt gccattgcta caggcatcgt ggtgtcacgc   6480
tcgtcgtttg gtatggcttc attcagctcc ggttcccaac gatcaaggcg agttacatga   6540
tcccccatgt tgtgcaaaaa agcggttagc tccttcggtc ctccgatcgt tgtcagaagt   6600
aagttggccg cagtgttatc actcatggtt atggcagcac tgcataattc tcttactgtc   6660
atgccatccg taagatgctt ttctgtgact ggtgagtact caaccaagtc attctgagaa   6720
tagtgtatgc ggcgaccgag ttgctcttgc ccggcgtcaa tacgggataa taccgcgcca   6780
catagcagaa ctttaaaagt gctcatcatt ggaaaacgtt cttcggggcg aaaactctca   6840
aggatcttac cgctgttgag atccagttcg atgtaaccca ctcgtgcacc caactgatct   6900
tcagcatctt ttactttcac cagcgtttct gggtgagcaa aaacaggaag gcaaaatgcc   6960
gcaaaaaagg gaataagggc gacacggaaa tgttgaatac tcatactctt cctttttcaa   7020
tattattgaa gcatttatca gggttattgt ctcatgagcg gatacatatt tgaatgtatt   7080
```

tagaaaaata aacaaatagg ggttccgcgc acatttcccc gaaaagtgcc acctgacgtc 7140
taagaaacca ttattatcat gacattaacc tataaaaata ggcgtatcac gaggcccttt 7200
cgtc 7204

<210> SEQ ID NO 7
<211> LENGTH: 7219
<212> TYPE: DNA
<213> ORGANISM: Artificial
<220> FEATURE:
<223> OTHER INFORMATION: pHH-ILTat1.24-G4S-Hyg plasmid DNA sequence

<400> SEQUENCE: 7
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggat 420
ccgatatcga aggcagcgga aagtgtgcca atgcatttta aatgacagat ttattttatt 480
aaaaatgaga acacttagaa tatttcatgt cgattcaagc tagcagtaat atgccagtaa 540
atagtttcca tttacaagca caatttcatc ctccttacgt gattctgtag catttagttc 600
aagaaaaagc aataaaagaa ttcggagacg aagagccggt tagattgcat ttggacaccg 660
ctatacatat gttaagacac acaagcattc tatacgtaaa agatctagta tataggagca 720
acgctctgcc aaaacataat ggcaagacaa acggccgtgt ttgccgctga tgctacagaa 780
ccagcttaat ttccagaaga cgaaaatttg catgttttcc cacaatattt taattactct 840
tgaagattgt agttattcct acgcgacacg tacgcggcat ggtatacaga aatatactgc 900
aattaagcgt cctaaaagta ctacttatag tgcttatagt ggaagcaggt ggcggtggct 960
caggtggtgg cggttcaggc ggtggtggct caacgcactt cggtgtaaaa tacgagctct 1020
ggcagccaga atgcgaactg acagcggaat tgcggaaaac tgcaggggtg gcaaaaatga 1080
aagttaatag cgatttgaac tcctttaaaa cgcttgaact cacaaagatg aaattgctaa 1140
ccttcgccgc aaaatttccc gaaagcaaag aggcactaac gttacgcgct ctagaagcgg 1200
cactaaacac tgatctacga gcactacgag ataatatagc aaatggcatc gacagggctg 1260
tccgggcaac agcgtacgca tcagaggcgg caggcgcttt attttctggc atacagacgc 1320
tccatgacgc caccgacggc acgacctatt gccttagcgc aagcgggcaa ggatccaacg 1380
gcaacgctgc aatggcatca cagggctgca aaccactagc gttaccagaa cttctaacag 1440
aagactcata caacaccgac gttatatcgg acaaagggtt cccgaagatt tcgccactaa 1500
caaatgccca aggacagggc aaaagcggcg aatgcggcct ttttcaagcc gcaagcggcg 1560
ctcaggcgac aaacacaggt gtgcagttct cagggggcag caggataaac ttaggccttg 1620
gcgccatagt agcaagcgca gcccagcagc cgacacgccc ggacctaagt gatttttccg 1680
gcacagcacg aaaccaagca gatacgctct acggcaaagc acatgcttcc atcacagagt 1740
tactgcagct cgcacagggg ccgaaaccag gacagaccga agtagaaaca atgaagcttc 1800
tagcacaaaa gacagcggca ttggacagca tcaagttcca actagcagca agcacaggaa 1860

-continued

```
agaaaacatc agactacaaa gaagacgaaa acttgaaaac ggaatacttt ggaaagacag   1920
aaagcaatat agaagcactt tggaacaaag taaaggaaga gaaagtgaaa ggagccgacc   1980
cggaggaccc aagcaaggag tccaagatta gtgacctcaa caccgaagag cagcttcaga   2040
gagttttaga ttactacgca gtggctacaa tgttaaagtt agctaaacaa gcggaggata   2100
ttgcaaaact cgaaactgaa atagcggatc aaagaggcaa atccccagaa gccgaatgca   2160
ataaaataac cgaggaaccc aaatgcagcg aggaaaagat ttgcagttgg cataaggagg   2220
ttaaagcggg agaaaagaac tgccaattta actcaacaaa agcctcaaaa agtggtgtgc   2280
ctgtaacaca aactcaaact gcaggagccg acacgacagc agaaaagtgc aaaggcaaag   2340
gagagaaaga ttgcaaatct ccggattgca aatgggaggg cggaacttgc aaagattcct   2400
ctattctagc aaacaaacaa tttgccctca gcgtggcttc tgccgcattt gtggccttgc   2460
ttttctaatt tccccctca aatttccccc ctccttttaa aattttcctt gctacttgaa   2520
aactttttga tatattttaa caccaaaacc agccgagatt ttgtgttctg tgttttgtaa   2580
gttgactgtc tgattgtcta gaaatatttt ctggcaacta aaattttttt ctttttttcct  2640
gtttttttg taggtaggta ggaatggggg gggggggta gttaggtagg ttagttaggt   2700
tagttagggg gttagttagg ggggttaggc ttaggattag gcacagcaag gtcttctgaa   2760
attcatgttt ttttttttt tactctgcat tgcagtctcc gctcttattt agttttgctt   2820
tacgtaaggt ctcgttgctg ccataaaata agctactagt agcttaccat gaaaaagcct   2880
gaactcaccg cgacgtctgt cgagaagttt ctgatcgaaa agttcgacag cgtctccgac   2940
ctgatgcagc tctcggaggg cgaagaatct cgtgctttca gcttcgatgt aggagggcgt   3000
ggatatgtcc tgcgggtaaa tagctgcgcc gatggtttct acaaagatcg ttatgtttat   3060
cggcactttg catcggccgc gctcccgatt ccggaagtgc ttgacattgg ggaattcagc   3120
gagagcctga cctattgcat ctcccgccgt gcacagggtg tcacgttgca agacctgcct   3180
gaaaccgaac tgcccgctgt tctgcagccg gtcgcggagg ccatggatgc gatcgctgcg   3240
gccgatctta gccagacgag cgggttcggc ccattcggac cgcaaggaat cggtcaatac   3300
actacatggc gtgatttcat atgcgcgatt gctgatcccc atgtgtatca ctggcaaact   3360
gtgatggacg acaccgtcag tgcgtccgtc gcgcaggctc tcgatgagct gatgctttgg   3420
gccgaggact gccccgaagt ccggcacctc gtgcacgcgg atttcggctc caacaatgtc   3480
ctgacggaca atggccgcat aacagcggtc attgactgga gcgaggcgat gttcggggat   3540
tcccaatacg aggtcgccaa catcttcttc tggaggccgt ggttggcttg tatggagcag   3600
cagacgcgct acttcgagcg gaggcatccg gagcttgcag gatcgccgcg gctccgggcg   3660
tatatgctcc gcattggtct tgaccaactc tatcagagct tggttgacgg caatttcgat   3720
gatgcagctt gggcgcaggg tcgatgcgac gcaatcgtcc gatccggagc cgggactgtc   3780
gggcgtacac aaatcgcccg cagaagcgcg gccgtctgga ccgatggctg tgtagaagta   3840
ctcgccgata gtggaaaccg acgccccagc actcgtccga gggcaaagga atagggatcg   3900
atcctgccca tttagttagt tggcttttcc cttgtctcgt gtcttttccg tggaaaggtt   3960
cccggagtaa tctgatggca cagcagggag gtgcgcctgc aggttggtta ggaagggggg   4020
atgatgtaaa agaagaaaat ggggggatat tagacttagg cttaggatta ggattaggat   4080
taggattagg gttaattttt tcctctttt ttttaactca cacctctatc ctggattttt   4140
aattttttttt tttagccatt cgcggctcct tttttttttt ttgcgccaat gtttaatttt  4200
ttattgtgtt ttcaattttt ttgtcaacca tgcagcggct gttttgttat gcggacccta   4260
```

-continued

```
accctcctcc ccccccccg cccgcgcacc tccattttta aaaattttt taccgcgtcc   4320
ttcaaccaga attttttaa atttttaat tttttttatt ttccgtggtt ttgaatctta   4380
atttttcgac ggcatgcccg ctactctttt ttggcttttt gtttttcgt ttttttttga   4440
cgacgccttt ttttaaattt cttttcctcg atttttttcg ttcatttttt ttggtttagt   4500
attcattttt tgaactttag ttttgcattt aaatttttaa cgggtttttg cttacatttt   4560
tttttacat cctctttttc tttttgcttt ttagttttcg acatttttca gatttttttc   4620
tttttgaat ttttttttg ttacaaccag gcatcgtttt ttttggcggc gcccctttt   4680
ggtaacaccg gcggccacgg tgtttcggat taaggccgcg ggaattcgat tagggttagg   4740
gttagggtta gggttagggt tagggttagg gttagggtta gggttagggt tagggttagg   4800
gttagggtta gggttagggt tagggttagg gttagggtta gggttagggt tagggttagg   4860
gttagggtta gggttagggt tagggttagg gttagggtta gggttagggt tagggttagg   4920
gttagggtta atcactagct agtggatccg atatctctag agtcgacctg caggcatgca   4980
agcttggcgt aatcatggtc atagctgttt cctgtgtgaa attgttatcc gctcacaatt   5040
ccacacaaca tacgagccgg aagcataaag tgtaaagcct ggggtgccta atgagtgagc   5100
taactcacat taattgcgtt gcgctcactg cccgctttcc agtcgggaaa cctgtcgtgc   5160
cagctgcatt aatgaatcgg ccaacgcgcg gggagaggcg gtttgcgtat tgggcgctct   5220
tccgcttcct cgctcactga ctcgctgcgc tcggtcgttc ggctgcggcg agcggtatca   5280
gctcactcaa aggcggtaat acggttatcc acagaatcag gggataacgc aggaaagaac   5340
atgtgagcaa aaggccagca aaaggccagg aaccgtaaaa aggccgcgtt gctggcgttt   5400
ttccataggc tccgcccccc tgacgagcat cacaaaaatc gacgctcaag tcagaggtgg   5460
cgaaacccga caggactata aagataccag gcgtttcccc ctggaagctc cctcgtgcgc   5520
tctcctgttc cgaccctgcc gcttaccgga tacctgtccg cctttctccc ttcgggaagc   5580
gtggcgcttt ctcatagctc acgctgtagg tatctcagtt cggtgtaggt cgttcgctcc   5640
aagctgggct gtgtgcacga accccccgtt cagcccgacc gctgcgcctt atccggtaac   5700
tatcgtcttg agtccaaccc ggtaagacac gacttatcgc cactggcagc agccactggt   5760
aacaggatta gcagagcgag gtatgtaggc ggtgctacag agttcttgaa gtggtggcct   5820
aactacggct acactagaag aacagtattt ggtatctgcg ctctgctgaa gccagttacc   5880
ttcggaaaaa gagttggtag ctcttgatcc ggcaaacaaa ccaccgctgg tagcggtggt   5940
tttttgttt gcaagcagca gattacgcgc agaaaaaaag gatctcaaga agatcctttg   6000
atcttttcta cggggtctga cgctcagtgg aacgaaaact cacgttaagg gattttggtc   6060
atgagattat caaaaaggat cttcacctag atccttttaa attaaaaatg aagttttaaa   6120
tcaatctaaa gtatatatga gtaaacttgg tctgacagtt accaatgctt aatcagtgag   6180
gcacctatct cagcgatctg tctatttcgt tcatccatag ttgcctgact ccccgtcgtg   6240
tagataacta cgatacggga gggcttacca tctggcccca gtgctgcaat gataccgcga   6300
gacccacgct caccggctcc agatttatca gcaataaacc agccagccgg aagggccgag   6360
cgcagaagtg gtcctgcaac tttatccgcc tccatccagt ctattaattg ttgccgggaa   6420
gctagagtaa gtagttcgcc agttaatagt ttgcgcaacg ttgttgccat tgctacaggc   6480
atcgtggtgt cacgctcgtc gtttggtatg gcttcattca gctccggttc ccaacgatca   6540
aggcgagtta catgatcccc catgttgtgc aaaaaagcgg ttagctcctt cggtcctccg   6600
```

-continued

```
atcgttgtca gaagtaagtt ggccgcagtg ttatcactca tggttatggc agcactgcat   6660

aattctctta ctgtcatgcc atccgtaaga tgcttttctg tgactggtga gtactcaacc   6720

aagtcattct gagaatagtg tatgcggcga ccgagttgct cttgcccggc gtcaatacgg   6780

gataataccg cgccacatag cagaacttta aaagtgctca tcattggaaa acgttcttcg   6840

gggcgaaaac tctcaaggat cttaccgctg ttgagatcca gttcgatgta acccactcgt   6900

gcacccaact gatcttcagc atcttttact ttcaccagcg tttctgggtg agcaaaaaca   6960

ggaaggcaaa atgccgcaaa aaagggaata agggcgacac ggaaatgttg aatactcata   7020

ctcttccttt ttcaatatta ttgaagcatt tatcagggtt attgtctcat gagcggatac   7080

atatttgaat gtatttagaa aaataaacaa ataggggttc cgcgcacatt tccccgaaaa   7140

gtgccacctg acgtctaaga aaccattatt atcatgacat taacctataa aaataggcgt   7200

atcacgaggc cctttcgtc                                                7219


<210> SEQ ID NO 8
<211> LENGTH: 15
<212> TYPE: PRT
<213> ORGANISM: Artificial
<220> FEATURE:
<223> OTHER INFORMATION: 4GS linker

<400> SEQUENCE: 8

Gly Gly Gly Gly Ser Gly Gly Gly Gly Ser Gly Gly Gly Gly Ser
1               5                   10                  15


<210> SEQ ID NO 9
<211> LENGTH: 524
<212> TYPE: PRT
<213> ORGANISM: Artificial
<220> FEATURE:
<223> OTHER INFORMATION: VSG3.G4S (S317A) Protein

<400> SEQUENCE: 9

Met Gln Ala Ala Ala Leu Leu Leu Leu Val Leu Arg Ala Ile Thr Ser
1               5                   10                  15

Ile Glu Ala Ala Ala Gly Gly Gly Gly Ser Gly Gly Gly Gly Ser Gly
            20                  25                  30

Gly Gly Gly Ser Asp Asp Val Asn Pro Asp Asp Asn Lys Glu Asp Phe
        35                  40                  45

Ala Val Leu Cys Ala Leu Ala Ala Leu Ala Asn Leu Gln Thr Thr Val
    50                  55                  60

Pro Ser Ile Asp Thr Ser Gly Leu Ala Ala Tyr Asp Asn Leu Gln Gln
65                  70                  75                  80

Leu Asn Leu Ser Leu Ser Ser Lys Glu Trp Lys Ser Leu Phe Asn Lys
                85                  90                  95

Ala Ala Asp Ser Asn Gly Ser Pro Lys Gln Pro Pro Glu Gly Phe Gln
            100                 105                 110

Ser Asp Pro Thr Trp Arg Lys Gln Trp Pro Ile Trp Val Thr Ala Ala
        115                 120                 125

Ala Ala Leu Lys Ala Glu Asn Lys Glu Ala Ala Val Leu Ala Arg Ala
    130                 135                 140

Gly Leu Thr Asn Ala Pro Glu Glu Leu Arg Asn Arg Ala Arg Leu Ala
145                 150                 155                 160

Leu Ile Pro Leu Leu Ala Gln Ala Glu Gln Ile Arg Asp Arg Leu Ser
                165                 170                 175

Glu Ile Gln Lys Gln Asn Glu Asp Thr Thr Pro Thr Ala Ile Ala Lys
```

-continued

```
            180                 185                 190

Ala Leu Asn Lys Ala Val Tyr Gly Gln Asp Lys Glu Thr Gly Ala Val
        195                 200                 205

Tyr Asn Ser Ala Asp Cys Phe Ser Gly Asn Val Ala Asp Ser Thr Gln
    210                 215                 220

Asn Ser Cys Lys Ala Gly Asn Gln Ala Ser Lys Ala Thr Thr Val Ala
225                 230                 235                 240

Ala Thr Ile Val Cys Val Cys His Lys Lys Asn Gly Gly Asn Asp Ala
                245                 250                 255

Ala Asn Ala Cys Gly Arg Leu Ile Asn His Gln Ser Asp Ala Gly Ala
            260                 265                 270

Asn Leu Ala Thr Ala Ser Ser Asp Phe Gly Asp Ile Ile Ala Thr Cys
        275                 280                 285

Ala Ala Arg Pro Pro Lys Pro Leu Thr Ala Ala Tyr Leu Asp Ser Ala
    290                 295                 300

Leu Ala Ala Val Ser Ala Arg Ile Arg Phe Lys Asn Gly Asn Gly Tyr
305                 310                 315                 320

Leu Gly Lys Phe Lys Ala Thr Gly Cys Thr Gly Ala Ala Ser Glu Gly
                325                 330                 335

Leu Cys Val Glu Tyr Thr Ala Leu Thr Ala Ala Thr Met Gln Asn Phe
            340                 345                 350

Tyr Lys Ile Pro Trp Val Lys Glu Ile Ser Asn Val Ala Glu Ala Leu
        355                 360                 365

Lys Arg Thr Glu Lys Asp Ala Ala Glu Ser Thr Leu Leu Ser Thr Trp
    370                 375                 380

Leu Lys Ala Ser Glu Asn Gln Gly Asn Ser Val Ala Gln Lys Leu Ile
385                 390                 395                 400

Lys Val Gly Asp Ser Lys Ala Val Pro Pro Ala Gln Arg Gln Thr Gln
                405                 410                 415

Asn Lys Pro Gly Ser Asn Cys Asn Lys Asn Leu Lys Lys Ser Glu Cys
            420                 425                 430

Lys Asp Ser Asp Gly Cys Lys Trp Asn Arg Thr Glu Glu Thr Glu Gly
        435                 440                 445

Asp Phe Cys Lys Pro Lys Glu Thr Gly Thr Glu Asn Pro Ala Ala Gly
    450                 455                 460

Thr Gly Glu Gly Ala Ala Gly Ala Asn Thr Glu Thr Lys Lys Cys Ser
465                 470                 475                 480

Asp Lys Lys Thr Glu Gly Asp Cys Lys Asp Gly Cys Lys Trp Asp Gly
                485                 490                 495

Lys Glu Cys Lys Asp Ser Ser Ile Leu Ala Thr Lys Lys Phe Ala Leu
            500                 505                 510

Thr Val Val Ser Ala Ala Phe Val Ala Leu Leu Phe
        515                 520


<210> SEQ ID NO 10
<211> LENGTH: 488
<212> TYPE: PRT
<213> ORGANISM: Artificial
<220> FEATURE:
<223> OTHER INFORMATION: VSG2-1DK Protein

<400> SEQUENCE: 10

Met Pro Ser Asn Gln Glu Ala Arg Leu Phe Leu Ala Val Leu Val Leu
1               5                   10                  15

Ala Gln Val Leu Pro Ile Leu Val Asp Ser Ala Ala Gly Gly Gly Glu
```

-continued

```
            20                  25                  30

Asn Leu Tyr Phe Gln Gly Gly Gly Gly Gly Gly Phe Lys Gln Ala Phe
        35                  40                  45

Trp Gln Pro Leu Cys Gln Val Ser Glu Glu Leu Asp Asp Gln Pro Lys
    50                  55                  60

Gly Ala Leu Phe Thr Leu Gln Ala Ala Ala Ser Lys Ile Gln Lys Met
65                  70                  75                  80

Arg Asp Ala Ala Leu Arg Ala Ser Ile Tyr Ala Glu Ile Asn His Gly
                85                  90                  95

Thr Asn Arg Ala Lys Ala Ala Val Ile Val Ala Asn His Tyr Ala Met
            100                 105                 110

Lys Ala Asp Ser Gly Leu Glu Ala Leu Lys Gln Thr Leu Ser Ser Gln
        115                 120                 125

Glu Val Thr Ala Thr Ala Thr Ala Ser Tyr Leu Lys Gly Arg Ile Asp
    130                 135                 140

Glu Tyr Leu Asn Leu Leu Leu Gln Thr Lys Glu Ser Gly Thr Ser Gly
145                 150                 155                 160

Cys Met Met Asp Thr Ser Gly Thr Asn Thr Val Thr Lys Ala Gly Gly
                165                 170                 175

Thr Ile Gly Gly Val Pro Cys Lys Leu Gln Leu Ser Pro Ile Gln Pro
            180                 185                 190

Lys Arg Pro Ala Ala Thr Tyr Leu Gly Lys Ala Gly Tyr Val Gly Leu
        195                 200                 205

Thr Arg Gln Ala Asp Ala Ala Asn Asn Phe His Asp Asn Asp Ala Glu
    210                 215                 220

Cys Arg Leu Ala Ser Gly His Asn Thr Asn Gly Leu Gly Lys Ser Gly
225                 230                 235                 240

Gln Leu Ser Ala Ala Val Thr Met Ala Ala Gly Tyr Val Thr Val Ala
                245                 250                 255

Asn Ser Gln Thr Ala Val Thr Val Gln Ala Leu Asp Ala Leu Gln Glu
            260                 265                 270

Ala Ser Gly Ala Ala His Gln Pro Trp Ile Asp Ala Trp Lys Ala Lys
        275                 280                 285

Lys Ala Leu Thr Gly Ala Glu Thr Ala Glu Phe Arg Asn Glu Thr Ala
    290                 295                 300

Gly Ile Ala Gly Lys Thr Gly Val Thr Lys Leu Val Glu Glu Ala Leu
305                 310                 315                 320

Leu Lys Lys Lys Asp Ser Glu Ala Ser Glu Ile Gln Thr Glu Leu Lys
                325                 330                 335

Lys Tyr Phe Ser Gly His Glu Asn Glu Gln Trp Thr Ala Ile Glu Lys
            340                 345                 350

Leu Ile Ser Glu Gln Pro Val Ala Gln Asn Leu Val Gly Asp Asn Gln
        355                 360                 365

Pro Thr Lys Leu Gly Glu Leu Glu Gly Asn Ala Lys Leu Thr Thr Ile
    370                 375                 380

Leu Ala Tyr Tyr Arg Met Glu Thr Ala Gly Lys Phe Glu Val Leu Thr
385                 390                 395                 400

Gln Lys His Lys Pro Ala Glu Ser Gln Gln Gln Ala Ala Glu Thr Glu
                405                 410                 415

Gly Ser Cys Asn Lys Lys Asp Gln Asn Glu Cys Lys Ser Pro Cys Lys
            420                 425                 430

Trp His Asn Asp Ala Glu Asn Lys Lys Cys Thr Leu Asp Lys Glu Glu
        435                 440                 445
```

```
Ala Lys Lys Val Ala Asp Glu Thr Ala Lys Asp Gly Lys Thr Gly Asn
    450                 455                 460

Thr Asn Thr Thr Gly Ser Ser Asn Ser Phe Val Ile Ser Lys Thr Pro
465                 470                 475                 480

Leu Trp Leu Ala Val Leu Leu Phe
                485


<210> SEQ ID NO 11
<211> LENGTH: 529
<212> TYPE: PRT
<213> ORGANISM: Artificial
<220> FEATURE:
<223> OTHER INFORMATION: ILTat1.24-G4S Protein

<400> SEQUENCE: 11

Met Val Tyr Arg Asn Ile Leu Gln Leu Ser Val Leu Lys Val Leu Leu
1               5                   10                  15

Ile Val Leu Ile Val Glu Ala Gly Gly Gly Gly Ser Gly Gly Gly Gly
            20                  25                  30

Ser Gly Gly Gly Gly Ser Thr His Phe Gly Val Lys Tyr Glu Leu Trp
        35                  40                  45

Gln Pro Glu Cys Glu Leu Thr Ala Glu Leu Arg Lys Thr Ala Gly Val
    50                  55                  60

Ala Lys Met Lys Val Asn Ser Asp Leu Asn Ser Phe Lys Thr Leu Glu
65                  70                  75                  80

Leu Thr Lys Met Lys Leu Leu Thr Phe Ala Ala Lys Phe Pro Glu Ser
                85                  90                  95

Lys Glu Ala Leu Thr Leu Arg Ala Leu Glu Ala Ala Leu Asn Thr Asp
            100                 105                 110

Leu Arg Ala Leu Arg Asp Asn Ile Ala Asn Gly Ile Asp Arg Ala Val
        115                 120                 125

Arg Ala Thr Ala Tyr Ala Ser Glu Ala Ala Gly Ala Leu Phe Ser Gly
    130                 135                 140

Ile Gln Thr Leu His Asp Ala Thr Asp Gly Thr Thr Tyr Cys Leu Ser
145                 150                 155                 160

Ala Ser Gly Gln Gly Ser Asn Gly Asn Ala Ala Met Ala Ser Gln Gly
                165                 170                 175

Cys Lys Pro Leu Ala Leu Pro Glu Leu Leu Thr Glu Asp Ser Tyr Asn
            180                 185                 190

Thr Asp Val Ile Ser Asp Lys Gly Phe Pro Lys Ile Ser Pro Leu Thr
        195                 200                 205

Asn Ala Gln Gly Gln Gly Lys Ser Gly Glu Cys Gly Leu Phe Gln Ala
    210                 215                 220

Ala Ser Gly Ala Gln Ala Thr Asn Thr Gly Val Gln Phe Ser Gly Gly
225                 230                 235                 240

Ser Arg Ile Asn Leu Gly Leu Gly Ala Ile Val Ala Ser Ala Ala Gln
                245                 250                 255

Gln Pro Thr Arg Pro Asp Leu Ser Asp Phe Ser Gly Thr Ala Arg Asn
            260                 265                 270

Gln Ala Asp Thr Leu Tyr Gly Lys Ala His Ala Ser Ile Thr Glu Leu
        275                 280                 285

Leu Gln Leu Ala Gln Gly Pro Lys Pro Gly Gln Thr Glu Val Glu Thr
    290                 295                 300

Met Lys Leu Leu Ala Gln Lys Thr Ala Ala Leu Asp Ser Ile Lys Phe
305                 310                 315                 320
```

```
Gln Leu Ala Ala Ser Thr Gly Lys Lys Thr Ser Asp Tyr Lys Glu Asp
                325                 330                 335

Glu Asn Leu Lys Thr Glu Tyr Phe Gly Lys Thr Glu Ser Asn Ile Glu
            340                 345                 350

Ala Leu Trp Asn Lys Val Lys Glu Glu Lys Val Lys Gly Ala Asp Pro
        355                 360                 365

Glu Asp Pro Ser Lys Glu Ser Lys Ile Ser Asp Leu Asn Thr Glu Glu
    370                 375                 380

Gln Leu Gln Arg Val Leu Asp Tyr Tyr Ala Val Ala Thr Met Leu Lys
385                 390                 395                 400

Leu Ala Lys Gln Ala Glu Asp Ile Ala Lys Leu Glu Thr Glu Ile Ala
                405                 410                 415

Asp Gln Arg Gly Lys Ser Pro Glu Ala Glu Cys Asn Lys Ile Thr Glu
            420                 425                 430

Glu Pro Lys Cys Ser Glu Glu Lys Ile Cys Ser Trp His Lys Glu Val
        435                 440                 445

Lys Ala Gly Glu Lys Asn Cys Gln Phe Asn Ser Thr Lys Ala Ser Lys
    450                 455                 460

Ser Gly Val Pro Val Thr Gln Thr Gln Thr Ala Gly Ala Asp Thr Thr
465                 470                 475                 480

Ala Glu Lys Cys Lys Gly Lys Gly Glu Lys Asp Cys Lys Ser Pro Asp
                485                 490                 495

Cys Lys Trp Glu Gly Gly Thr Cys Lys Asp Ser Ser Ile Leu Ala Asn
            500                 505                 510

Lys Gln Phe Ala Leu Ser Val Ala Ser Ala Ala Phe Val Ala Leu Leu
        515                 520                 525

Phe


<210> SEQ ID NO 12
<211> LENGTH: 5
<212> TYPE: PRT
<213> ORGANISM: Staphylococcus aureus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Leu Pro Xaa Thr Gly
1               5


<210> SEQ ID NO 13
<211> LENGTH: 5
<212> TYPE: PRT
<213> ORGANISM: Staphylococcus aureus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Leu Pro Xaa Thr Ala
1               5


<210> SEQ ID NO 14
<211> LENGTH: 10
<212> TYPE: PRT
<213> ORGANISM: artificial
<220> FEATURE:
<223> OTHER INFORMATION: sortagging donor sequence
```

-continued

```
<400> SEQUENCE: 14

Gly Gly Gly Ser Leu Pro Ser Thr Gly Gly
1               5                   10


<210> SEQ ID NO 15
<211> LENGTH: 10
<212> TYPE: PRT
<213> ORGANISM: artificial
<220> FEATURE:
<223> OTHER INFORMATION: sortagging donor sequence and the sortagging
      acceptor sequence

<400> SEQUENCE: 15

Gly Gly Gly Ser Leu Pro Ser Thr Ala Ala
1               5                   10


<210> SEQ ID NO 16
<211> LENGTH: 7
<212> TYPE: PRT
<213> ORGANISM: artificial
<220> FEATURE:
<223> OTHER INFORMATION: part of sortase donor sequence

<400> SEQUENCE: 16

Ser Leu Pro Ser Thr Gly Gly
1               5


<210> SEQ ID NO 17
<211> LENGTH: 7
<212> TYPE: PRT
<213> ORGANISM: artificial
<220> FEATURE:
<223> OTHER INFORMATION: sortagging linker sequence

<400> SEQUENCE: 17

Ser Leu Pro Ser Thr Ala Ala
1               5
```

VSG-BASED VACCINATION AND ANTIBODY GENERATION PLATFORM FOR THE TREATMENT OF DISEASES

CROSS-REFERENCE TO RELATED APPLICATIONS

This application is a U.S. National Phase of International PCT Application No. PCT/EP2019/079063 filed Oct. 24, 2019, which claims priority to European Patent Application No. 18202305.1 filed Oct. 24, 2018, the contents of each application are incorporated herein by reference in their entirety.

FIELD OF THE INVENTION

The invention is based on a platform for vaccination and/or antibody generation. The invention is based on the display of small molecular immunogenic compounds on the coat of variant surface glycoproteins (VSG) on trypanosomes which results in a highly effective immune response when used as a vaccine or in immunization for antibody production. The herein disclosed antigenic particles are applicable for producing antibodies or can be directly used as vaccines for the treatment of various medical conditions. Most preferably the invention relates to the VSG based vaccines specific for dependency causing substances for the treatment of addiction or avoidance of adverse events during drug abuse. Other applications include methods and uses involving the disclosed compounds and compositions for a treatment or prevention of cancer, infectious disease, contagious neurodegenerative diseases, non-communicable disorders (e.g. certain neurodegenerative diseases, allergies) and any condition or industrial use for which an immune response from vaccination or antibody use would be desirable.

DESCRIPTION

Abuse of and addiction to drugs present major problems to medical, social, and economic health, both for individuals and their families, and for society as a whole. Especially in the U.S.A. abuse of prescription opioid pain medications, such as OxyContin® and Vicodin®, has reached epidemic levels and is now a public health crisis of grave concern. In other regions (e.g., Asia, Africa and the Middle East), Tramadol abuse is on a rapid rise (UNODC World Drug Report 2017). Every facet of society has been affected by the relative availability of these drugs, their perceived safety, and the over-prescription of these drugs by medical prescribers.

The path to addiction often derives from medically sanctioned administration for pain management; however, for a substantial fraction of the population (estimated at 10-15%) this can quickly lead to addiction, followed by illicit use of prescription opioids. Of particular concern is the prevalence of illicit use of these drugs by teenagers, and the rapid increase in emergency room visits (reaching 1.2 million in 2009; DAWN report, 2010) as well as in cases of fatal overdoses resulting from abuse (with deaths from overdose, estimated at 72,000 in 2017, surpassing deaths from breast cancer for the first time, with no end in sight). Currently, treatment options are limited to supervised, mediated controlled withdrawal in rehab/detox clinics (for example using methadone or buprenorphine).

Methadone maintenance, developed at the Rockefeller University for the treatment of heroin addiction, remains the most effective and widely used pharmacotherapeutic for any addictive disease (Dole et al., 1966; Kreek, 2000). But treatment often requires years and retention rates are very poor, raising interest in additional options and/or preventatives of abuse in the first place.

One approach that has emerged for addiction is a vaccine to raise neutralizing antibodies against a particular drug target (Shen et al., 2012), an option which has been explored most extensively for cocaine (Fox et al, 1996; Shen and Kosten, 2011) and more recently for heroin derivatives (Pravetoni and colleagues, 2012, 2017 and 2018). The idea of immunotherapy to cure opioid use disorder (or at least to prevent overdose) is based on the notion that if a drug conjugated to a carrier protein can elicit a long-lasting immune response, in which antibodies directed to the chemical structure of the drug develop, then circulating antibodies can bind to the drug upon administration by the user, preventing the drug from getting to the site of action in the brain.

Although theoretically achievable, in practice, this approach suffers from a key problem: the general lack of efficient methods with which to generate neutralizing antibodies against small molecules. Thus, commonly used methods of generating antibodies against a small molecule such as cocaine, nicotine, or oxycodone (e.g. conjugation of the molecule to a carrier protein such as KLH and Tetanus Toxoid) are not particularly effective (Kantak et al., 2003). The results of the development of the cocaine vaccine, which has been brought to the clinical trials stages of development, are a good example of this (Martell et al., 2009). In a phase 2b clinical trial, the ability of conjugated cocaine as a hapten to elicit immune responses was highly variable from one individual to the next, and only 38% of the vaccinated attained useful IgG levels and they had only 2 months of adequate cocaine blockade. Furthermore, among those who did develop an immune response, the levels of antibody generated exhibited considerable variability (Martell et al., 2009).

Of more relevance to opiates, studies by Pravetoni and colleagues (2012, 2017, 2018) demonstrated the effectiveness of active immunization against oxycodone: following conjugation of oxycodone to bovine serum albumin or KLH and injection into rats, this study demonstrated a prevention through antibody binding and neutralization of low doses of oxycodone from reaching the brain, with concomitant alterations in the pharmacokinetics and potency of oxycodone in rat models of analgesia. This study provides proof of principle that when antibodies bind oxycodone, they can remove it from the bloodstream.

Together, these studies underscore the problem: namely, that while raising neutralizing antibodies to a drug of abuse is feasible, and when achieved, of major therapeutic consequence, the methods used to raise mAbs (monoclonal antibodies) against these small molecules that are drugs of abuse, are not effective.

J. Immunol. Methods. 2010 Oct 31; 362(1-2):190-4 describes the use of VSG221 (also known as VSG 427-2) as a protein platform for the display of heterologous peptide epitopes (whose sequence is genetically inserted into VSG) for antibody generation.

It is an object of the present invention to provide a vaccine and antibody generation platform that allows for a generation of vaccines and/or antibodies targeting small molecular compounds/targets. It is a further object of the invention to provide treatment options for diseases that would benefit from vaccination or other immunotherapy. A final object of the invention is to provide antibodies or other immune products generated through vaccination for industrial applications.

DETAILED DESCRIPTION OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

The problem is solved in a first aspect by an antigenic particle coated with an engineered variant surface glycoprotein (eVSG), wherein the eVSG comprises an immunogenic compound.

The term "antigenic" in context of the invention shall refer to a feature of the particle of the invention to induce a specific immune response when used as an immunogen in a vaccination or immunization procedure.

The term "variant surface glycoprotein", which is abbreviated as "VSG", refers to a family of ~60 kDa proteins which densely pack the cell surface of protozoan parasites belonging to the genus *Trypanosoma*. The parasite has a large cellular repertoire of antigenically distinct VSGs (~1500 complete and partial (pseudogenes)) which are expressed from a bloodstream expression site (BES, ES) in a polycistron by RNA polymerase I (recruited to a ribosomal-type promoter) with other ES-associated genes (ESAGs), of which transferrin receptor (Tfr: ESAG6, ESAG7) is one. Only one VSG gene is expressed at a time, as only one of the ~15 ES are active in a cell. VSG expression is 'switched' by homologous recombination induced by double-strand breaks of a silent basic copy gene from an array (directed by homology) into the active telomerically-located expression site. VSG annotation, protein sequences and gene sequences are derivable from public databases. A collection of VSGs of *Trypanosoma brucei brucei* (Lister 427 strain) is published in Cross G A. et al., Mol. Biochem. Parasitol. 2014 June; 195(1):59-73. Doi: 10.1016/j.molbiopara.2014.06.004. Preferred VSGs in context of the present invention are *T. brucei* VSGs, more preferably VSG1, VSG2, VSG3 or ILTat1.24. A VSG according to the invention is preferred which is characterized by an N-terminus which is located 3-dimensionally within the VSG at a position which is, when the VSG is present within a VSG coat, for example on a trypanosome cell, located sufficiently close to the accessible outer coat-surface, that the addition of a linker sequence (preferably not more than 100 amino acids, preferably not more than 50 amino acids, and most preferably not more than 20 amino acids in length) allows for modification of the so extended or not extended N-terminus of the VSG protein. Preferably any sequence that is N-terminal inserted into a VSG sequence will be inserted right before the starting methionine (M). In further embodiments the insertion is immediately downstream of the signal peptide cleavage site. Preferred VSG sequences to be used in context of the invention are the VSGs comprising an amino acid sequence according to any one shown in SEQ ID NO: 1 to SEQ ID NO: 5.

The term "engineered VSG" or "eVSG" shall refer to any VSG protein comprising an artificial modification compared to the wild-type sequence of said VSG. Preferably the eVSG is a non-naturally-occurring sequence. The VSG can be modified to become an eVSG either by post-translational modification, chemical modification, genetic engineering of the VSG coding sequence and any other means known to the skilled person for protein modification. VSGs according to the invention may be both provided as membrane located proteins or in soluble for as soluble VSGs.

The terms "immunogenic compound" or alternatively "immunogen" as used herein, encompasses any kind of compound, or structure, capable of eliciting an immune response in a host. Preferably, but not necessarily, an immunogenic compound according to the invention comprises an amino acid sequence or is a small molecular compound. A small molecule in context of the herein described invention shall be any compound having a molecular mass significantly lower than for example complex macromolecules or proteins, so preferably a small molecule has a molecular weight of less than 50 kDa, preferably less than 20 or 10 kDa.

In context of the invention the immunogenic compound is a small molecule, a nucleic acid, or a peptide.

In other embodiments the immunogenic compound is considered as a small molecule, a nucleic acid, a carbohydrate, a lipid or a peptide, or any combination of these or other chemical entities).

A preferred embodiment of the antigenic particle of the invention includes that the immunogenic compound is covalently linked, optionally via a linker, to the N-terminus of the VSG. The immunogenic compound may be linked to the VSG by any means known to the skilled artisan, including any chemical reaction, preferably click-chemistry, cross-linking, or use of biological entities such as enzymes, ligases, protein-protein interactions and the like. The term "click-chemistry" in context of the invention shall refer to chemistry tailored to generate covalent bonds quickly and reliably by joining small units comprising reactive groups together (see H. C. Kolb, M. G. Finn and K. B. Sharpless, 2001). Any variants of such approaches may be used to connect the immunogenic compound to the VSG in accordance with the invention.

In general the linking of the VSG to the immunogenic compound may include the use of any linking means or linker, which in context of the herein disclosed invention refers to the means by which the VSG and the immunogenic compound are linked or connected to form an eVSG. The one or more linkers or linking means for linking the VSG and the immunogenic compound may be any structurally suitable means to connect the two. Exemplary linkers include the use of one or more amino acids which may be used to form a peptide, in some embodiments having a modified peptide backbone, a small chemical scaffold, a biotin-streptavidin, an organic or inorganic nanoparticle, a polynucleotide sequence, peptide-nucleic acids, an organic polymer, or an immunoglobulin Fc domain. The means for linking can comprise covalent and/or noncovalent bonds. The one or more linkers can include various sequences or other structural features that provide various functions or properties. For example, the one or more linkers can contain structural elements to allow the eVSG to be derivatized.

In one preferred embodiment of the antigenic particle of the invention, the antigenic particle comprises the linker, which is an N-terminal extension of the wild-type VSG N-terminal sequence, and preferably comprises 5 to 30 amino acids, preferably 10 to 20, more preferably about 15 amino acids. The linker here is used in order to render the N-terminus of the VSG more accessible to modifications, for example using enzymes, when the VSG is provided in context of an assembled VSG coat. The linker sequence is preferably introduced into the VSG by genetic engineering the VSG coding gene. Preferably the linker is introduced immediately C-terminal to, if present, a signal peptide sequence which allows for a cell surface targeting of the VSG protein. Signal peptides are usually cleaved after export. Hence, the term "signal peptide" as used herein refers to amino-terminal amino acid residues that, when attached to a target polypeptide, permits the export of the target polypeptide from the cell and cleavage of the signal peptide. A preferred linker in accordance with the invention is a G4S linker, however, any other protein linker which essentially does not interfere with VSG folding can be used in context of the invention. A G4S linker in accordance with the herein disclosed invention may comprise a multiplicity of consecutive G4S, such as a preferred linker is a G4S linker which may have the amino acid sequence of GGGGSGGGGSGGGGS (SEQ ID NO: 8).

In an additional or alternative embodiment of the invention the VSG may include a sortase acceptor sequence of any sorts. Such a sequence is preferably attached to the N-terminus of the VSG sequence in such a way that it is coat-surface accessible by a sortase enzyme. If the eVSG sequence comprises an N-terminal linker, the sortase acceptor sequence is located at the N-terminus of the linker. Exemplary sortase acceptor sequences are di-Alanine (AA-) or di-Glycine (GG-), or any other sequence that can be used for sortase-mediated ligation.

Hence, in some embodiments of the invention the immunogenic compound is linked to the VSG preferably by using a sortase enzyme.

The term "sortase," as used herein, refers to a protein having sortase activity, i.e., an enzyme able to carry out a transpeptidation reaction conjugating the C-terminus of a protein to the N-terminus of a protein via transamidation. The term includes full-length sortase proteins, e.g., full-length naturally-occurring sortase proteins, fragments of such sortase proteins that have sortase activity, modified (e.g., mutated) variants or derivatives of such sortase proteins or fragments thereof, as well as proteins that are not derived from a naturally occurring sortase protein, but exhibit sortase activity. Those of skill in the art will readily be able to determine whether or not a given protein or protein fragment exhibits sortase activity, e.g., by contacting the protein or protein fragment in question with a suitable sortase substrate under conditions allowing transpeptidation and determining whether the respective transpeptidation reaction product is formed.

Suitable sortases will be apparent to those of skill in the art and include, but are not limited to, sortase A, sortase B, sortase C, and sortase D type sortases. Suitable sortases are described, for example, in Dramsi S, Trieu-Cuot P, Bierne H, Sorting sortases: a nomenclature proposal for the various sortases of Gram-positive bacteria. Res. Microbiol. 156(3): 289-97, 2005; Comfort D, Clubb R T. A comparative genome analysis identifies distinct sorting pathways in gram-positive bacteria. Infect Immun., 72(5):2710-22, 2004; Chen I, Dorr B M, and Liu D R., A general strategy for the evolution of bond-forming enzymes using yeast display. Proc Natl Acad. Sci. USA. 2011 Jul. 12; 108(28):11399; and Pallen, M. J.; Lam, A. C.; Antonio, M.; Dunbar, K. TRENDS in Microbiology, 2001, 9(3), 97-101; the entire contents of each of which are incorporated herein by reference). Any known sortase can be used as a starting enzyme in an evolution strategy provided herein, and the invention is not limited in this respect. For example, the present invention encompasses embodiments relating to a sortase A from any bacterial species or strain. Those of skill in the art will appreciate that any sortase and any sortase recognition motif can be used in some embodiments of this invention, including, but not limited to, the sortases and sortase recognition motifs described in Ploegh et al., International PCT Patent Application, PCT/US2010/000274, filed Feb. 1, 2010, published as WO 2010/087994 on Aug. 5, 2010; Ploegh et al., International Patent Application PCT/US2011/033303, filed Apr. 20, 2011, published as WO 2011/133704 on Oct. 27, 2011; Liu et al., U.S. provisional Patent Application 61/662,606, filed on Jun. 21, 2012; and Liu et al., U.S. provisional Patent Application 61/880,515, filed on Sep. 20, 2013; the entire contents of each of which are incorporated herein by reference. The invention is not limited in this respect.

The term "sortase substrate," as used herein refers to a molecule or entity that can be utilized in a sortase-mediated transpeptidation reaction. Typically, a sortase utilizes two substrates—a substrate comprising a C-terminal sortase recognition motif, and a second substrate comprising an N-terminal sortase recognition motif and the transpeptidation reaction results in a conjugation of both substrates via a covalent bond. In context of the invention the "C-terminal sortase recognition motif" is also referred to as "sortagging donor sequence", whereas the term "N-terminal sortase recognition motif" is referred to as "sortagging acceptor sequence". In preferred embodiments, the C-terminal and N-terminal recognition motifs are comprised in different amino acid sequences, for example, one N-terminally of the VSG, and the other linked to the immunogen such that there is a free carboxyl group at the end of the sortagging donor site. Some sortase recognition motifs are described herein and additional suitable sortase recognition motifs are well known to those of skill in the art. For example, sortase A of *S. aureus* recognizes and utilizes a C-terminal LPXT(G/A) motif, preferably LPXTG (SEQ ID NO: 12 and 13), (where X is any amino acid and glycine cannot be a free carboxylate) and an N-terminal polyglycinoligoglycine ($G_{1-5}$)—the index indicating the number of glycine compounds—, preferably $G_3$ or $G_5$, motif in transpeptidation reactions. Additional sortase recognition motifs will be apparent to those of skill in the art, and the invention is not limited in this respect. A sortase substrate may comprise additional moieties or entities apart from the peptidic sortase recognition motif. For example, a sortase substrate may comprise an LPXTG/A motif, the N-terminus of which is conjugated to any agent, (e.g. a peptide or protein, a small molecule, a binding agent, a lipid, a carbohydrate, or a detectable label). Similarly, a sortase substrate may comprise an oligoglycine ($G_{1-5}$) motif, preferably $G_3$ or $G_5$, the C-terminus of which is conjugated to any agent, e.g., a peptide or protein, a small molecule, a binding agent, a lipid, a carbohydrate, or a detectable label. Accordingly, sortase substrates are not limited to proteins or peptides but include any moiety or entity conjugated to a sortase recognition motif.

The terms "soratagging" in context of referring to a donor or acceptor sequence is sometimes also referred to as "sortase donor sequence", or "sortase acceptor sequence".

In some embodiments the immunogenic compound in accordance with the invention forms a linkage to the VSG via a sortagging donor sequence, such as—$(G)_3$SLPSTGG (SEQ ID NO: 14) and a sortagging acceptor sequence (e.g. AA- or GG-) by covalent connection mediated by a sortase transpeptidase reaction. Preferably, the linkage composed of the sortagging donor sequence and the sortagging acceptor sequence comprises the sequence -$(G)_3$SLPSTAA- (SEQ ID NO: 15), or a sortagging-functional variant thereof, as described in detail herein above. An example of sortase modified VSG can be derived from Pinger *J. et al., Nat. Commun.* 2017 Oct. 10;8(1):828. doi: 10.1038/s41467-017-00959-w.

A preferred eVSG of the invention has the following (covalent) structure from N- to C-terminus: an immunogenic compound, a sortagging donor sequence, a sortagging acceptor sequence, linker, VSG protein sequence.

Another preferred eVSG of the invention has the following (covalent) structure from N-to C-terminus: an immunogenic compound, followed by a peptide linker sequence (or not), followed by a sortase donor sequence, followed by a sortase acceptor sequence, followed by a peptide linker sequence (or not), and ending with a VSG protein sequence. Other engineered VSGs could alter the order and/or composition of these elements or covalently link them in other manners to VSG proteins (e.g. chemical or enzymatic cross-linking to surface-exposed amino acids or via diverse forms of protein ligation).

The antigenic particles of the invention may be used for a wide variety of purposes, mostly of a medical nature. Furthermore, the invention may be adjusted for a purpose of industrial nature, such as the generation of antibodies as removal agents of by-products of specific chemical reactions, among other applications. One advantage of the herein described invention is the wide range of applications possible via the surprising finding that the eVSG of the invention allows antigen presentation, in particular at their N-terminus. In one additional surprising embodiment of the invention the immunogenic compound used for the generation of the antigenic particle of the invention is a small-molecule drug, such as a therapeutic compound and/or a dependence-causing substance. The invention is therefore based on the inventive idea to use the trypanosome VSG coat for presenting small molecules for antibody generation. The inventors for the first time developed a system that allows such a dense presentation of small molecules that a strong immune reaction can be induced by the antigenic particles. The term "dependence-causing substance" shall refer to any compound or substance that when consumed by a subject induces physical or mental addiction to continue or repeat consumption of said dependence-causing substance. Classical substances known to be addictive in humans include but are not limited to amphetamines, morphines, cocaine and its related derivatives, alcohol and nicotine.

The immunogenic compound therefore, in this specific embodiment, is preferably, a dependency causing substance selected from (but only in particular embodiments limited to): (i) delta-9-tetrahydrocannabinol (THC) or synthetic cannabinoids, such as classical cannabinoids, non-classical cannabinoids, hybrid cannabinoids, aminoalkylindoles, and eicosanoids; for example 9-THC HU-210, (C8) CP 47,497, JWH-018, AM-2201 (Fluorinated JWH-018), UR-144, XLR-11 (Fluorinated UR-144), APICA, STS-135 (Fluorinated APICA). AB-PINACA, PB-22, 5F-PB-22 (Fluorinated PB-22); or (ii) methamphetamine and derivatives thereof such as 3,4-methylenedioxy-methamphetamine (MDMA)Ecstasy/Molly; or (iii) a synthetic cathinone like alpha-pyrrolidinopentiophenone (alpha-PVP); or (iv) an opioid including heroin, synthetic opioids such as fentanyl, carfentanyl and other opioid pain relievers, such as oxycodone (Oxy-Contin®), hydrocodone (Vicodin®), codeine, morphine, desomorphine (Krokodil); or (v) steroids (anabolic substances), or is nicotine.

Opium alkaloids and derivatives in accordance with the invention are selected from opium alkaloids: phenanthrenes like codeine; morphine; thebaine; oripavine or mixed opium alkaloids, including papaveretum; esters of morphine like diacetylmorphine (morphine diacetate; heroin); nicomorphine (morphine dinicotinate); dipropanoylmorphine (morphine dipropionate); diacetyldihydromorphine; acetylpropionylmorphine; dmaDesomorphine; methyldesorphine; dibenzoylmorphine; ethers of morphine like dihydrocodeine; ethylmorphine; heterocodeine.

Also included are semi-synthetic alkaloid derivatives such as buprenorphine; etorphine; hydrocodone; hydromorphone; oxycodone; oxymorphone.

In some particular embodiments, the immunogenic compound of the invention is preferably not a peptide, protein or proteinaceous fragments thereof. This embodiment is preferably realized if the invention pertains to small molecular compounds.

In further embodiments of the invention, small molecular compounds as immunogens may be linked to the VSG of the invention by linking the compound chemically to a peptide a sortagging sequence. For this the small molecular compound used as immunogenic compound of the invention is modified to be covalently linked to a peptide sortagging sequence. A way of linking small molecules to peptides is for example shown for fentanyl in M. D. Raleigh et al., J. Pharmacol. Exp. Ther. 368:282-291, 2019.

Also included are synthetic opioids such as anilidopiperidines like fentanyl; alphamethylfentanyl; alfentanil; sufentanil; remifentanil; carfentanyl; ohmefentanyl; also phenylpiperidines like pethidine (meperidine); ketobemidone; MPPP; allylprodine; prodine; PEPAP; promedol.

Diphenylpropylamine derivatives that are included comprise propoxyphene; dextropropoxyphene; dextromoramide; bezitramide; piritramide; methadone; dipipanone; levomethadyl acetate (LAAM); difenoxin; diphenoxylate; loperamide.

Further included are: Benzomorphan derivatives like Dezocine, Pentazocine, Phenazocine; Oripavine derivatives like Buprenorphine, Dihydroetorphine, Etorphine; Morphinan derivatives like Butorphanol; Nalbuphine; Levorphanol; Levomethorphan; Racemethorphan; Others like Lefetamine; Menthol (Kappa-Opioid agonist); Meptazinol; Mitragynine; Tilidine; Tramadol; Tapentadol; Eluxadoline; AP-237; 7-Hydroxymitragynine.

In some embodiments the antigenic particle of the invention may comprise two or more different eVSGs on its surface. Thereby the antigenic particle may be used to display two or more different (or 3, 4, 5, 6 etc.) immunogenic compounds on its surface coat. For example the different immunogenic compounds may comprise different immunogenic epitopes of one antigen or may comprise different epitopes of different antigens.

In some additional or alternative embodiments of the invention the antigenic particle comprises a particle which is a biological cell, a vesicle, a nanoparticle or a bead. Preferably the particle is selected to be capable of being coated by VSG proteins. Most preferably the particle is a biological cell, for example of a micro-organism, preferably a protozoan organism, more preferably a trypanosome, more preferably *T. brucei*. In some embodiments the trypanosome is an enzyme glycophosphatidylinositol phospholipase C (GPI-PLC)-negative trypanosome. Using a GPI-PLC-negative *T. brucei* strain has the advantage that after inactivation of the cell, the VSG coat is not disassembled, but remains intact. Thus, in other additional or alternative embodiments the biological cell is a non-living, preferably non-infective biological cell, such as an inactivated biological cell, preferably a UV-crosslinked cell.

In some other embodiments of the invention the eVSG comprises the immunogen as one or more immunogenic amino acid sequence(s) (that preferably is (are) genetically) inserted into the VSG sequence. Preferably the inserted immunogenic sequence is a xenogenic sequence, and most preferably is inserted into the VSG sequence without causing a deletion in the wild-type VSG sequence. In some embodiments the insertion is located in a surface loop of VSG, such as a region between two secondary structural motifs in the VSG, and preferably wherein said surface loop is located in a 3-dimensional position within the VSG which is surface presented when the VSG is comprised or assembled in a VSG coat, preferably which is surface-accessible and can be presented to the immune system.

In some embodiments of the invention the immunogenic compound comprised in the antigenic particle is a disease-associated antigen, such as a peptide antigen, and the disease is preferably selected from a proliferative disorder, an infectious disease, an inflammatory disorder, an immune deficiency disorder or an autoimmune disorder; or the disease is a non-communicable disease. Most preferably the immunogenic compound is an antigen associated with an infectious disease or proliferative disorder; preferably the antigen is associated with the disease.

In some other embodiments, the particle is a biological cell and the eVSG is either fully or partially expressed within said biological cell. Hence, the biological cell comprises genetic constructs for the expression of the VSG in accordance with the invention. In this context preferably the partial expression is the expression of a VSG either comprising an internal peptide immunogen, or is the internal expression of an VSG comprising a linker sequence, optionally comprising a sortagging acceptor site, and together with an N-terminal signal peptide for cell surface expression, wherein the sortagging acceptor site is between the signal peptide sequence and the linker sequence.

A preferred antigenic particle in context of the invention is a living or an inactivated trypanosome cell having an intact VSG coat, wherein the VSG coat comprises ore or more immunogenic engineered VSG (ieVSG), preferably a high percentage of an ieVSG (20% or higher, 40% or higher, 50% or higher, 60% or higher, 70% or higher, 80% or higher, with increasing preference), wherein the ieVSG comprises an eVSG protein N-terminally linked to an immunogenic compound. Preferably the linkage is provided by a sortase-mediated reaction.

Figure 3A:
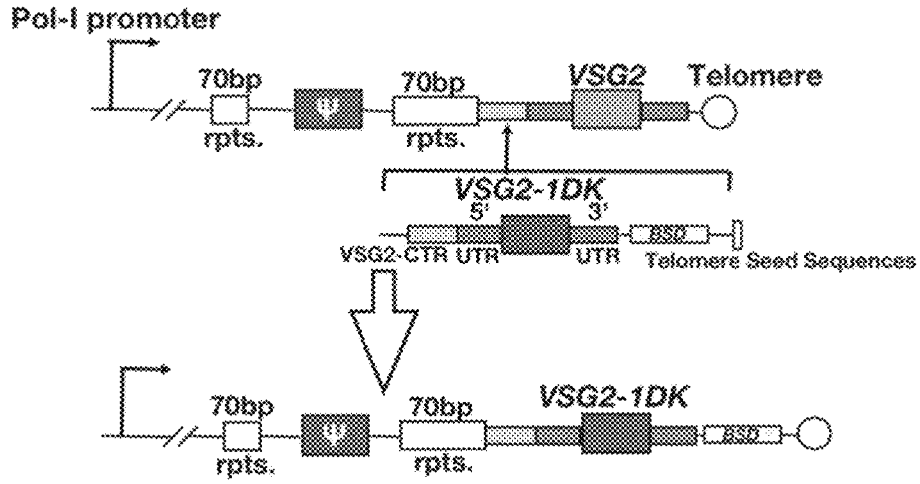
Figure 3B:
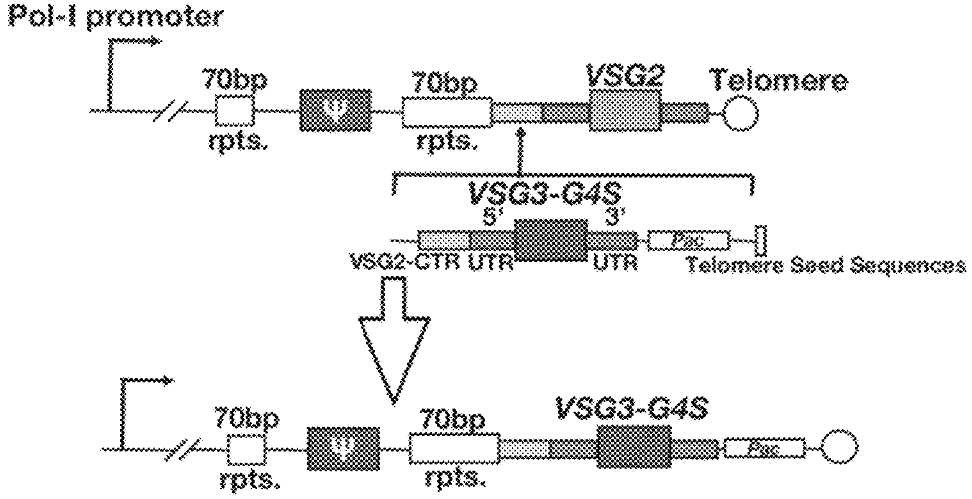
Figure 3C:
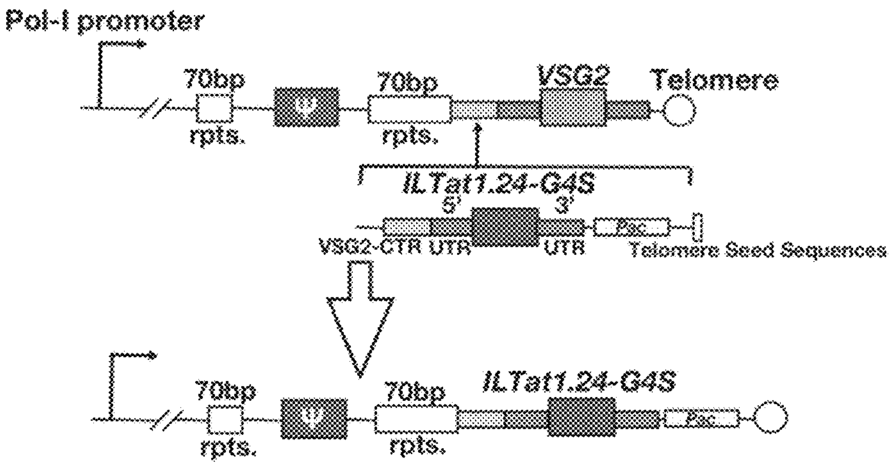

Further provided are nucleic acid constructs comprising an eVSG of the invention suitable for the introduction into the VSG expression locus of trypanosomes. Preferably the nucleic acid construct for introduction into a trypanosome has a structure as shown in any one of FIGS. 3A to 3C. Generally, a nucleic acid of the invention comprises the following elements in this order: a co-transposed region (CTR) of a VSG, for example about 1156 bp preceding the VSG2 open reading frame in Bloodstream Expression Site-1 (BES1) of the *T. brucei brucei* (Lister 427 strain) genome, immediately followed by the coding region for the eVSG in accordance with the invention, and a telomere seed sequence, for example a telomere seed sequence of about 150 to 250, preferably 200 bp. The construct may further comprise a resistance gene, for example blasticidin, puromycin or hygromycin, preferably following the eVSG coding region. Methods for integrating such constructs into the trypanosome genome are shown in Pinger et al., 2017 (Nature Communications), of which the materials and methods on pages 7 and 8 are incorporated herein by reference.

In another aspect the invention pertains to a method of producing an antigenic particle as described herein before.

Another aspect then pertains to an immunogenic engineered VSG (ieVSG) protein comprising in N- to C-terminal direction:

(a) An immunogenic compound,
(aa) optionally, a linker sequence (e.g. $G_3S$),
(b) A sortagging donor sequence (e.g. LPXTG/A (SEQ ID NO: 12 and SEQ ID NO: 13)),
(c) A sortagging acceptor sequence (e.g. AA or GG),
(d) A linker sequence (e.g. $(G_4S)_3$),
(e) A full-length, or essentially full-length VSG protein, such as a VSG protein of *Trypanosoma brucei* described herein before.

The ieVSG according to the invention is preferred, wherein any one of, any combination of or all of (a) to (e) is selected from the corresponding (a) to (e) of the antigenic particle according to the above descriptions.

Yet another aspect of the invention then provides a system comprising as components of the system a pre-ieVSG protein and a compound comprising a sortagging donor sequence, wherein the pre-ieVSG protein comprises in N- to C-terminal direction:

(a') Optionally a signal peptide,
(b') A sortagging acceptor sequence (e.g. AA or GG),
(c') A linker sequence (e.g. (G4S)3),
(d') A full-length, or essentially full-length VSG protein, such as a VSG protein of *Trypanosoma brucei*.

In some embodiments the system of the invention further comprises as additional components a sortase enzyme, or means for the generation of a sortase enzyme.

A "pre-ieVSG" in accordance with the invention is an eVSG having a free N-terminal acceptor site for the addition of an immunogenic compound. For example the pre-ieVSG is expressed on the coat of a trypanosome cell and comprises a free sortase acceptor sequence outside (such as accessible on the surface of) the VSG coat. Using a sortase enzyme in a sortase reaction, the pre-ieVSG can be fused to an immunogenic compound which is coupled to a sortase donor sequence.

In some embodiments the pre-ieVSG protein is provided as a nucleic acid sequence for the expression of a pre-ieVSG protein, for example for the expression of the pre-ieVSG in a biological cell. Suitable expression systems for expressing VSG genes in trypanosomes are well known in the art, and exemplified in the example section. Other expression systems in this invention may include diverse prokaryotic and eukaryotic organisms (e.g. yeast, insect cells and mammalian cells) as well as in vitro expression systems.

The system of the invention may further comprise as additional component means for covalently attaching the sortagging donor sequence to a compound used as immunogen.

A further component of the system according to the invention is a biological cell, preferably a trypanosome cell, such as a *T. brucei* cell, more preferably a GPI-PLC-negative *T. brucei* cell.

The antigenic particle, the ieVSG or the system according to the invention include in preferred embodiments a VSG derived from the genome of *T. brucei*, preferably VSG1, VSG2, VSG3 or ILTat1.24.

A further aspect of the present invention then pertains to a pharmaceutical composition comprising an antigenic particle according to the invention together with a pharmaceutically acceptable carrier and/or excipient. A pharmaceutical composition is manufactured for administration to a subject for therapy, prevention or management of a disease or disorder.

A pharmaceutical composition is preferably formulated as a vaccine composition, hence, a composition suitable for vaccination a subject in need of such a treatment.

By way of example, the pharmaceutical composition of the invention may comprise between 0.1% and 100% (w/w) active ingredient, such as about 0.5%, 1%, 2%, 3%, 4%, 5%, 6%, 8% 10%, 15%, 20%, 25%, 30%, 40%, 50%, 60%, 70%, 80%, 90%, 95%, 96%, 97%, 98% or 99%, preferably between about 1% and about 20%, between about 10% and 50% or between about 40% and 90%. An active ingredient of the composition of the invention is preferably an antigenic particle of the invention.

As used herein the language "pharmaceutically acceptable" excipient, stabiliser or carrier is intended to include any and all solvents, solubilisers, fillers, stabilisers, binders, absorbents, bases, buffering agents, lubricants, controlled release vehicles, diluents, emulsifying agents, humectants, dispersion media, coatings, antibacterial or antifungal agents, isotonic and absorption-delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition of (or for use with) the invention is, typically, formulated to be compatible with its intended route of administration. Examples of routes of administration include oral, parenteral, e.g., intrathecal, intra-arterial, intravenous, intradermal, subcutaneous, oral, intraperitoneal, transdermal (topical) and transmucosal administration.

Solutions or suspensions used for parenteral, intradermal, or subcutaneous application, as well as comprising a compound of (or for use with) the invention (e.g. an antigenic particle of the invention), can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Kollipho®EL (formerly Cremophor EL™; BASF, Parsippany, N.J.) or phosphate buffered saline (PBS). In all cases, the injectable composition should, typically, be sterile and be fluid to the extent that easy syringability exists. It should, typically, be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminium monostearate and gelatin.

Oral compositions, as well as comprising a compound of (or for use with) the invention (e.g. an antigenic particle of the invention), generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavouring agent such as peppermint, methyl salicylate, or orange flavouring.

Furthermore, the compounds of (or for use with) the invention (e.g. the antigenic particle of the invention) can be administrated rectally. A rectal composition can be any rectally acceptable dosage form including, but not limited to, cream, gel, emulsion, enema, suspension, suppository, and tablet. One preferred dosage form is a suppository having a shape and size designed for introduction into the rectal orifice of the human body. A suppository usually softens, melts, or dissolves at body temperature. Suppository excipients include, but are not limited to, theobroma oil (cocoa butter), glycerinated gelatin, hydrogenated vegetable oils, mixtures of polyethylene glycols of various molecular weights, and fatty acid esters of polyethylene glycol.

For administration by inhalation, the compounds of (or for use with) the invention (e.g. an antigenic particle of the invention) are typically delivered in the form of an aerosol spray from pressured container or dispenser which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions can be formulated into ointments, salves, gels, or creams as generally known in the art.

In certain embodiments, the pharmaceutical composition is formulated for sustained or controlled release of a compound of (or for use with) the invention (e.g. an antigenic particle of the invention). Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially (including liposomes targeted to infected cells with monoclonal antibodies to viral antigens) can also be used as pharmaceutically acceptable carriers. These can be prepared according to methods known to those skilled in the art.

Exemplary unit dosage forms for pharmaceutical compositions comprising the antigenic particles of the invention are tablets, capsules (e.g. as powder, granules, microtablets or micropellets), suspensions or as single-use pre-loaded syringes. In certain embodiments, kits are provided for producing a single-dose administration unit. The kit can contain both a first container having a dried active ingredient and a second container having an aqueous formulation. Alternatively, the kit can contain single and multi-chambered pre-loaded syringes.

As mentioned above, preferred pharmaceutical compositions are vaccine compositions. As used herein, the term "vaccine composition" refers to an immunogenic composition which, when administered to a subject, elicits protective immunity against an antigen, in this case the antigen represented by the immunogenic compound. Antibodies produced in accordance with the invention may also be used as therapeutics or passive immunization.

Furthermore, the vaccine composition may include one or more adjuvants. As used herein the term "adjuvant" refers to a compound that, when used in combination with a specific antigenic particle in a formulation, will augment or otherwise alter or modify the resultant immune response. Modification of the immune response can include intensification or broadening the specificity of either or both antibody and cellular immune responses. Modification of the immune response can also mean decreasing or suppressing certain antigen-specific immune responses.

Examples of known adjuvants include complete Freund's adjuvant (a non-specific stimulator of the immune response, containing killed *Mycobacterium tuberculosis*), incomplete Freund's adjuvants and aluminium hydroxide adjuvant. Other known adjuvants include granulocyte macrophage colony-stimulating factor (GM-CSF), Bacillus Calmette-Guérin (BCG), aluminium hydroxide, Muramyl dipeptide (MDP) compounds, such as thur-MDP and nor-MDP, muramyl tripeptide phosphatidylethanolamine (MTP-PE), RIBI's adjuvants (Ribi ImmunoChem Research, Inc., Hamilton Mont.), which contains three components extracted from bacteria, trehalose dimycolate (TDM) and cell wall skeleton (CWS) in a 2% squalene/Tween 80 emulsion. MF-59, Novasomes®, major histocompatibility complex (MHC) antigens are other known adjuvants.

In some embodiments the vaccine composition may include two, three, four, five, six, seven, eight, nine or more antigenic particles, each comprising a difference immunogenic compound derived from one or more antigens.

The herein provided substances, compositions and systems of the invention are preferably for use in the prevention, management, and/or treatment of a medical condition. Hence, the invention relates to a use of the herein disclosed substances, compositions or systems for the manufacture of a medicament of the prevention, management, and/or treatment of a medical condition. Furthermore, the invention relates to a method for prevention, management, and/or treatment of a medical condition, the method comprising the administration of an effective amount of a substances, compositions or system of the invention to a subject in need of such a treatment.

A medical condition which can be prevented, managed or treated in accordance with the invention is in preferred embodiments an addiction to a dependence-causing substance. In this embodiment the immunogenic compound of the antigenic particle is the dependence-causing substance. Without being bound to theory it is expected that the antigenic particles of the invention provide an improved vaccination strategy leading to a strong immune response in a subject and thereby antibodies produced in the subject in response to the antigenic particle will serve as "sponges" to neutralise the dependence-causing substance in the event the subject consumes such substance during a fall-back to the addictive behaviour. Thereby, the vaccination strategy of the invention reduces the positive sensation of the dependence-causing substance and helps the subject to overcome the addiction.

A medical condition which can be prevented, managed or treated in accordance with the invention is in other preferred embodiments an adverse or fatal event caused by drug adulterant. Drug adulterants are substances consumed together with a preparation of a drug of abuse, but often lead to severe overdosing and not-rarely serious adverse effects and even death of the subject. In this embodiment the antigenic particle of the invention includes an immunogenic compound inducing an immune response against a common adulterant in order to protect the abuser from an overdose. Preferably in such a treatment the subject is administered also an antigenic particle of the invention specific for the drug of abuse to which the subject has an addiction.

The medical uses of the invention may include the control, management or amelioration of a drug overdose, including overdosing of pure compounds or adulterants. In this aspect, the medical use includes also in preferred embodiments a prevention of overdosing in a subject suspected to be at risk of being exposed to such overdosing by pure compounds or adulterants. This might include a vaccination according to the invention against a dependency causing drug in a subject suspected to suffer from drug addiction, and possible relapse of use.

In further embodiments the invention pertains to a medical condition which is an infectious disease, and wherein the immunogenic compound of the antigenic particle is an immunogenic compound or sequence derived from the infectious organism causing the infectious disease. In preferred aspects the disease is malaria. Known and preferred malaria antigens are well known to the skilled person. For example, the immunogen is a compound derived from the plasmodium surface.

Other embodiments of the invention pertain to cancer, and wherein the immunogenic compound of the antigenic particle is a compound associated with or specific for a cancer cell of the cancer.

Other embodiments of the invention pertain to the creation of "slow release depots" (SRDs) for the application of chemotherapeutic agents. SRDs are antibodies or any product of vaccination that bind to specific chemotherapeutic compounds and alter the pharmokinetics or other properties of the treatment for useful purposes (such as reduction of toxicity, prolongation of half-life, alternative tissue tropism, etc.). An example is anticancer chemotherapeutic agents (platinum, Adriamycin, etc.) and the generation of antibodies or immune reactions from vaccination that allow for the capture and "slow release" of the chemotherapeutic agents for therapeutic or other useful purposes. Other examples include chemotherapeutics for infectious diseases or allergies for which immunological SRDs provide useful approaches. SRDs for compounds used in industrial applications would also be an embodiment of this invention.

An additional embodiment of the invention pertains to aspects of neurodegenerative diseases and antibodies or any product of vaccination against specific proteins. Examples include: Alzheimer's disease (Amyloid beta (Ab) peptide, Tau), Parkinson's disease (α-Synuclein), Multiple Tauopathies (Tau protein, microtubule-associated), Huntington's disease (Huntingtin with or without tandem glutamine repeats), Amyotrophic lateral sclerosis (Superoxide dismutase Spongiform encephalopathies (Prion proteins), Familial amyloidotic polyneuropathy (Transthyretin, wild-type and mutant forms), small peptides like those associated with migraines), and any possible peptide or small molecule targets that are deemed useful, including but not limited to industrial, agricultural, research or diagnostic purposes.

In general anything for which an antibody or generalized immune response has shown or could reasonably be expected to potentially show usefulness in a medical, diagnostic or industrial settings qualifies as an embodiment of this invention.

The medical use of the antigenic particle of the invention usually involves the administration of the antigenic particle to a subject in need of the prevention, management, and/or treatment of the medical condition, for example in the form of a vaccine composition as described herein before.

Yet another aspect of the present invention then pertains to a method for the generation of an antibody which is capable of binding to an immunogenic compound, the method comprising the steps of providing an antigenic particle according to the invention, wherein the immunogenic compound of the antigenic particle is the immunogenic compound, or immunogenic parts thereof, the antibody to be generated is capable to bind to; immunizing an antibody-producing human or non-human animal with the antigenic particle; isolating from the immunized human or animal immune cells producing antibodies against said immunogen, and optionally, isolating from said cells said so generated antibodies.

In context of the herein disclosed invention the non-human animal is preferably selected from mouse, rabbit, camel, goat, rat, dog, cat, monkey, hamster or other mammals.

Yet a further aspect then pertains to a method of vaccinating a subject in need of an enhanced immune response specific for an immunogenic compound, the method comprising administering to the subject an amount of an antigenic particle according to the invention which is sufficient to induce an immune response in the subject against the immunogenic compound, wherein the immunogenic compound comprised in the antigenic particle is identical to or is an immunogenic part of, the immunogenic compound for which the enhanced immune response is specific. Preferred is a method for preventing, managing or treating a medical condition, and wherein the immunogenic compound is associated with the medical condition.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

In view of the above, it will be appreciated that the present invention also relates to the following itemised embodiments:

Item 1: An antigenic particle coated with an engineered variant surface glycoprotein (eVSG), wherein the eVSG comprises an immunogenic compound.

Item 2: The antigenic particle according to item 1, wherein the immunogenic compound is a small molecule, a nucleic acid, or a peptide.

Item 3: The antigenic particle according to item 1, wherein the immunogenic compound is covalently linked, optionally via a linker, to the N-terminus of the VSG.

Item 4: The antigenic particle according to item 3, wherein the linker is an N-terminal extension of the wild-type VSG N-terminus, and preferably comprises 5 to 30 amino acids, preferably 10 to 20, more preferably about 15 amino acids.

Item 5: The antigenic particle according to item 4, wherein the linker is a G4S linker, such as a linker having the linker sequence GGGGSGGGGSGGGGS (SEQ ID NO: 8)

Item 6: The antigenic particle according to any one of items 1 to 5, wherein linker further comprises N-terminally to the linker sequence a sortagging acceptor sequence such as AA-.

Item 7: The antigenic particle according to any one of items 1 to 6, wherein the immunogenic compound forms a linkage to the VSG via a sortagging donor sequence, such as (G)3SLPSTGG (SEQ ID NO: 14) and a sortagging acceptor sequence by covalent connection mediated by a sortase.

Item 8: The antigenic particle according to item 7, wherein the linkage composed of the sortagging donor sequence and the sortagging acceptor sequence comprises the sequence—(G)3SLPSTGAA (SEQ ID NO: 15), or a sortagging-functional variant thereof.

Item 9: The antigenic particle according to any one of items 1 to 8, wherein the eVSG has the following (covalent) structure from N- to C-terminus: immunogenic compound, a sortagging donor sequence, a sortagging acceptor sequence, a linker, the VSG protein sequence.

Item 10: The antigenic particle according to any one of items 1 to 9, wherein the immunogenic compound is a small molecular drug, such as therapeutic compound and/or a dependence causing substance.

Item 11: The antigenic particle according to item 10, wherein the immunogenic compound is a dependency causing substance selected from (i) delta-9-tetrahydrocannabinol (THC) or Synthetic cannabinoids, such as classical cannabinoids, non-classical cannabinoids, hybrid cannabinoids, aminoalkylindoles, and eicosanoids; for example Δ9-THC HU-210, (C8) CP 47,497, JWH-018, AM-2201 (Fluorinated JWH-018), UR-144, XLR-n (Fluorinated UR-144), APICA, STS-135 (Fluorinated APICA). AB-PINACA, PB-22, 5F-PB-22 (Fluorinated PB-22); or (ii) methamphetamine and derivatives thereof such as 3,4-methylenedioxy-methamphetamine (MDMA)Ecstasy/Molly; or (iii) a synthetic cathinone like alpha-pyrrolidinopentiophenone (alpha-PVP); or (iv) an opioid including heroin, synthetic opioids such as fentanyl, and other opioid pain relievers, such as oxycodone (OxyContin®), hydrocodone (Vicodin®), codeine, morphine, desomorphine (Krokodil); or (v) steroids (anabolic substances), or is nicotine. [more detail in the description]

Item 12: The antigenic particle according to any one of items 1 to 11, wherein the particle is a biological cell, a vesicle, a nanoparticle or a bead.

Item 13: The antigenic particle according to item 12, wherein the biological cell is a microorganism, preferably a protozoan organism, more preferably a trypanosome, more preferably.

Item 14: The antigenic particle according to item 13, wherein the trypanosome is an enzyme phospholipase C (or PLC) negative trypanosome.

Item 15: The antigenic particle according to any one of items 12 to 14, wherein the biological cell is a non-living, preferably non-infective biological cell, such as an inactivated biological cell, preferably a UV-cross-linked cell.

Item 16: The antigenic particle according to any one of the preceding items, wherein the eVSG comprises the immunogen as immunogenic amino acid sequence inserted into the VSG sequence.

Item 17: The antigenic particle according to item 16, wherein the insertion is located in a surface loop of VSG, such as a region between two secondary structural motifs in the VSG, and preferably wherein said surface loop is located in a 3 dimensional position within the VSG which, when the VSG is comprised in a VSG coat, coat-surface presented.

Item 18: The antigenic particle according to any one of the preceding items, wherein the immunogen is disease associated antigen, such as a peptide antigen, and wherein the disease is selected from a proliferative disorder, an infectious disease, and inflammatory disorder, and immune deficiency disorder or an autoimmune disorder.

Item 19: The antigenic particle according to any one of the preceding items, wherein the particle is a biological cell and wherein the eVSG is either fully or partially expressed within the biological cell.

Item 20: The antigenic particle according to item 19, wherein the partial expression is the expression of a VSG either comprising an internal peptide immunogen, or is the internal expression of an VSG comprising a linker sequence, optionally comprising a sortagging acceptor site, and together with an N-terminal signal peptide for cell surface expression, wherein the sortagging acceptor site is between the signal peptide sequence and the linker sequence.

Item 21: An immunogenic engineered VSG (ieVSG) protein comprising in N- to C-terminal direction:

(a) An immunogenic compound, (b) A sortagging donor sequence, (c) A sortagging acceptor sequence, (d) A linker sequence, (e) A full length, or essentially full length, VSG protein, such as a VSG protein of *Trypanosoma brucei;* Optionally wherein the ieVSG is a soluble protein.

Item 22: The ieVSG according to item 21, wherein any one of, any combination of or all of (a) to (e) is selected from the corresponding (a) to (e) of the antigenic particle according to any one of items 1 to 20.

Item 23: A system comprising as components a pre-ieVSG protein and a compound comprising a sortagging donor sequence, wherein the pre-ieVSG protein comprises in N- to C-terminal direction:

(a') Optionally a signal peptide, (b') A sortagging acceptor sequence, (c') A linker sequence, (d') A full length, or essentially full length, VSG protein, such as a VSG protein of *Trypanosoma brucei*.

Item 24: The system according to item 23, further comprising, a sortase enzyme, or means for the generation of a sortase enzyme.

Item 25: The system according to item 23 or 24, wherein the pre-ieVSG protein is provided as a nucleic acid sequence for the expression of a pre-ieVSG protein, for example for the expression of the pre-ieVSG in a biological cell.

Item 26: The system according to any of items 23 to 25, further comprising means for covalently attaching the sortagging donor sequence to a compound used as immunogen.

Item 27: The system according to any one of items 23 to 26, further comprising a biological cell, preferably a Trypanosoma cell, such as a *T. brucei* cell, more preferably a PLC negative *T. brucei* cell.

Item 28: The antigenic particle, the ieVSG or the system according to any one of the preceding items, wherein the VSG is a VSG derived from the genome of *T. brucei*, preferably is VSG1, VSG2, VSG3 or ILTat1.24.

Item 29: An antigenic particle according to any one of items 1 to 20, for use in the prevention, management, and/or treatment of a medical condition.

Item 30: The antigenic particle for use according to item 29, wherein the medical condition is an addiction to a dependence causing substance, and wherein the immunogen of the antigenic particle is the dependence causing substance.

Item 31: The antigenic particle for use according to item 29, wherein the medical condition is an infectious disease, and wherein the immunogen of the antigenic particle is an immunogenic compound or sequence derived from the infectious organism causing the infectious disease.

Item 32: The antigenic particle for use according to item 31, wherein the infectious disease is malaria, and wherein the immunogen is compound derived from Plasmodium.

Item 33: The antigenic particle for use according to item 29, wherein the medical condition is cancer, and wherein the immunogen of the antigenic particle is a compound associated with or specific for a cancer cell of the cancer.

Item 34: The antigenic particle for use according to any one of items 29 to 34, wherein the antigenic particle is administered to a subject in need of the prevention, management, and/or treatment of the medical condition, for example in the form of a vaccine composition.

Item 35: A method for the generation of an antibody which is capable of binding to an immunogenic compound, the method comprising the steps of providing an antigenic particle according to any one of item 1 to 20, wherein the immunogenic compound of the antigenic particle is the immunogenic compound, or immunogenic parts thereof, the antibody to be generated is capable to bind to; immunizing an antibody producing non-human animal with the antigenic particle; isolating from the immunized animal immune cells producing antibodies against said immunogen, and optionally, isolating from said cells said so generated antibodies.

Item 36: The method according to item 35, wherein the antibody producing non-human animal is selected from mouse, rabbit, camel, goat, rat, dog, cat, monkey, hamster, or other mammals.

Item 37: A use of a system according to any one of items 23 to 27, in the generation of an antibody, preferably according to a method of item 35 or 26.

Item 38: A method of vaccinating a subject in need of an enhanced immune response specific for an immunogenic compound, the method comprising administering to the subject an amount of an antigenic particle according to any one of items 1 to 20 which is sufficient to induce an immune response in the subject against the immunogenic compound, wherein the immunogenic compound comprised in the antigenic particle is identical to or is an immunogenic part of, the immunogenic compound for which the enhanced immune response is specific.

Item 39: The method according to item 38, wherein the method is a method or preventing, managing or treating a medical condition, and wherein the immunogenic compound is associated with the medical condition.

In view of the above, it will be appreciated that the present invention also relates to the following itemised B embodiments:

Item B1: An antigenic particle coated with an engineered variant surface glycoprotein (eVSG), wherein the eVSG comprises a VSG linked to an immunogenic compound, wherein the immunogenic compound is a small molecular compound, and which is covalently linked via a linker to the N-terminus of the VSG.

Item B2: The antigenic particle according to item B 1, wherein the eVSG has the following covalent structure from N- to C-terminus: immunogenic compound, a sortagging donor sequence, a sortagging acceptor sequence, optionally a linker, and the VSG protein sequence.

Item B3: The antigenic particle according to item B 1 or 2, wherein the immunogenic compound is a small molecular drug, such as and/or therapeutic compound a dependency-causing substance.

Item B4: The antigenic particle according to any one of items B 1 to 3, wherein the immunogenic compound is a dependency causing substance selected from (i) delta-9-tetrahydrocannabinol (THC) or synthetic cannabinoids, such as classical cannabinoids, non-classical cannabinoids, hybrid cannabinoids, aminoalkylindoles, and eicosanoids; for example Δ9-THC HU-210, (C8) CP 47,497, JWH-018, AM-2201 (Fluorinated JWH-018), UR-144, XLR-11 (Fluorinated UR-144), APICA, STS-135 (Fluorinated APICA). AB-PINACA, PB-22, 5F-PB-22 (Fluorinated PB-22); or (ii) methamphetamine and derivatives thereof such as 3,4-methylenedioxy-methamphetamine (MDMA)Ecstasy/Molly; or (iii) a synthetic cathinone like alpha-pyrrolidinopentiophenone (alpha-PVP); or (iv) an opioid including heroin, synthetic opioids such as fentanyl, and other opioid pain relievers, such as oxycodone (OxyContin®), hydrocodone (Vicodin®), codeine, morphine, desomorphine (Krokodil); or (v) steroids (anabolic substances), or is nicotine.

Item B5: The antigenic particle according to any one of items B 1 to 4, wherein the particle is a biological cell, a vesicle, a nanoparticle or a bead.

Item B6: The antigenic particle according to item B 5, wherein the biological cell is a microorganism, preferably a protozoan organism, more preferably a trypanosome.

Item B7: The antigenic particle according to any one of items B 5 to 6, wherein the biological cell is an inactivated biological cell, preferably a UV-crosslinked biological cell.

Item B8: The antigenic particle according to any one of the preceding items B, wherein the VSG is a VSG derived from the genome of *T. brucei*, such as VSG1, VSG2, VSG3 or ILTat1.24.

Item B9: An immunogenic engineered VSG (ieVSG) protein, comprising in N- to C-terminal direction:

(a) An immunogenic compound,
(b) A sortagging donor sequence,
(c) A sortagging acceptor sequence,
(d) A linker sequence,
(e) A full length, or essentially full length, VSG protein.

Item B10: A system or kit, comprising as components (i) a pre-ieVSG protein and (ii) a compound comprising a sortagging donor sequence, wherein the pre-ieVSG protein comprises in N- to C-terminal direction:

(a') Optionally a signal peptide,
(b') A sortagging acceptor sequence,
(c') A linker sequence,
(d') A full length, or essentially full length, VSG protein.

Item B11: The system or kit according to item B 9, further comprising, a sortase enzyme, or means for the generation of a sortase enzyme.

Item B12: The system or kit according to items B 10 or 11, wherein the pre-ieVSG protein is provided as a nucleic acid sequence for the expression of a pre-ieVSG protein, for example for the expression of the pre-ieVSG in a biological cell.

Item B13: The system or kit according to any one of items B 10 to 12, further comprising means for covalently attaching the sortagging donor sequence to a compound used as immunogen.

Item B14: An antigenic particle for use in the prevention, management, and/or treatment of a medical condition, wherein the antigenic particle is an antigenic particle as recited in any one of items B1 to 8.

Item B15: The antigenic particle for use according to item B 14, wherein the medical condition is an addiction to a dependency causing substance, and wherein the immunogen of the antigenic particle is the dependency causing substance.

Item B16: The antigenic particle for use according to item B 14, wherein the medical condition is an infectious disease or a cancer, and wherein the immunogen of the antigenic particle is an immunogenic compound or sequence (epitope) derived from the infectious organism causing the infectious disease, or the cancer respectively.

Item B17: The antigenic particle for use according to any one of items B 14 to 16, wherein the antigenic particle is administered to a subject in need of the prevention, management, and/or treatment of the medical condition, for example in the form of a vaccine composition.

Item B18: A method for the generation of an antibody which is capable of binding to an immunogenic compound, the method comprising the steps of providing an antigenic particle according to any one of items B1 to 8, wherein the immunogenic compound of the antigenic particle is the immunogenic compound, or immunogenic parts thereof, the antibody to be generated is capable or intended to bind to; immunizing an antibody producing non-human animal with the antigenic particle; isolating from the immunized animal immune cells producing antibodies against said immunogen, and optionally, isolating from said cells said so generated antibodies.

Item B19: A method of vaccinating a subject in need of an enhanced immune response, and wherein the immune response is specific for an immunogenic compound, the method comprising administering to the subject an amount of an antigenic particle according to any one of items B 1 to 8 which is sufficient to induce an immune response in the subject against the immunogenic compound, wherein the immunogenic compound comprised in the antigenic particle is identical to or is an immunogenic part of, the immunogenic compound for which the enhanced immune response is specific.

Item B20: The method according to item B 19, wherein the method is for preventing, managing or treating a medical condition, and wherein the immunogenic compound is associated with the medical condition.

BRIEF DESCRIPTION OF THE FIGURES AND SEQUENCES

Figure 1B:
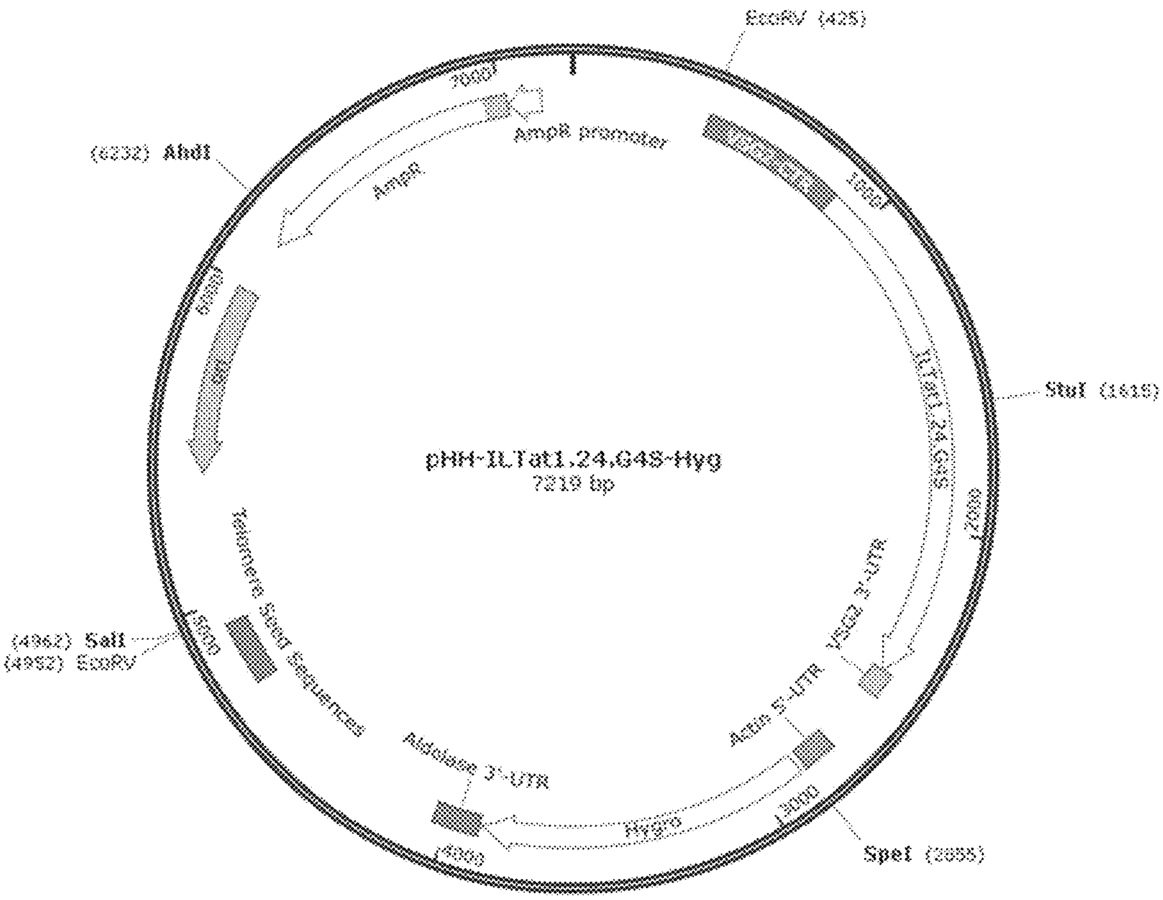

The figures show:

FIG. 1: shows a map of plasmids used for VSG engineering. Sequences of pHH-VSG3. G4S-Hyg and pHH-ILTat1.24-G4S-Hyg plasmids are provided in SEQ ID NO: 6 and SEQ ID NO: 7 respectively. (A) pHH-VSG3.G4S-Hyg Plasmid Size: 7204 bp. VSG2-CTR (VSG2 Co-transposed Region): 429-878; VSG3.G4S (S317A): 879-2453; VSG2 3'-UTR (VSG2 3'-Untranslated Region): 2454-2533; Actin 5'-UTR (Actin 5'-Untranslated Region): 2727-2834; Hygro (Hygromycin Resistance Gene): 2854-3879; Aldolase 3'-UTR (Aldolase 3'-Untranslated Region): 3885-4033; Telomere Seed Sequences: 4715-4915; Ori (Bacterial Origin of Replication): 5385-5973; AmpR (Ampicillin Resistance Gene, Beta-lactamase): 6144-7004 (Reverse Complement); AmpR Promotor (Ampicillin Resistance Gene Promoter, Beta-Lactamase Promoter): 7005-7109 (Reverse Complement); (B) pHH-ILTat1.24-G4S-Hyg Plasmid Size: 7219 bp. VSG2-CTR (VSG2 Co-transposed Region): 429-878; ILTat1.24-G4S: 879-2468; VSG2 3'-UTR (VSG2 3'-Untranslated Region): 2469-2548; Actin 5'-UTR (Actin 5'-Untranslated Region): 2742-2849; Hygro (Hygromycin Resistance Gene): 2869-3894; Aldolase 3'-UTR (Aldolase 3'-Untranslated Region): 3900-4048; Telomere Seed Sequences: 4730-4930; Ori (Bacterial Origin of Replication): 5400-5988; AmpR (Ampicillin Resistance Gene, Beta-lactamase): 6159-7019 (Reverse Complement); AmpR Promotor (Ampicillin Resistance Gene Promoter, Beta-Lactamase Promoter): 7020-7124 (Reverse Complement).

Figure 2:
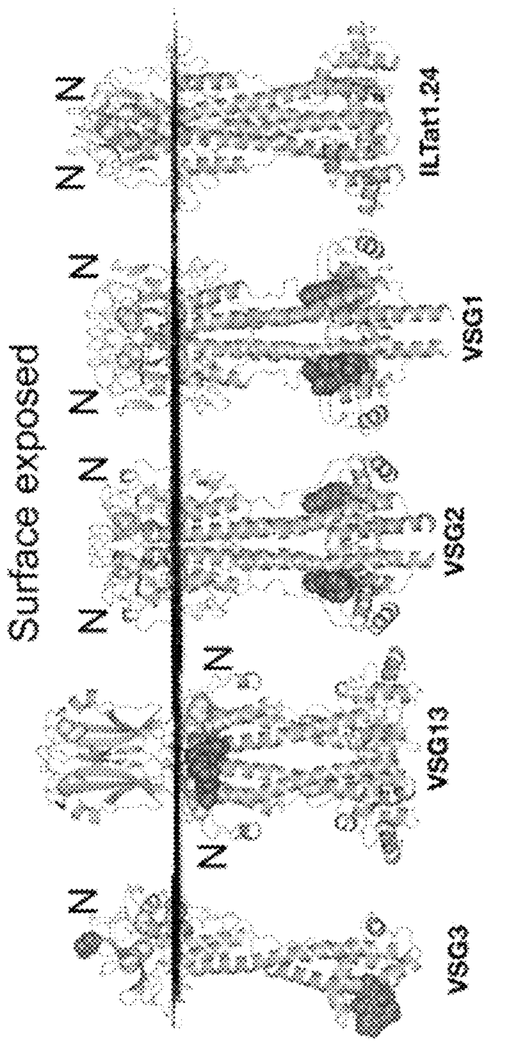

FIG. 2: shows that crystallographic studies help determine the accessibility of the VSG N-terminus to the sortase enzyme is illustrated using 5 examples (all published except VSG13). "N" denotes the location of the free N-terminus for each protein. The line denotes a roughly estimated general location of surface-exposed residues (the "top" of the VSG coat, what would be accessible to the sortase enzyme). While many VSGs can be engineered to accept tags through sortase-based conjugation (and the inventors have already done this for VSG2, VSG3 and ILTat1.24 as discussed later), not all can be (for example the N-terminus in VSG13 is far more buried and may not be sufficiently accessible). Structural biology presents a very useful pre-screening of VSGs to uncover many surface elements and other architectural features that inform the choices of VSGs (e.g., the discovery of the O-linked sugar on VSG3 that led the inventors to work with a specific serine to alanine mutant, S317A, to remove it from the surface).

FIG. 3: shows the knock-in strategy of sortaggable VSGs into the genome of *Trypanosoma brucei*. A to C show the genetic cloning strategy to express engineered VSG2, VSG3 and ILTat1.24 from the active expression site of endogenous VSG (replacing wild-type VSG2).

FIG. 4: shows the amino acid sequences of the sortaggable VSG proteins. A. Amino acid sequence of the sortaggable VSG3.G4S (S317A) protein. The signal peptide is underlined. The mature, sortaggable VSG3 is derived from a more antigenic mutant of wild-type VSG3 (S317A). VSG3-G4S will initiate with the di-Alanine (in bold and italic). This dipeptide will be the acceptor of the sortase A reaction (and will accept any moiety N-terminally linked to the peptide sequence LPSTGG). The extension of the N-terminus (by addition of the $(G_4S)_3$ peptide linker, in bold), is crucial for the ability of sortase A to access the di-Alanine. B. Amino acid sequence of the sortaggable VSG2 protein (VSG2-1DK). The signal peptide is underlined. The mature, sortaggable VSG2-1DK will initiate with the di-Alanine (in bold and italic). This dipeptide will be the acceptor of the sortase A reaction (and will accept any moiety N-terminally linked to the peptide sequence LPSTGG). The extension of the N-terminus (by addition of a linker peptide consisting of a TEV protease cleavage site flanked by poly-Glycine, in bold) is crucial for the ability of sortase A to access the di-Alanine. C. Amino acid sequence of the sortaggable ILTat1.24 protein (ILTat1.24-G4S). The signal peptide is underlined. The mature, sortaggable ILTat1.24-G4S will initiate with tetra-Glycine (shown in bold and italic). This tetra-Glycine will be the acceptor of the Sortase A reaction (and will accept any moiety N-terminally linked to the peptide sequence LPSTGG). The extension of the VSG N-terminus (by addition of the (G4S)2 peptide linker, in bold), is crucial for the ability of Sortase A to access the tetra-Glycine.

Figure 5:
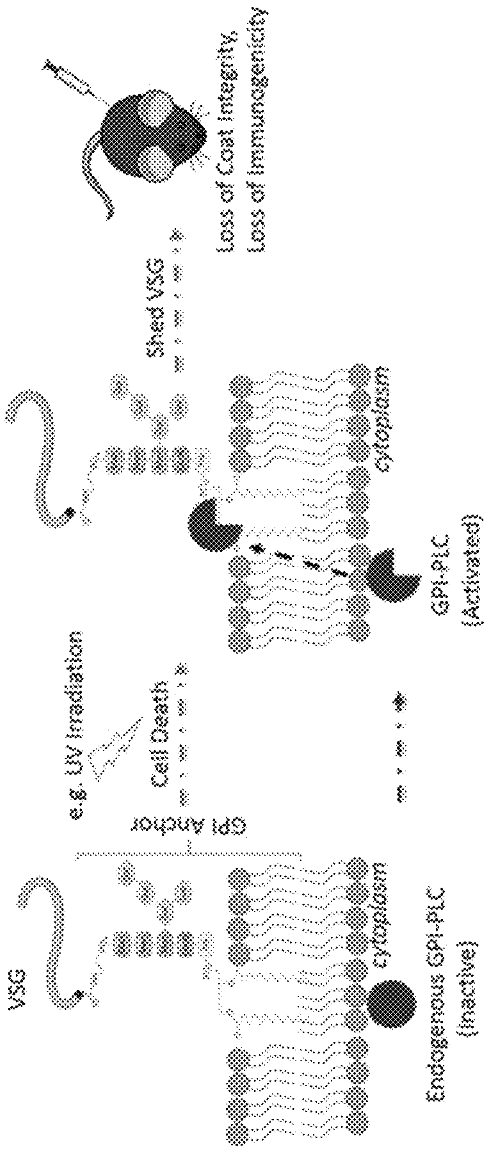

FIG. 5: shows the wild-type *T. brucei* sheds its VSG coat upon death. A. Cartoon of the process showing that GPI-PLC is activated upon cell death. B. The location of GPI anchor cleavage site is shown. Cleavage of the GPI anchor releases (sheds) VSG from the coat and the coat-less trypanosome disintegrates through osmotic pressure (and consequently losing its immunogenic properties).

Figures 6A, 6B:
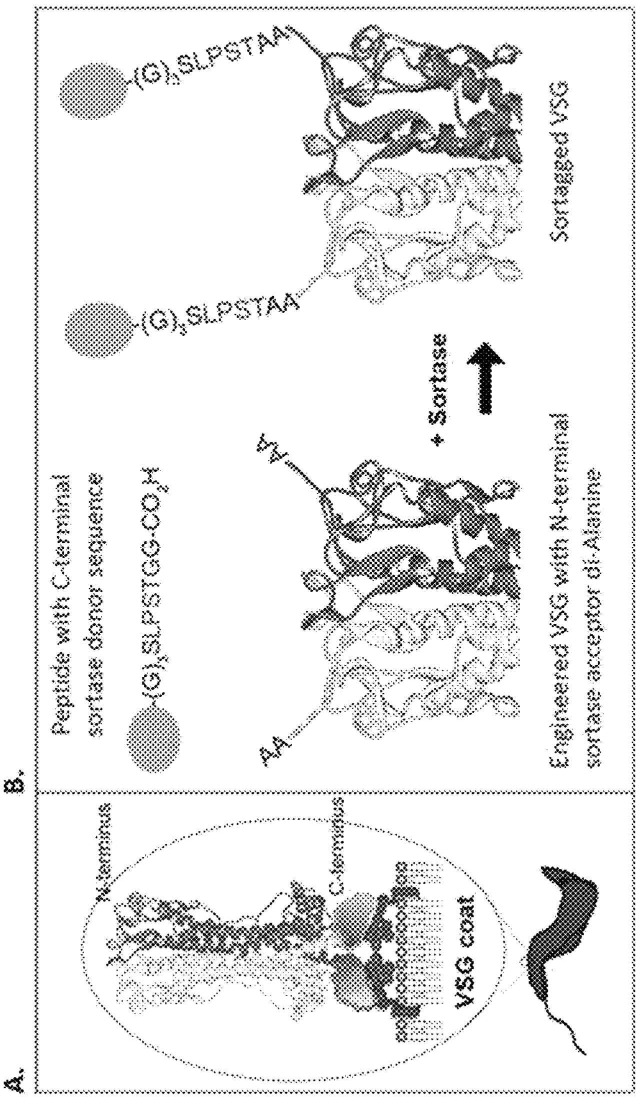

FIG. 6: shows an illustration of the overall method of sortagging the VSG coat of a Trypanosome. A. Visualization of a VSG protein homodimer embedded in the membrane of a Trypanosome via a glycophosphatidylinositol (GPI) anchor. Bottom: whole trypanosome. Top: Zoom on one VSG protein homodimer. B. Illustration of the sortagging reaction: modified VSG proteins (with an N-terminal di-Alanine), and small molecules (oval) linked to the sortase donor sequence LPSTGG (residues 2 through 7 of SEQ ID NO: 16), are covalently linked via a sortase reaction. The sortagged VSG is shown with the sorttag sequence $(G)_3$SLP-STAA (SEQ ID NO: 15).

FIG. 7: shows methods to detect Sortagging efficiency. A. Top image: Sortagging of VSG2-1DK (left) and VSG3-G4S (S317A) (right) detected via direct fluorescence (6-FAM). Fluorescent microscopic images of a *T. brucei* cell are shown at top (left: sortagged VSG2-1DK, right: sortagged VSG3-G4S). Bottom image: The 6-FAM sortagged VSGs were also analyzed by flow cytometry analysis using FACSCalibur. B. Sortagging of VGS2-1DK and VSG3-G4S (S317A) detected via FACS analysis of Trypanosomes using a monoclonal antibody against a small-molecule moiety (4-hydroxy-3-nitrophenylacetyl, abbreviated as NP here) followed by staining with an Allophycocyanin (APC)-conjugated mouse monoclonal IgG antibody (B1-8 clone, Abeam). C. A derivatized fentanyl hapten was chemically synthesized and conjugated to the N-terminus of a peptide containing a C-terminal sortase A donor sequence (fentanyl-GGGSLPSTGG, where fentanyl-conjugated compounds are alternatively denoted "Fen-" or "-Fen"). The peptide carrying the fentanyl hapten was conjugated to three different genetically modified VSGs (VSG2, VSG3 and ILTat1.24) using sortase A as described before. Chemical synthesis process of the fentanyl hapten has been described by M. D. Raleigh et al., J. Pharmacol. Exp. Ther. 368:282-291, 2019, and it has been adapted for sortase-mediated conjugation here. D. After sortase A-mediated conjugation of the fentanyl hapten to VSGs, a mouse monoclonal antibody against fentanyl (provided by M. Pravetoni, University of Minnesota) was conjugated to FITC using a kit (Abeam, ab102884) and used to stain the Sortagged VSGs followed by flow cytometry analysis using FACS-Calibur. Non-tagged VSGs were used as control for background staining. Below the graph: The mode and median of the data sets are shown. In both fentanyl and FAM conjugations, ILTat1.24 outperformed VSG2 and VSG3. Also, Sortagging efficiency of VSG3 was moderately higher than VSG2.

Figure 8A:
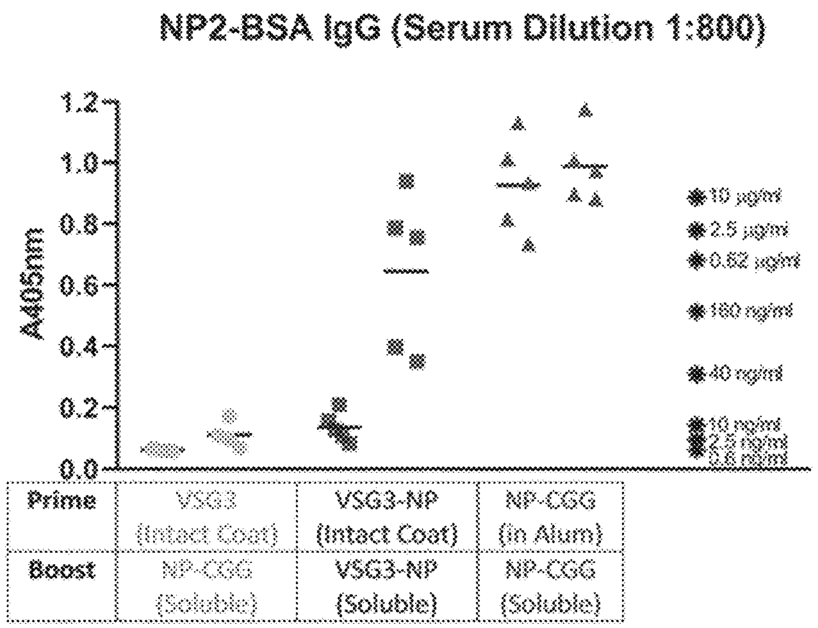
Figure 8B:
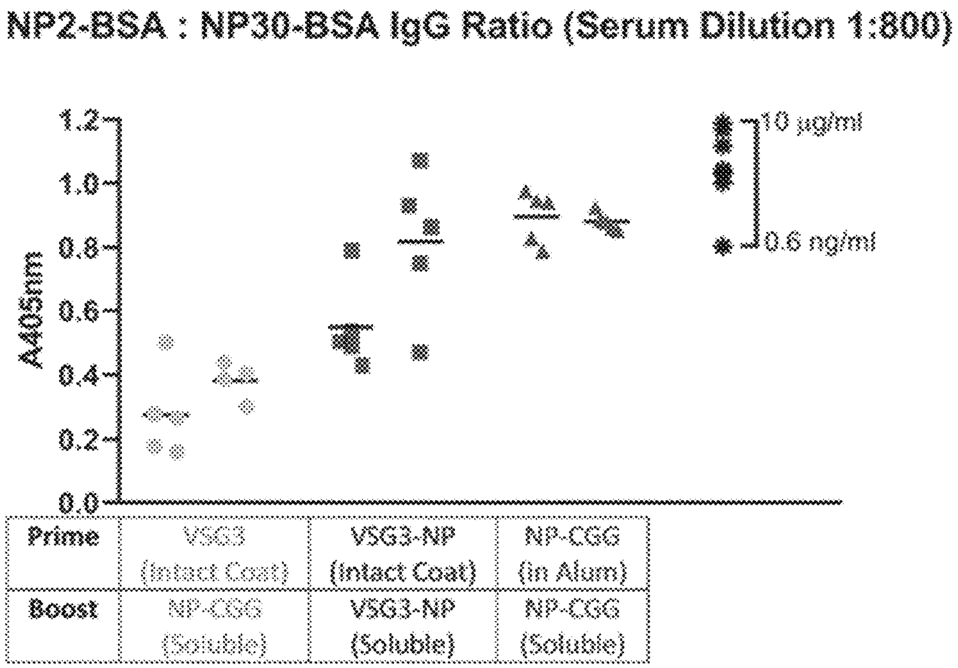
Figure 8C:
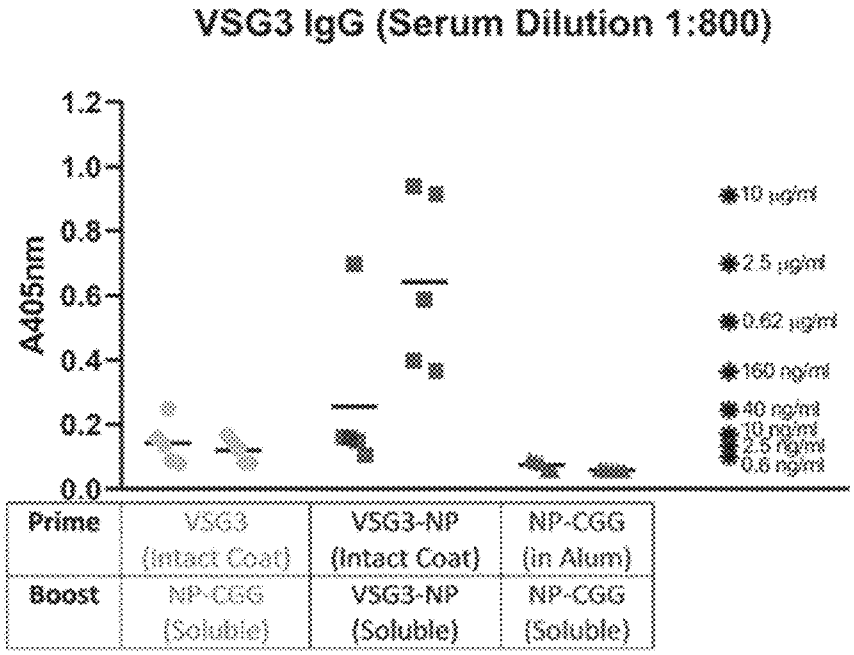

FIG. 8: shows a comparison of antibody responses to the small molecule 4-hydroxy-3-nitrophenyl acetyl (NP): Immunization with NP-labeled *T. brucei* vs. the "gold standard" hapten-carrier conjugate (i.e. NP-conjugated chicken gamma-globulin (NP-CGG) in Alum adjuvant). Five 6-8 weeks old female C57BL/6J mice per group were primed at day 0, 3 and 30 with intact VSG3(S317A), or VSG3-NP coats (i.e. U.V-irradiated intact *T. brucei* cells expressing sortaggable VSG3(S317A), either tagged or not tagged with NP hapten, without adjuvant) or with NP-CGG in Alum adjuvant. These mice received a soluble VSG3(S317A)-NP (in PBS, without adjuvant) booster at day 70 (or were boosted with soluble NP-CGG, in PBS without adjuvant, for the control group). A. The priming immunization with VSG-NP on intact trypanosomes followed by boosting with soluble VSG3(S317A)-NP, shows a clear IgG recall response and results in the generation of substantial IgG titers to the small molecule hapten NP. Titers were measured before and after boost and are shown at serum dilution 1:800. An anti-NP hapten monoclonal IgG (B1-8 clone, Abeam) was serially diluted (4-fold) to cover a range of concentrations from 10 μg/ml to 0.6 ng/ml. Immunization with the conjugated trypanosome coats results in high IgG titers to NP (average ~500 μg/ml). Furthermore, the fact that soluble VSG3-NP (in PBS, without adjuvant) induced a secondary IgG response strongly indicates that immunization with NP-conjugated VSG coats can induce a memory B cell response. While mean titers raised against NP-CGG in Alum are somewhat higher, boosting with soluble NP-CGG (in PBS, without adjuvant) did not induce a robust secondary response, which indicates lack of a memory B cell response after priming with NP-CGG in Alum. B. Immunization using VSG-NP on intact trypanosome coats followed by boosting with soluble VSG3(S317A) NP results in high affinity IgG (as defined by NP2/NP30 IgG titer ratios). Increase in NP2-BSA/NP30-BSA IgG ratio in VSG3-NP group indicates affinity maturation, a hallmark of memory B cell (recall) response. Immunization with the "gold standard" hapten-carrier conjugate (NP-CGG) in Alum provides no increase in affinity of anti-NP IgG antibodies. C. Immunization with VSG-NP on intact trypanosome coats followed by boosting with soluble VSG3(S317A)-NP also yields anti-VSG3 (anti-carrier) antibodies, but those are of a comparable magnitude (in μg/ml) to antisera raised to the NP hapten (as quantified by serial dilutions of an anti-VSG3 mouse monoclonal IgG (11D6 clone). Additional data demonstrate a lack of immunological cross-reactivity between the VSG2 and VSG3 carriers (not shown).

Figure 9A:
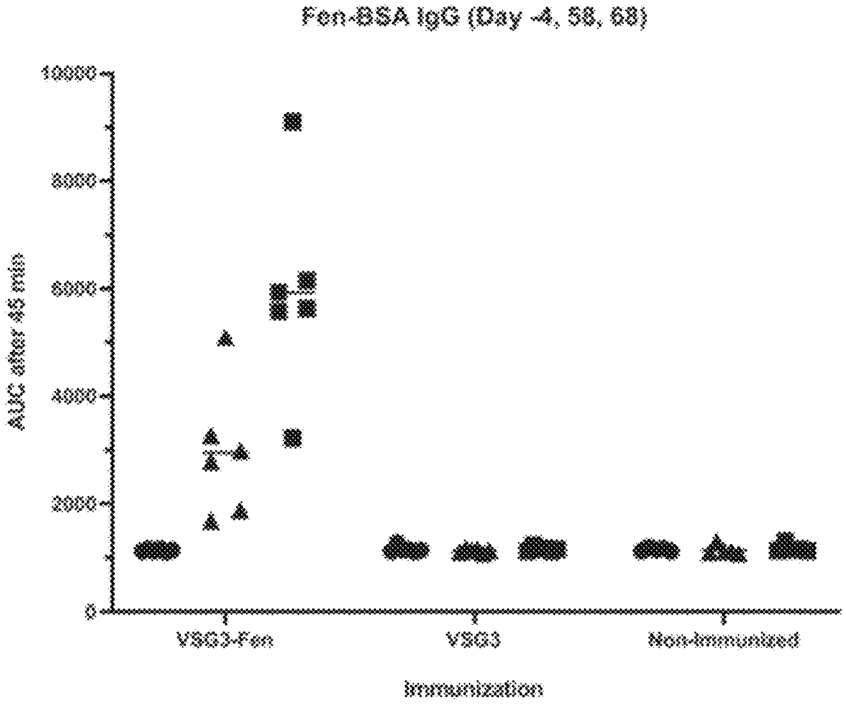
Figure 9B:
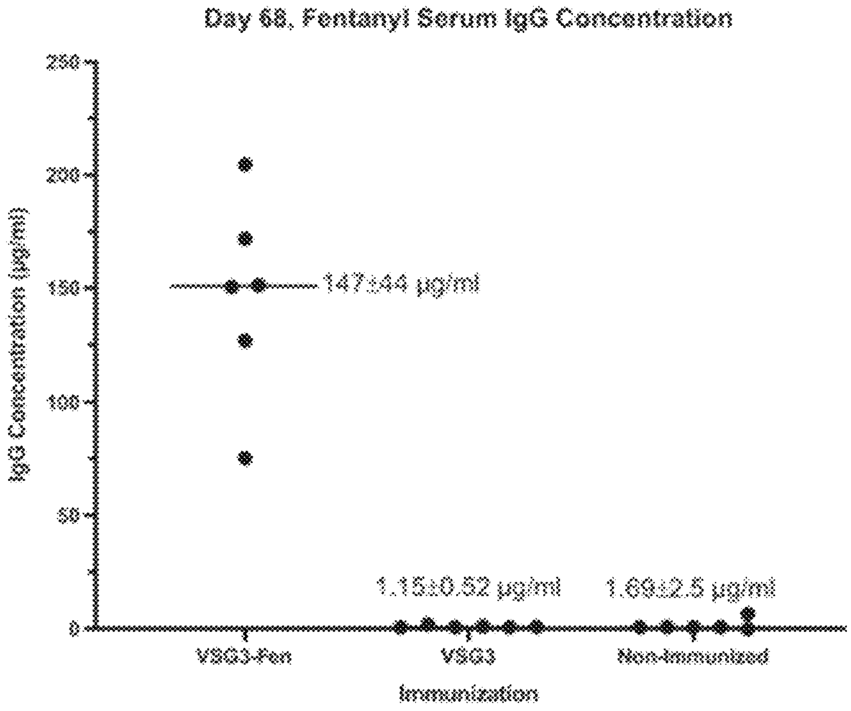
Figure 9C:
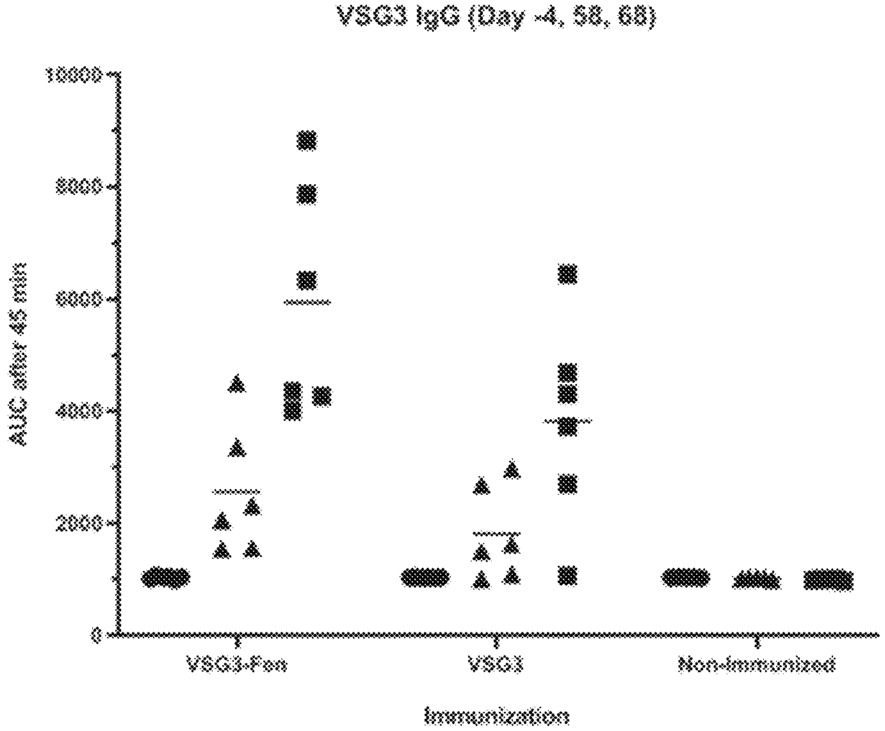

FIG. 9: shows that antibody responses to Fentanyl elicited by Fen-labeled *T. brucei* achieve high titers and memory (recall). ELISA measurement of serum IgG against fentanyl hapten and VSG3 carrier protein are shown. A. A tetra-Glycine peptide carrying an N-terminal fentanyl hapten (Fen-G4) was synthesized as described before. The Fen-G4 peptide was conjugated to BSA as a heterologous carrier protein and used to coat 96-well ELISA plates at 10 μg/ml. Six 6-8 weeks old female C57BL/6J mice per group were primed at day 0 and 30 with intact VSG3(S317A), or VSG3(S317A)-Fent coats (i.e. U.V-irradiated intact *T. brucei* cells expressing sortaggable VSG3(S317A), either tagged or not tagged with Fen-hapten, without adjuvant) via subcutaneous injection. These mice then received a soluble VSG3(S317A)-Fent (in PBS, without adjuvant) booster at day 60. Serum samples tested included the pre-immune (day-4), 2 days before (day 58) and 8 days after (day 68) 1 boost with soluble VSG3(S317A)-fentanyl protein. Anti-fentanyl IgG in sera was detected using an anti-mouse HRP conjugate (1:3000) followed by addition of ABTS substrate and $H_2O_2$ prepared in citrate-phosphate buffer pH 4.2.

Absorption of the samples were measured after 45 min at A405 nm using an ELISA reader (Tecan, Infinite M1000 Pro). B. A mouse monoclonal antibody against Fen-hapten was serially diluted to make a calibration curve in order to quantify IgG concentration in serum samples. Mean±standard deviation of 6 mice per group are shown. (C) Similarly, 96-well plates were coated with FPLC-purified VSG3(S317A) protein at 5 μg/well to measure serum IgG against VSG3(S317A) carrier protein. Area under curve (AUC) after 45 min, was calculated by GraphPad Prism. The circles, triangles and squares indicate sera at day −4, 58 and 68 respectively. Immunization with the conjugated trypanosome coats results in high IgG titers to fentanyl (average ~150 μg/ml). Furthermore, the fact that soluble VSG3 (S317A)-Fen (in PBS, without adjuvant) induced a secondary IgG response strongly indicates that immunization with Fen-conjugated VSG coats can induce a memory B cell response.

FIG. 10: shows that mice immunized with Fentanyl-haptenated *T. brucei* are protected from intoxication. A. Analgesic activity. Analgesic activity was tested by using the hotplate antinociception assay as described by Cox and Weinstock (1964). Fentanyl effect on hotplate antinociception was tested in unimmunized mice, in mice immunized with carrier only (VSG3(S317A)-only) or in mice immunized with haptenated VSG3(S317A)-Fen. In all cases mice were dosed with a cumulative fentanyl concentration of 0.1 mg/kg (s.c.). Fentanyl was administered subcutaneously every 15-30 minutes at increasing doses and the dose listed is the cumulative dose received. Hotplate antinociception was measured 15 minutes after the final fentanyl dose. Naloxone (0.1 mg/kg, s.c.) was administered 15 minutes after the final fentanyl dose. The effect of fentanyl is shown as latency to response. Fentanyl increased the latency to response after a cumulative dose of 0.1 mg/kg in unimmunized and VSG3-only immunized mice, compared with their baseline values. Naloxone completely reversed fentanyl-induced antinociception in both groups. Mice immunized with VSG3(S317A)-Fen did not show an increase in latency to response, compared to baseline, thus demonstrating that those mice did not get intoxicated by fentanyl at the same dose as the controls. Mean±standard deviation of 5 (unimmunized) or 6 mice per group are shown. B. Straub tail reaction (STR) measured per mouse per group. % denotes number of mice that demonstrated the Straub tail reaction, a dorsiflexion of the tail that is often almost vertical to the orientation of the body or curling back over the animal and stereotyped walking behavior (Bilbey et al, 1960). This phenomenon was first described as a response to opiates in mice (Straub, 1911), and is thought to be mediated by activation of the opioid receptor system because opioid receptor antagonists such as naloxone block the phenomenon (Aceto et al, 1969; Nath et al., 1994; Zarrindast et al, 2001).

Figure 11A:
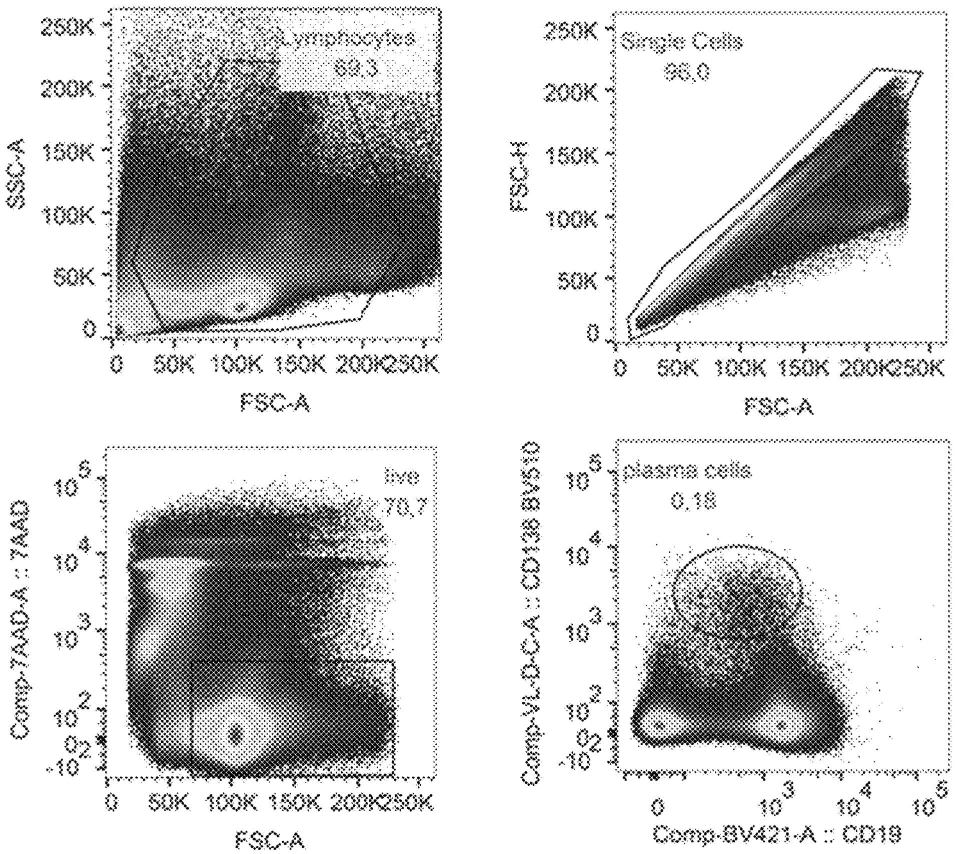
Figure 11B:
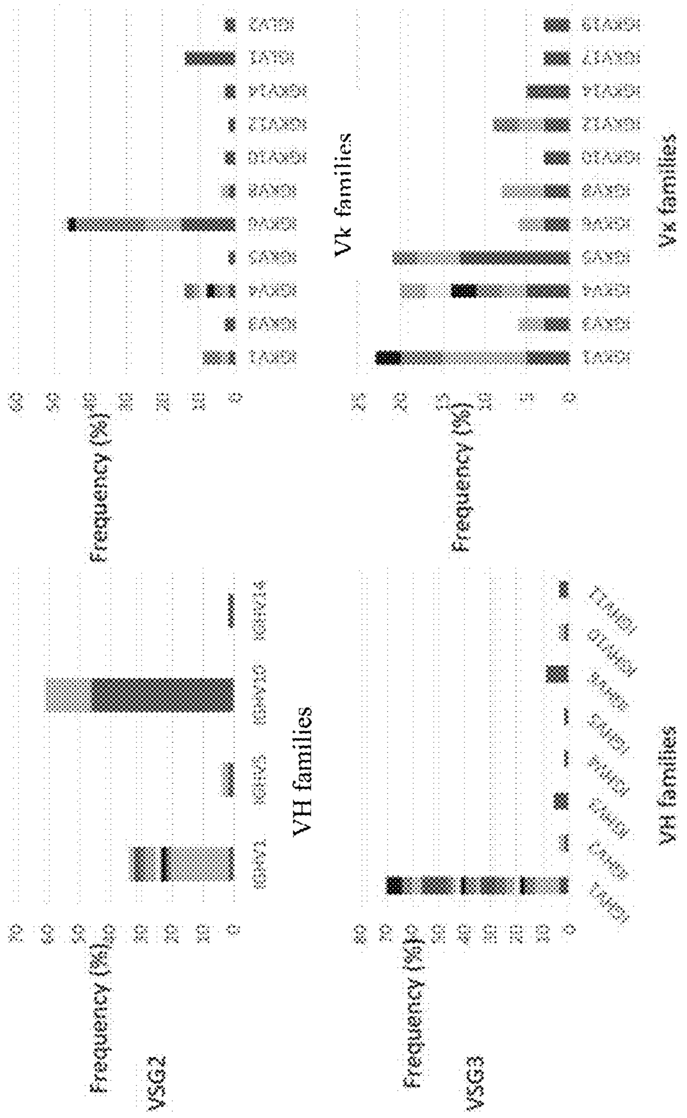

FIG. 11 shows that each distinct VSG coat elicits a unique subset of B cell specificities (thus, a unique B cell repertoire). Trypanosomes expressing either VSG2 trypanosome coats or the VSG3(S317A) version used in the fentanyl vaccination experiments (a more immunogenic form of VSG3 with serine 317 mutated to alanine) elicit distinct repertoires in C57BL/6 mice. A. Gating strategy for the isolation of plasma cells. Lymphocytes were isolated from spleens and analyzed on a LSR II instrument for plasma cells. Plasma cells were then isolated (single cell sorted) using an ARIA II cell sorter. Cells were stained using an anti-mouse CD19-BV421 and anti-mouse CD138-BV510 antibodies. 7AAD was included in all stainings to exclude dead cells. The data were analyzed using FlowJo v10 software. Ig gene cloning was performed as described before (Tiller et al., 2008). In brief, cDNA of each single cell was generated using random hexamer primers. Ig heavy and corresponding Ig kappa or Ig lambda light chain gene transcripts were amplified using a semi-nested PCR strategy (Tiller et al., 2008). Amplicons were Sanger sequenced and analyzed using NCBI IgBlast. B. V gene repertoires elicited by VSG2 or VSG3(S317A) coated trypanosomes. Histograms summarize the VH and Vκ gene family usage in Ig gene transcripts isolated from plasma cells from C57BL/6 mice exposed to VSG2 or VSG3(S317A) coated trypanosomes (59 and 53 distinct Ig transcripts respectively). Sequences were obtained from 4 and 8 different VH gene families for VSG2 and VSG3(S317A), respectively, and 11 Vκ gene families. Within one bar the different shades of gray show the distribution of different family members within the respective family. The VH10 family, followed by the VH1 family (the largest VH family) was preferably expressed by the majority of plasma cells isolated from the VSG2 mice whereas only very few plasma cells expressing the VH10 family were isolated from the VSG3(S317A) mice. For VSG3 mice, most plasma cells expressed the VH1 family. In the VSG2 mice plasma cells mainly expressed the VK6 family, whereas in VSG3(S317A) mice the Vk family usage was more divers (but mainly VK1, VK4 and VK5). The analyzed sequences clearly demonstrate that the two different VSGs elicit a different VH and Vk family repertoire in plasma cells. This specificity allows one to design optimal vaccination strategies using distinct VSG coat platforms, tailored to the "needs" of specific epitopes. For example, this method can be used to expand an infrequently present B cell that is nevertheless required to be clonally expanded to produce an optimal response against a specific target.

The sequences show:

SEQ ID NO: 1

```
>Tb427VSG-1: GB Accession X56761.2 | Trypanosoma brucei brucei | Lister427
| variant surface glycoprotein MITat 1.1 (Lister 427-1|Not fully assembled by me) |
Source = GenBank download 170507 | Protein length = 492
MATGRAKNTKWARWLSTAGLIIVVTLPATTMAAERTGLKATAWKPLCKLTTELSKVSGEMLNE

GQEVISNIQKIKAAEYICVSPILAKNPETQALQQLTLLRGYFARKTNGGLESYKTMGLATQIRSAR

AAAYLKGSIDEFLNLLESLKGGSENKCLVTTNADTAATRRETKLDDQECALSMPETKPEAATRT

ELTQTGYPNLQHGGGGTANTFQPTTSTGTCKLLSGHSTNGYPTTSALDTTAKVLAGYMTIPNTQ
```

-continued

VEATLANMQAMGNGHKATAPAWHEAWEARNREAKAKDLAYTNETGNLDTQPTLKALVKTLL

LPKDNTEHNAEATKLEALFGGLAADKTKTYLDMVDAEIIPAGIAGRTTEAPLGKIHDTVELGDI

LSNYEMIAAQNVVTLKKNLDAVSKKQQTESAENKEKICNAAKDNQKACENLKEKGCVFNTESN

KCELKKDVKEKLEKESKETEGKDEKANTMSNSFLIHKAPLLLAFLLF

SEQ ID NO: 2

>Tb427VSG-2: GB Accession X56762.1 | *Trypanosoma brucei brucei* | Lister427
| variant surface glycoprotein MITat 1.2 (Lister 427-2|Identical in my assembly) |
Source = GenBank download 170507 | Protein length = 476
MPSNQEARLFLAVLVLAQVLPILVDSAAEKGFKQAFWQPLCQVSEELDDQPKGALFTLQAAASK

IQKMRDAALRASIYAEINHGTNRAKAAVIVANHYAMKADSGLEALKQTLSSQEVTATATASYLK

GRIDEYLNLLLQTKESGTSGCMMDTSGTNTVTKAGGTIGGVPCKLQLSPIQPKRPAATYLGKAG

YVGLTRQADAANNFHDNDAECRIASGHNTNGLGKSGQLSAAVTMAAGYVTVANSQTAVTVQA

LDALQEASGAAHQPWIDAWKAKKALTGAETAEFRNETAGIAGKTGVTKLVEEALLKKKDSEAS

EIQTELKKYFSGHENEQWTAIEKLISEQPVAQNLVGDNQPTKLGELEGNAKLTTILAYYRMETA

GKFEVLTQKHKPAESQQQAAETEGSCNKKDQNECKSPCKWHNDAENKKCTLDKEEAKKVAD

ETAKDGKTGNTNTTGSSNSFVISKTPLWLAVLLF

SEQ ID NO: 3

>Tb427VSG-3: GB Accession AY935575.1 | *Trypanosoma brucei brucei* |
Lister427 | variant surface glycoprotein MITat 1.3 (Lister 427-3|Identical in my assembly) |
Source = GenBank download 170507 | Protein length = 509
MQAAALLLLVLRAITSIEAAADDVNPDDNKEDFAVLCALAALANLQTTVPSIDTSGLAAYDNLQ

QLNLSLSSKEWKSLFNKAADSNGSPKQPPEGFQSDPTWRKQWPIWVTAAAALKAENKEAAVL

ARAGLTNAPEELRNRARLALIPLLAQAEQIRDRLSEIQKQNEDTTPTAIAKALNKAVYGQDKET

GAVYNSADCFSGNVADSTQNSCKAGNQASKATTVAATIVCVCHKKNGGNDAANACGRLINHQS

DAGANLATASSDFGDIIATCAARPPKPLTAAYLDSALAAVSARIRFKNGNGYLGKFKATGCTGSA

SEGLCVEYTALTAATMQNFYKIPWVKEISNVAEALKRTEKDAAESTLLSTWLKASENQGNSVAQ

KLIKVGDSKAVPPAQRQTQNKPGSNCNKNLKKSECKDSDGCKWNRTEETEGDFCKPKETGTE

NPAAGTGEGAAGANTETKKCSDKKTEGDCKDGCKWDGKECKDSSILATKKFALTVVSAAFVAL

LF

SEQ ID NO: 4

>Tb427VSG-13: GB Accession AY935576.1 | *Trypanosoma brucei brucei* |
Lister427 | variant surface glycoprotein MITat 1.13 (Lister 427-13|Not fully assembled by me) |
Source = GenBank download 170507 | Protein length = 499
MQRLGTAVFFLLAFRYSTEQAVGLKEPNAPCYTTACGCKSRLLKRLDLYTSKYADGINNERENSE

AYSKLVTAALAAVPTMQRKILPLLGAAADILDICRRELATARPLVQAAISKIEEAAGVYNTLHKL

ERGLGEAKIEFGGTDLRLTKTKFRATSLGTIHTADCPNADPGETNVKIGLEHEENEPEPAKLIT

HGHLDATCASGVGQSSSCHTTAVEANTHLTLGLTFSGSSKDESATWNAATNNKRAIHSNDADF

LGSNATVAHEALKAIRSAGASTPCSSLITDFNAVRANPKFKLMVIKALLNKPTAEKESDAPADEV

NNAINSAYGREGSEYNTKTWKDIGSTRIPKADPPGEKTDTIDKLSSLPQWGDAIARLLLQEITKQ

EEQSIKTSSDEATNKECDKHTAKTEGECTKLGCDYDAENKKCKPKSEKETTAAGKKDRAAGET

GCAKHGTDKDKCENDKSCKWENNACKDSSILATKKFALSMVSAAFVTLLF

SEQ ID NO: 5

>X56767.1 | *Trypanosoma brucei brucei* | ILTat1 | mRNA variant surface
protein ILTat 1.24 | Source = GenBank download 170421 | Protein length = 514
MVYRNILQLSVLKVLLIVLIVEATHFGVKYELWQPECELTAELRKTAGVAKMKVNSDLNSFKTL

ELTKMKLLTFAAKFPESKEALTLRALEAALNTDLRALRDNIANGIDRAVRATAYASEAAGALFS

GIQTLHDATDGTTYCLSASGQGSNGNAAMASQGCKPLALPELLTEDSYNTDVISDKGFPKISPLT

NAQGQGKSGECGLFQAASGAQATNTGVQFSGGSRINLGLGAIVASAAQQPTRPDLSDFSGTAR

-continued

NQADTLYGKAHASITELLQLAQGPKPGQTEVETMKLLAQKTAALDSIKFQLAASTGKKTSDYKE

DENLKTEYFGKTESNIEALWNKVKEEKVKGADPEDPSKESKISDLNTEEQLQRVLDYYAVATM

LKLAKQAEDIAKLETEIADQRGKSPEAECNKITEEPKCSEEKICSWHKEVKAGEKNCQFNSTKA

SKSGVPVTQTQTAGADTTAEKCKGKGEKDCKSPDCKWEGGTCKDSSILANKQFALSVASAAFVA

LLF

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

The examples show:

Example 1

Drug-Decorated VSG Coats

The inventors have generated tools to derivatize the dense and homogeneous surface coat of the African trypanosome (*T. brucei*) for use as a display platform for (any) antigens to which antibodies need to be raised. These tools consist of:

(a) A specific vector to efficiently replace the expressed VSG (VSG2) with any other VSG of interest (see below). FIG. 1 contains the maps of two such plasmid vectors.

(b) Specific sets of VSGs of interest: these contain extended N-termini that are accessible to the enzyme sortase (here, derived from Streptococcus pyogenes). N-termini accessibility is determined by (i) relative placement on the VSG (determined structurally—FIG. 2 contains VSG2 and VSG3 whose N-termini are accessible, and as a comparison also VSG13, whose N-terminus is not accessible because of steric hindrance). It is also determined by (ii) the initiating amino acids, which must be Ala-Ala for the particular sortase employed (or Gly-Gly for sortases from other organisms).

(c) VSGs that fulfil those criteria are engineered into a modified Lister 427 strain of *T. brucei* by replacing the active VSG (see (a) above—FIG. 4 contains the amino acid sequences of three such VSGs: VSG3 (A), VSG2 (B) and ILTat1.24 (C); It is worth mentioning that the VSG3 that is engineered for sortagging purposes, contains a mutation (S317A) that removes a native glycosylation event which the inventors have recently shown to be immune-suppressive—Pinger et al., Nat. Microbiology, 2018).

(d) The modification of the Lister 427 strain of *T. brucei* consists of genetic deletion of the endogenous glycophosphatidylinositol phospholipase C (GPI-PLC), the enzyme that "sheds" VSG off the surface of dying cells (this is crucial to generating *T. brucei* that can be used as vaccine display platform, because unless GPI-PLC is removed from the genome, any form of inactivation of the parasite (e.g. UV-irradiation), that is crucial (i) to disallow switching and loss of the engineered VSG and (ii) to remove infectivity, will also lead to the disintegration of the VSG coat and of the cell itself (once VSGs are shed due to the action of GPI-PLC, the VSG coat disintegrates and the cells lyse—FIG. 5 explains that concept).

The herein disclosed method depends on "highjacking" the natural ability of *T. brucei* to elicit a neutralizing (and long-lasting) antibody response to its VSG coat, to produce antibodies at will. The inventors do this by decorating the *T. brucei* VSG coat not only with any peptide epitope/antigen but also sugars, lipids or small molecules and then using the decorated VSG coat as a vaccine carrier. Specifically, the inventors use the enzyme sortase A to covalently ligate any moiety to VSG coats genetically engineered to carry N-terminal sortase acceptor sequences (FIGS. 4 and 6).

Therefore, the inventors produce a His-tagged sortase A, derived from *Streptococcus pyogenes*, in *E.coli*, using a plasmid containing the *S. pyogenes*-derived sortase A expression construct (pSpSortA-pET28a). This plasmid is transformed into BL21 DE3 cells (Life Technologies C6000-03). Colonies from this transformation are used to inoculate large cultures of LB media (Sigma-Aldrich, L3022-1KG) which are then grown shaking at 37° C. to an optical density (OD600) of 0.4-0.8. Cultures are induced with 1 mM IPTG, grown for an additional 3-4 h and harvested by centrifugation. Cell pellets are resuspended in TBS/imidazole (20 mM Tris, 150 mM NaCl, 20 mM imidazole), and lysed using an EmulsiFlex-C5 homogenizer (Avestin). DNase-A powder (Sigma D5025) and 5 mM 2-Mercaptoethanol (2-ME) are added to the lysate, which is then clarified by centrifugation to remove particulates. The supernatant is passed is through a column packed with Ni-NTA agarose beads (QIAGEN, 30230) equilibrated with Wash Buffer (20 mM Tris, 300 mM NaCl, 20 mM imidazole, 5 mM 2-ME). The column is then washed with 100 ml of Wash Buffer and eluted with 30-35 ml of Elution Buffer (20 mM Tris, 300 mM NaCl, 200 mM imidazole, 5 mM 2-ME). Samples containing protein are then pooled and dialyzed in Dialysis Buffer (20 mM Tris, 150 mM NaCl, 1 mM DTT). The resulting sample is concentrated using a centrifugal filter unit (Arnicon Ultra-15, 10,000 NMWL, Merck Millipore), aliquoted and stored at −80° C. for future use.

The sortagging reaction is performed as follows: a mixture of sortagging solution containing 100 uM purified sortase A and 300-600 uM sortaggable-peptide in HMI-9 media is incubated on ice for 30-60 min (a sortaggable peptide includes any peptide with a C-terminal sortase donor sequence, LPSTGG, that can be attached at its N-terminus to another moiety; that moiety can be a fluorophore like 6-FAM, a small molecule like 4-Hydroxy-3-nitrophenyl acetyl (NP) hapten or other small molecules that are drugs of abuse (e.g. fentanyl etc.). GPI-PLC-negative *T. brucei* cells expressing engineered VSGs are then pelleted, resuspended in the sortagging mixture and incubated for 60 min at 4° C. on an inversion rotator. Cells are then pelleted, washed once with HMI-9 media and pelleted again before final resuspension in HMI-9 media (Hirumi and Hirumi, J. Parasitology, 1989). The efficiency of sortagging can be determined by direct FACS analysis or fluorescence microscopy (e.g. for fluorophores like 6-FAM) or by using specific monoclonal antibodies that bind the moieties decorating the VSG (FIG. 7 contains examples for 6-FAM, NP hapten and fentanyl hapten).

In proof of principle experiments this approach was used to generate (a) robust (in comparison to NP-CGG in Alum adjuvant) and (b) of consistent quality antibodies against a small-molecule hapten (4-hydroxy-3-nitrophenylacetyl or NP) (FIG. 8).

This approach can be used for a range of other small molecules (e.g. drugs of abuse like cocaine, nicotine, fentanyl, carfentanyl, tramadol, ketamine etc., but also chemotherapeutics like platinum, Adriamycin etc.; and also small molecules that are industrial by-products of chemical reactions), for toxins that mediate allergic reactions (e.g. aflatoxin and others) for specific peptides that function as important epitopes for infectious diseases (e.g. Plasmodium-derived peptides), for glycosylated or lipidated peptides (e.g. the aberrantly-glycosylated mucin peptides that have been considered as targets for anti-cancer vaccines etc.).

From the perspective of an anti-fentanyl (anti-overdose) vaccine, the major focus is to use this system to vaccinate "at risk" individuals (defined as individuals who are regular users or substance abusers but are not yet addicted/chemically dependent, or addicted individuals leaving rehabilitation centers, as proactive protection against overdose in case of recidivism, which typically will occur within the first two months after leaving rehab). Proof of concept that this has been achieved using the approach herein, is provided in FIGS. 9 and 10. Additionally, when this approach is coupled to repertoire analysis (FIG. 11), it will yield a wealth of anti-fentanyl monoclonal antibodies of varying affinities (directly accessible and ready to reconstitute from the paired immunoglobulin heavy and light chain sequences generated as a result of repertoire sequencing—FIG. 11). Such monoclonal antibody "sponges" can be used directly for therapeutic applications (e.g. anti-fentanyl antibody infusion together with methadone maintenance to curb bioavailability as well as cravings and accelerate therapeutic outcomes; or injection in the ER to blunt the effects of overdose in conjunction with naloxone—which acts quickly by antagonizing fentanyl binding to opioid receptors but which is metabolized faster than fentanyl, allowing delayed intoxication).

The Methodology: The ability of trypanosomes to stimulate a robust immune response in the infected individual (a response that is both long-lasting and neutralizing) is well documented. This invention renders this possible, at least in part, due to the discovery that a trypanosome's VSG protein is tolerant to the display of exogenous moieties with high efficiency on its surface using a bacterial transpeptidase sortase-based system (henceforth "sortagging").

Specifically, a sortase acceptor sequence specific to the sortase (for sortase A derived from *Streptococcus pyogenes* that is Ala-Ala and for Sortase A derived from *Staphylococcus aureus* that is Gly-Gly) can be added at the exposed N-terminal part of the VSG protein which, when it gets transported to the surface of the trypanosome, remains accessible to the sortase (see FIGS. 2 and 6). It is noted that VSGs initiate with the Methionine of a signal peptide, but that peptide is cleaved upon maturation—hence the mature VSG sequence is not initiating with Methionine. For instance both VSG2 and VSG3 (the preferred VSG variants) initiate with Ala-Ala, however the exact initiating amino acid must be empirically determined (using Edman degradation, which the inventors have done for both VSGs). Finally, while the endogenous Ala-Ala is present, it is inaccessible to sortase (and requires a short N-terminal extension as shown in FIG. 4). A complementary sortase donor sequence is then added C-terminally to the peptide/small molecule of interest (the actual sequence also depends on the sortase used; for sortase A derived from *Streptococcus pyogenes*, it is LPXTGG). LPXTGG can be added to a small molecule or other moiety with a reactive group (here the inventors use 6-FAM, or the hapten 4-hydroxy-3-nitrophenylacetyl abbreviated as NP, or Fen—FIG. 7).

Figure 7A:
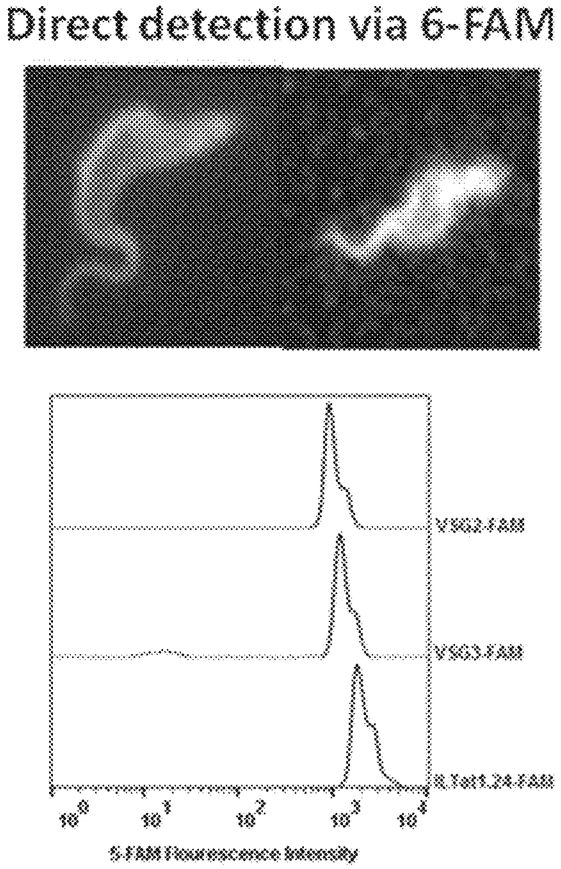
Figure 7B:
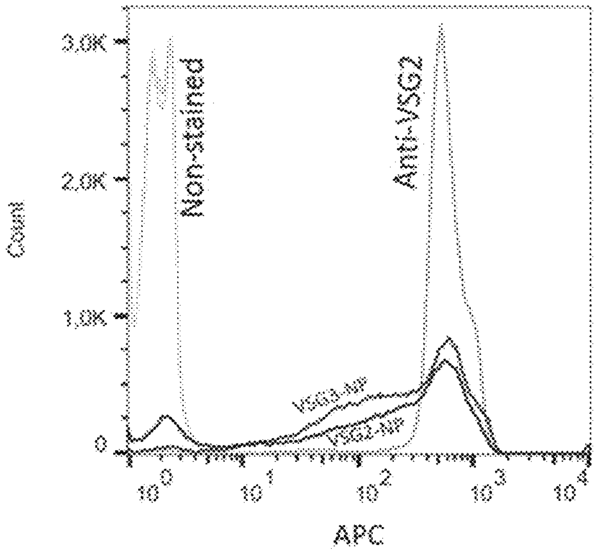
Figure 7C:
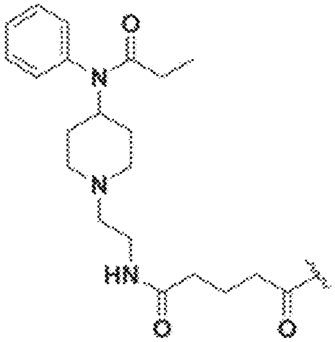
Figure 7D:
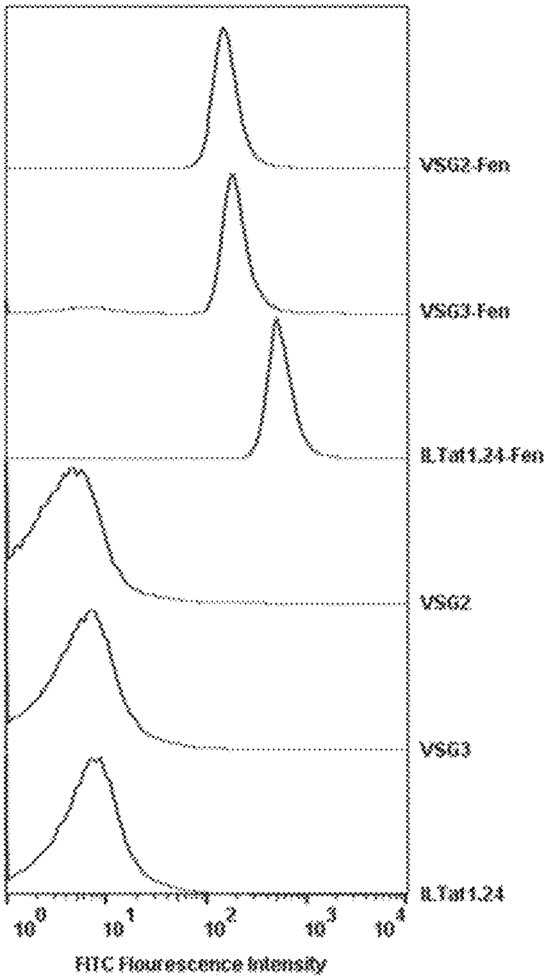

For fentanyl, the N-terminus of the sortase sequence is linked via an amide bond to the fentanyl hapten at the position located in FIG. 7D. While most moieties can be derivatized, a derivatization that retains the antigenicity of the small molecule-peptide conjugate (e.g. NP-GGGSLPSTGG) must be empirically determined (for example this was done through trial and error for nicotine and other small molecules, e.g. NicVax). The sortase then ligates NP-carrying peptide to the exposed N-terminus of the VSG on the surface of the trypanosomes (the inventors validate this using anti-small molecule antibodies, FIG. 7). It is also possible to insert the sortase signal sequence within the loops of VSG (as done for FLAG peptide in Stavropoulos and Papavasiliou, 2010). However in such situations it is advisable to use the sortase donor sequence (e.g. LPXTGG) within the VSG loops and the sortase acceptor sequence (e.g. Ala-Ala) on the decorating small molecule, to increase specificity. Due to the dense coat of VSGs on the surface of trypanosomes, the small molecule is then densely displayed on the surface. Upon trypanosome injection into a mammalian host, the small molecule-conjugated VSG coat is exposed to the host immune system which mounts a similar strong and specific priming immune response against the exposed hapten (e.g. NP) as it does against the VSG in natural infection (FIG. 8). Boosting can then be achieved with hapten-VSG conjugate either on the full coat (FIG. 8) or formulations thereof (e.g. soluble haptenated VSG but other formulations as well) achieving a scalability that is unique to this vaccine platform.

Interestingly, primary responses elicited by different VSGs are not cross-reactive (i.e. antibodies raised to VSG2 do not cross-react with VSG3 etc. Pinger et al., Nat. Communications, 2017). This suggests that each specific VSG elicits a unique subset of B cell specificities (thus, a unique repertoire) which could be more or less potent toward a specific set of small-molecule haptens. In context of the invention, specific VSGs are selected for specific haptens, for the elicitation of optimal anti-hapten responses (with some VSGs better platforms for certain haptens—FIG. 7). For example, good anti-HA (pan-influenza) antibodies require engagement of IGHV1-69, a "rare" IGH within the general repertoire. A VSG that elicits IGHV1-69 might therefore be engaged preferably if one desired to use this method to elicit polyspecific anti-influenza antisera (e.g. in a "pan-flu" vaccine). Direct proof that VSGs elicit distinct B cell repertoires (and that this system can provide a range of different platforms depending on the preference of B cell to be elicited) is provided in FIG. 11.

Biosafety concerns (e.g. disease causation) but also a need to block natural switching away from the haptenated VSG, dictate that derivatized trypanosome coats are inactivated (and thus unable to cause infection). The inventors have achieved this via UV-crosslinking of trypanosomes that lack the enzyme glycophosphatidylinositol phospholipase C (GPI-PLC) and are therefore dead—but with an intact VSG coat (trypanosomes wildtype for GPI-PLC disintegrate upon UV-inactivation as GPI-PLC cleaves the GPI linkage of each VSG off the membrane and sheds the coat (as depicted in FIG. 5). UV-crosslinking (of GPI-PLC-negative trypanosomes is achieved by pelleting cells from culture, washing with irradiation buffer (PBS supplemented with 55 mM Glucose), and resuspending in the same buffer to a density of $10^7$ cells/ml. 1 ml of this suspension is then aliquoted into each well of a 6-well tissue culture plate (Thermoscientific, 150239). Plates are UV-irradiated for 8 cycles, each cycle 30 S using a UVP crosslinker (Analytik Jena). Plates are swirled between irradiation cycles to ensure equal irradiation of trypanosomes. Irradiated cells are then resuspended at a concentration of $15\times10^6$ cells/ml. 200 µl of this solution ($3\times10^6$ trypanosomes) can be injected intraperitoneally or subcutaneously into mice.

Overall, using this inactivation protocol and sortaggable VSGs, the inventors have generated an optimal and flexible platform for the immunogenic display of antigenic determinants toward the generation of antibodies to small-molecule haptens and peptides, which can be expanded to a wide variety of antigenic entities (e.g. lipids, nucleic acids, etc.) Proof of concept regarding generation of antibodies to small molecules (e.g. NP) is shown in FIG. 9. Proof of principle that such antibodies can be raised against fentanyl and when generated protect against intoxication is provided in FIGS. 9 and 10. A cartoon version of the overall method is illustrated for the small molecule 6-FAM in FIG. 6.

An example of how to integrate the engineered VSGs of the invention into the *T.brucei* genome is provided in FIG. 3.

Generalizability of the approach: For the purposes of this application, the inventors focus on active immunotherapy against fentanyl, an adulterant of synthetic heroin and the cause of the majority of drug overdoses in the United States. This is because the inventors have tools already available (fentanyl haptenated to LPXTGG so that it can be sortagged; anti-fentanyl antibodies to verify sortaggability). However it should be clear that this approach can easily be adapted to raise effective antibodies against other drugs and drug metabolites (e.g. acetaminophen metabolites which cause liver toxicity, small molecules that are the toxins causal to anaphylactic shock in certain foodstuff allergies etc.). The approach can also be used for the haptenation with peptides derived from pathogens (e.g. the NANP tandem repeat, a major antigenic determinant of the Circumsporozoite protein of *Plasmodium falciparum*) or with aberrantly-glycosylated peptides unique to cancer cells (e.g. mucin) which can be used as anti-cancer vaccines (PMID: 20403708).

The invention claimed is:

1. An antigenic particle coated with an engineered variant surface glycoprotein (eVSG), wherein the eVSG comprises a VSG linked to an immunogenic compound, wherein the immunogenic compound is a small molecular drug, and which is covalently linked via a linker to the N-terminus of the VSG, wherein the VSG is VSG3 derived from the genome of *T. brucei.*

2. The antigenic particle according to claim 1, wherein the eVSG has the following covalent structure from N- to C-terminus: immunogenic compound, a sortagging donor sequence, a sortagging acceptor sequence, a linker, and the VSG protein sequence.

3. The antigenic particle according to claim 1, wherein the immunogenic compound is selected from (i) delta-9-tetrahydrocannabinol (THC) or synthetic cannabinoids or (ii) methamphetamine and derivatives thereof; or (iii) a synthetic cathinone; or (iv) an opioid; or (v) steroids, or is nicotine.

4. The antigenic particle according to claim 1, wherein the particle is a biological cell, a vesicle, a nanoparticle or a bead.

5. The antigenic particle according to claim 4, wherein the biological cell is a microorganism.

6. The antigenic particle according to claim 5, wherein the biological cell is an inactivated biological cell.

7. An immunogenic engineered VSG (ieVSG) protein, comprising in N- to C-terminal direction:

(a) An immunogenic compound, (b) A sortagging donor sequence, (c) A sortagging acceptor sequence, (d) A linker sequence, (e) A full length, or essentially full length, VSG protein, wherein the VSG is VSG3 derived from the genome of *T. brucei.*

8. A system or kit, comprising as components (i) a pre-ieVSG protein and (ii) a compound comprising a sortagging donor sequence, wherein the pre-ieVSG protein comprises in N-to C-terminal direction:

(a') Optionally a signal peptide, (b') A sortagging acceptor sequence, (c') A linker sequence, (d') A full length, or essentially full length, VSG protein, wherein the VSG is VSG3 derived from the genome of *T. brucei.*

9. The system or kit according to claim 8, further comprising, a sortase enzyme, or means for the generation of a sortase enzyme.

10. The system or kit according to claim 8, wherein the pre-ieVSG protein is provided as a nucleic acid sequence for the expression of a pre-ieVSG protein.

11. The system or kit according to claim 8, further comprising means for covalently attaching the sortagging donor sequence to a compound used as immunogen.

* * * * *